(12) United States Patent
Rienhoff, Jr.

(10) Patent No.: US 8,993,606 B2
(45) Date of Patent: Mar. 31, 2015

(54) ORAL FORMULATIONS FOR TREATING METAL OVERLOAD

(71) Applicant: FerroKin BioSciences, Inc., Wayne, PA (US)

(72) Inventor: Hugh Y. Rienhoff, Jr., San Carlos, CA (US)

(73) Assignee: FerroKin Biosciences, Inc., Wayne, PA (US)

( * ) Notice: Subject to any disclaimer, the term of this patent is extended or adjusted under 35 U.S.C. 154(b) by 0 days.

(21) Appl. No.: 13/708,087

(22) Filed: Dec. 7, 2012

(65) Prior Publication Data

US 2013/0225645 A1 Aug. 29, 2013

Related U.S. Application Data

(60) Provisional application No. 61/568,890, filed on Dec. 9, 2011, provisional application No. 61/569,914, filed on Dec. 9, 2011.

(51) Int. Cl.
| | | |
|---|---|---|
| *C07D 277/12* | (2006.01) | |
| *A61K 31/426* | (2006.01) | |
| *A61K 9/48* | (2006.01) | |

(52) U.S. Cl.
CPC ............ *C07D 277/12* (2013.01); *A61K 31/426* (2013.01); *A61K 9/4866* (2013.01)
USPC ........................................................ 514/365

(58) Field of Classification Search
CPC ... C07D 277/12; A61K 9/4866; A61K 31/426
See application file for complete search history.

(56) References Cited

U.S. PATENT DOCUMENTS

| | | |
|---|---|---|
| 2008/0214630 A1 | 9/2008 | Bergeron |
| 2009/0264484 A1 | 10/2009 | Tidmarsh et al. |
| 2010/0093812 A1 | 4/2010 | Bergeron, Jr. |
| 2010/0137383 A1* | 6/2010 | Tapper et al. .................. 514/365 |
| 2011/0160257 A1 | 6/2011 | Tapper et al. |
| 2012/0202857 A1 | 8/2012 | Tapper et al. |
| 2012/0270911 A1 | 10/2012 | Tapper et al. |

FOREIGN PATENT DOCUMENTS

| | | |
|---|---|---|
| WO | WO-2006-107626 A1 | 10/2006 |
| WO | WO-2008-115433 A1 | 9/2008 |
| WO | WO-2010/009120 A2 | 1/2010 |
| WO | WO-2011/017054 A2 | 2/2011 |
| WO | WO-2011-028255 A2 | 3/2011 |
| WO | WO-2011-140232 A2 | 11/2011 |

OTHER PUBLICATIONS

Bergeron, R J et al., "Design, Synthesis, and Testing of Non-Nephrotoxic Desazadesferrithiocin Polyether Analogues," J Med. Chem. 2008, 51(13), 3913-23.*
Mir et al. in emedicine.medscape.com/article/1389732-treatment (retrieved from the internet Nov. 19, 2014).*
Deferasirox in www.nlm.nih.gov/medlineplus/druginfo/meds/a606002.html (retrieved from the internet Nov. 13, 2014).*
Azarmi et al., Current perspectives in dissolution testing of conventional and novel dosage forms, International Journal of Pharmaceuticals, 328: 12-21 (2007).
Bergeron et al., Design, Synthesis, and Testing of Non-Nephrotoxic Desazadesferrithiocin Polyether Analogues, J Med Chem., 51(13): 3913-23 (2008).
International Search Report and Written Opinion of PCT/US12/68432 dated Feb. 5, 2013, 13 pages.
Bergeron, R.J. et al., (S)-4,5-dihydro-2-(2-hydroxy-4-hydroxyphenyl)-4-methyl-4- thiazolecarboxylic acid polyethers: a solution to nephrotoxicity, Journal of Medicinal Chemistry, 49(9):2772-83 (2006).
Bergeron, R.J. et al., Impact of the 3,6,9-trioxadecyloxy group on desazadesferrithiocin analogue iron clearance and organ distribution, Journal of Medicinal Chemistry, 50(14):3302-13 (2007).
Bergeron, R.J. et al., The impact of polyether chain length on the iron clearing efficiency and physiochemical properties of desferrithiocin analogues, Journal of Medicinal Chemistry, 53(7):2843-53 (2010).
Bergeron, R.J. et al., Desferrithiocin analogue iron chelators: iron clearing efficiency, tissue distribution, and renal toxicity, Biometals, Epub, 20 pages (2010).

* cited by examiner

*Primary Examiner* — Dennis Heyer
(74) *Attorney, Agent, or Firm* — Choate, Hall & Stewart, LLP; Fangli Chen; John P. Rearick

(57) ABSTRACT

The present invention provides, among other things, effective oral formulations based on desazadesferrithiocin polyether (DADFT-PE) analogs, salts and polymorphs thereof, as well as their application for treatment of metal overload, in particular, iron overload, and associated diseases, disorders and conditions.

10 Claims, 13 Drawing Sheets

ORAL FORMULATIONS FOR TREATING METAL OVERLOAD

RELATED APPLICATION

This application claims the benefit of U.S. Provisional Application 61/568,890, filed Dec. 9, 2011, and U.S. Provisional Application 61/568,914, filed Dec. 9, 2011. The entire contents of the above applications are incorporated herein by reference in their entireties.

BACKGROUND

Metal ions are critical to the proper functioning of living systems. Ions such as $Fe^{2+}$, $Zn^{2+}$, $Cu^{2+}$, $Ca^{2+}$, and $Co^{3+}$, to name but a few, can be found in the active sites of over a third of known enzymes and other functional proteins such as RNA polymerase, DNA transcription factors, cytochromes $P_{450}s$, hemoglobin, myoglobin, and coenzymes such as vitamin $B_{12}$. There, these metals serve to regulate oxidation and reduction reactions, stabilize or shield charge distributions, and orient substrates for reactions.

However, the body has a limited ability to absorb and excrete metals, and an excess can lead to toxicity. As one example, an excess of iron, whether derived from red blood cells chronically transfused, necessary in such conditions such as beta thalassemia major, or from increased absorption of dietary iron such as hereditary hemochromatosis can be toxic through the generation by iron of reactive oxygen species from $H_2O_2$. In the presence of $Fe^{2+}$, $H_2O_2$ is reduced to the hydroxyl radical (HO.), a highly reactive species, a process known as the Fenton reaction. The hydroxyl radical reacts very quickly with a variety of cellular constituents and can initiate free radicals and radical-mediated chain processes that damage DNA and membranes, as well as produce carcinogens. Without effective treatment, iron levels progressively increases with deposition in the liver, heart, pancreas, and other endocrine organs. Iron accumulation can result in produce (i) liver disease that may progress to cirrhosis and hepatocellular carcinoma, (ii) diabetes related both to iron-induced decreases in pancreatic β-cell secretion and increases in hepatic insulin resistance and (iii) heart disease, the leading cause of death in β-thalassemia major and other anemia associated with transfusional iron overload. Iron overload is also known to facilitated microbial infection in vertebrates by different strains of fungi, protozoa, gram positive, gram negative and acid-fast bacteria. This condition also facilitates viral infections in humans. Iron overload in humans is known to change the chemotactic and phagocytic properties of neutrophils, which leads to the reduction of their ability to kill invading pathogens. The T-cell function is also affected by these high concentrations of iron.

Other metals, especially those ions with little or no endogenous function, may find their way into the body and effect damage. Heavy metal ions such as $Hg^{2+}$ can replace ions such as $Zn^{2+}$ in metalloproteins and render them inactive, resulting in serious acute or chronic toxicity that can end in death or cause birth defects. Even more significantly, radioactive isotopes of the lanthanide and actinide series can cause grave illness to an individual exposed to them by mouth, air, or skin contact. Such exposure could result not only from the detonation of a nuclear bomb or a "dirty bomb" composed of nuclear waste, but also from the destruction of a nuclear power facility.

Traditional standard therapies for metal overload include the use of metal chelators such as deferoxamine (DFO, N'-[5-(acetyl-hydroxy-amino)pentyl]-N-[5-[3-(5-aminopentyl-hydroxy-carbamoyl)propanoylamino]pentyl]-N-hydroxy-butane diamide). DFO is an effective metal chelator; unfortunately, it is not orally bioavailable and has a very short half-life in serum. More recently, other metal chelators have been developed for clinical use, but have serious side effects including life-threatening agranulocytosis (deferiprone, Ferriprox™), renal and liver toxicity (deferesirox, Exjade™). Others are not as effective and require repeated daily doses.

Therefore, there is still a great need for a safe, effective and orally active metal chelator for the treatment of metal overload.

SUMMARY

The present invention provides a safe and effective oral formulation for treatment of metal overload based on desazadesferrithiocin analogs and derivatives in animals or a subject. The present invention is, in part, based on the unexpected discovery that desazadesferrithiocin analogs and derivatives have surprisingly good oral bioavailability. For example, as described in the Examples below, a desazadesferrithiocin analog (e.g., 3'-desazadesferrithiocin polyether magnesium salt) when administered in a capsule formulation can be rapidly distributed to bloodstream (e.g., serum $C_{max}$ reached within 60-90 minutes) and has a serum half-life longer than the typical half-life reported of the currently marketed metal chelators. The unexpectedly high oral bioavailability permits efficient metal chelating in patients. For example, once daily oral administration of a desazadesferrithiocin analog (e.g., 3'-desazadesferrithiocin polyether magnesium salt) at a dose as low as, e.g., 14.5 mg/kg of body weight reduces liver iron concentration in iron overload patients. In addition, desazadesferrithiocin analogs are surprisingly well tolerated even at high doses. For example, no serious side effects were observed in humans dosed at a daily dose higher than 40 mg/kg of body weight. Therefore, high daily doses, for example, daily doses greater than 32 mg/kg of body weight, or greater than 40 mg/kg of body weight can be safely used to achieve more effective therapeutic effects. As discussed above, prior to the present invention, poor oral bioavailability, short serum half-life and serious side effects are challenges faced by currently approved metal chelators. Thus, the present invention solves a long-standing problem in the field by providing a better, safer and more effective oral therapy for metal overload.

In one aspect, the present invention provides an oral formulation comprising a compound of Formula I at an amount effective to treat metal overload and a pharmaceutically acceptable excipient, wherein the compound of Formula I is:

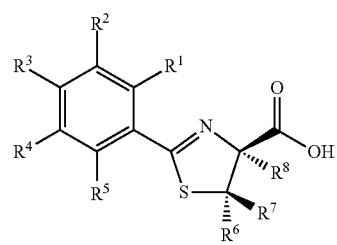

I wherein:
$R^1$, $R^2$, $R^3$, $R^4$, and $R^5$ are independently chosen from hydrogen, hydroxy, alkyl, arylalkyl, alkoxy, and $CH_3O$ $((CH_2)_n-O)_m-$, any of which may be optionally substituted;

$R^6$, $R^7$, and $R^8$ are independently chosen from hydrogen, halogen, hydroxy, lower alkyl, and lower alkoxy;

m is an integer from 0 to 8; and n is an integer from 0 to 8;

or a salt or polymorph thereof.

In some embodiments, $R^1$ is OH.

In some embodiments, $R^2$ is $CH_3O((CH_2)_n—O)_m—$. In some embodiments, $R^2$ is $CH_3O((CH_2)_n—O)_m—$, n is 2 and m is 3.

In some embodiments, $R^3$ is $CH_3O((CH_2)_n—O)_m—$. In some embodiments, $R^3$ is $CH_3O((CH_2)_n—O)_m—$, n is 2 and m is 3.

In some embodiments, $R^2$ or $R^3$ is $CH_3O((CH_2)_n—O)_m—$. In some embodiments, $R^2$ or $R^3$ is $CH_3O((CH_2)_n—O)_m—$, n is 2 and m is 3.

In some embodiments, a suitable compound of Formula I is a 3'-desazadesferrithiocin polyether, or a salt or polymorph thereof.

In certain embodiments, a suitable salt is selected from the group consisting of calcium, magnesium, potassium, di-potassium, sodium, di-sodium, zinc, piperazine, and combination thereof, and optionally as required by charge, includes an anion such as halide, carbonate, bicarbonate, hydroxide, carboxylate, sulfate, bisulfate, phosphate, nitrate, alkoxy having from 1 to 6 carbon atoms, sulfonate, and aryl sulfonate (e.g., $MgOH^+$).

In certain embodiments, a suitable salt is (S)-4,5-Dihydro-2-[2-hydroxy-3-(3,6,9-trioxadecyloxy)phenyl]-4-methyl-4-thiazolecarboxylate magnesium hydroxide. In particular embodiments, a suitable salt used in an oral formulation according to the present invention is (S)-4,5-Dihydro-2-[2-hydroxy-3-(3,6,9-trioxadecyloxy)phenyl]-4-methyl-4-thiazolecarboxylate magnesium hydroxide Form A polymorph. In other embodiments, a suitable salt used in an oral formulation according to the present invention is (S)-4,5-Dihydro-2-[2-hydroxy-3-(3,6,9-trioxadecyloxy)phenyl]-4-methyl-4-thiazolecarboxylate magnesium hydroxide Form B or C polymorph. In other embodiments, a suitable salt used in an oral formulation according to the present invention is (S)-4,5-Dihydro-2-[2-hydroxy-3-(3,6,9-trioxadecyloxy)phenyl]-4-methyl-4-thiazolecarboxylate magnesium hydroxide Form D polymorph. In other embodiments, a suitable salt used in an oral formulation according to the present invention is (S)-4,5-Dihydro-2-[2-hydroxy-3-(3,6,9-trioxadecyloxy)phenyl]-4-methyl-4-thiazolecarboxylate magnesium hydroxide Form E polymorph. Polymorph Forms A, B, C, D, and E are described in detail in the Examples section. In other embodiments, a suitable salt used in an oral formulation according to the present invention is amorphous (S)-4,5-Dihydro-2-[2-hydroxy-3-(3,6,9-trioxadecyloxy)phenyl]-4-methyl-4-thiazolecarboxylate magnesium hydroxide.

In some embodiments, a suitable salt is a 3'-desazadesferrithiocin polyether di-sodium salt. In some embodiments, a suitable salt is a 3'-desazadesferrithiocin polyether di-potassium salt.

In some embodiments, an amount effective to treat metal overload is an amount sufficient to provide a daily dose of at least about 10 mg/kg of body weight (e.g., at least about 12 mg/kg, 14 mg/kg, 16 mg/kg, 18 mg/kg, 20 mg/kg, 24 mg/kg, 28 mg/kg, 32 mg/kg of body weight). In certain embodiments, such daily doses are useful in the treatment of conditions such as non-transfusion dependent thalassemia.

In some embodiments, an amount effective to treat metal overload is an amount sufficient to provide a daily dose of at least about 32 mg/kg of body weight (e.g., at least about 34 mg/kg, 36 mg/kg, 38 mg/kg of body weight).

In some embodiments, an amount effective to treat metal overload is an amount sufficient to provide a daily dose of at least about 40 mg/kg of body weight (e.g., at least about 45 mg/kg, 50 mg/kg, 55 mg/kg, 60 mg/kg, 65 mg/kg, 70 mg/kg, 75 mg/kg, 80 mg/kg of body weight). In certain embodiments, such daily doses are useful in the treatment of conditions such as transfusion dependent hereditary and acquired anemias.

In some embodiments, an amount effective to treat metal overload is an amount sufficient to provide a daily dose ranging from about 10-250 mg/kg of body weight (e.g., about 10-200 mg/kg, 10-150 mg/kg, 10-100 mg/kg, 16-250 mg/kg, 16-200 mg/kg, 16-150 mg/kg, 16-100 mg/kg, 16-80 mg/kg, 32-250 mg/kg, 32-200 mg/kg, 32-150 mg/kg, 32-100 mg/kg, 32-80 mg/kg, 40-250 mg/kg, 40-200 mg/kg, 40-150 mg/kg, 40-100 mg/kg, 40-80 mg/kg, 40-60 mg/kg of body weight).

In some embodiments, the amount described herein may be calculated based on once daily or twice daily dosing schedule or several daily dosing schedules.

In some embodiments, an amount effective to treat metal overload, once administered regularly at an administration interval, results in serum $AUC_{inf}$ of the compound of Formula I within a range from approximately 120 to about 400 μg·h/mL (e.g., approximately 120-350 μg·h/mL, 120-300 μg·h/mL, 120-250 μg·h/mL, 120-200 μg·h/mL, 150-400 μg·h/mL, 150-350 μg·h/mL, 150-300 μg·h/mL, 150-250 μg·h/mL, 180-400 μg·h/mL, 180-350 μg·h/mL, 180-300 μg·h/mL, 180-250 μg·h/mL, 200-400 μg·h/mL, 200-350 μg·h/mL, 200-300 μg·h/mL).

In some embodiments, an amount effective to treat metal overload, once administered regularly at an administration interval, results in maximum serum concentration ($C_{max}$) of the compound of Formula I within a range from approximately 60 to about 150 μg/mL (e.g., approximately 60-140 μg/mL, 60-130 μg/mL, 60-120 μg/mL, 60-110 μg/mL, 60-100 μg/mL, 70-150 μg/mL, 70-140 μg/mL, 70-130 μg/mL, 70-120 μg/mL, 70-110 μg/mL, 70-100 μg/mL, 80-150 μg/mL, 80-140 μg/mL, 80-130 μg/mL, 80-120 μg/mL, 80-110 μg/mL, 80-100 μg/mL).

In some embodiments, the metal overload that can be treated by an oral formulation according to the present invention is iron overload. In some embodiments, the iron overload is transfusional iron overload. In other embodiments, the iron overload is caused by increased iron absorption.

In some embodiments, the metal overload is uranium overload. In some embodiments, uranium overload is caused by radiation poisoning.

In some embodiments, an oral formulation according to the invention is a solid dosage form, solution, or suspension formulation.

In particular embodiments, an oral formulation is a solid dosage form, for example, a capsule or tablet. In some embodiments, a solid dosage form according to the present invention has a strength (i.e., total fill weight, or total weight of the drug substance) of about 50 mg, 100 mg, 150 mg, 200 mg, 250 mg, 300 mg, 325 mg, 350 mg, 375 mg, 400 mg, 425 mg, 450 mg, 475 mg or 500 mg. In some embodiments, the compound of Formula I constitutes greater than 50%, 55%, 50%, 65%, 70%, 75%, 80%, 85%, 90%, 92%, 94%, 96%, 98% or more of the total fill weight (i.e., total weight of the drug substance in a solid dosage form).

In some embodiments, a solid dosage form according to the invention is characterized with a dissolution rate that results in greater than 50%, 55%, 60%, 65%, 70%, 75%, 80%, 85%, 90%, or 95% of the compound of Formula I dissolves in solution under 30 minutes in a dissolution assay conducted per a standard USP, European Pharmacopoeia, or British Pharmacopoeia protocol. In some embodiments, a solid dosage form according to the present invention is characterized with a dissolution rate that results in substantial disintegration under 30 minutes in a dissolution assay conducted per a standard USP, European Pharmacopoeia, British Pharmacopoeia protocol. In some embodiments, the dissolution assay is conducted in a dissolution medium containing a phosphate buffer solution, pH 6.8 with 0.5% (v/v) Tween 80, at, e.g., 50, 60, 70, 80, 90, or 100 revolutions per minute (RPM). In some embodiments, such a dissolution medium is prepared by dissolving 6.8 g of potassium phosphate monobasic and approximately 896 mg of sodium hydroxide in 1 L water, confirming pH of 6.8+/−0.05, adjusting, if needed, with either phosphoric acid or sodium hydroxide, dearating the medium with helium sparge, adding 5 mL of Tween 80 to an aliquot of the medium, stirring until dissolved, reintroducing back into the carboy, and mixing well. Such a dissolution medium can be scaled up as necessary. In some embodiments, a suitable dissolution assay for the invention is a Paddle™ method at 50 rpm in 900 ml of pH 6.0 buffer prepared with 0.01 mol/L sodium monohydrogenphosphate and 0.005 mol/L citric acid.

In particular embodiments, a solid dosage form according to the invention is characterized with a dissolution rate that results in greater than 50%, 55%, 60%, 65%, 70%, 75%, 80%, 85%, 90%, or 95% of the compound of Formula I dissolves in solution under 30 minutes in a dissolution assay conducted in a dissolution medium containing a phosphate buffer solution, pH 6.8 with 0.5% (v/v) Tween 80, at 50 revolutions per minute (RPM).

In some embodiments, an oral formulation according to the present invention is an immediate release formulation. In other embodiments, an oral formulation according to the present invention is a slow release or controlled release formulation.

In some embodiments, an oral formulation according to the invention contains a pharmaceutically acceptable excipient selected from the group consisting of a buffer, a preservative, a suspending agent, a thickening agent, a surfactant, an isotonic agent, a lubricant or glidant, a diluent, and combinations thereof. In particular embodiments, the pharmaceutically acceptable excipient is selected from croscarmellose sodium and/or magnesium stearate.

In a related aspect, the present invention provides a solid dosage form comprising a compound of Formula I and a pharmaceutically acceptable excipient, wherein the solid dosage form is characterized with a dissolution rate that results in greater than about 50% (e.g., greater than about 55%, 60%, 65%, 70%, 75%, 80%, 85%, 90%, 95%, or substantial disintegration) of the compound of Formula I dissolves in solution under 30 minutes in a dissolution assay conducted per a standard USP, European Pharmacopoeia, or British Pharmacopoeia protocol. In some embodiments, a solid dosage form according to the present invention is characterized with a dissolution rate that results in substantial disintegration under 30 minutes in a dissolution assay conducted per a standard USP, European Pharmacopoeia, British Pharmacopoeia protocol. In some embodiments, a suitable dissolution assay is conducted in a dissolution medium containing a phosphate buffer solution, pH 6.8 with 0.5% (v/v) Tween 80, at, e.g., 50, 60, 70, 80, 90, 100 revolutions per minute (RPM). In some embodiments, such a dissolution medium is prepared by dissolving 6.8 g of potassium phosphate monobasic and approximately 896 mg of sodium hydroxide in 1 L water, confirming pH of 6.8+/−0.05, adjusting, if needed, with either phosphoric acid or sodium hydroxide, dearating the medium with helium sparge, adding 5 mL of Tween 80 to an aliquot of the medium, stirring until dissolved, reintroducing back into the carboy, and mixing well. Such a dissolution medium can be scaled up as necessary.

In some embodiments, the compound of Formula I used in a solid dosage form according to the present invention is (S)-4,5-Dihydro-2-[2-hydroxy-3-(3,6,9-trioxadecyloxy) phenyl]-4-methyl-4-thiazolecarboxylate magnesium hydroxide. Thus, in particular embodiments, a solid dosage form according to the invention comprises (S)-4,5-Dihydro-2-[2-hydroxy-3-(3,6,9-trioxadecyloxy)phenyl]-4-methyl-4-thiazolecarboxylate magnesium hydroxide and a pharmaceutically acceptable excipient, wherein the solid dosage form is characterized with a dissolution rate that results in greater than 50%, 55%, 60%, 65%, 70%, 75%, 80%, 85%, 90%, or 95% of the compound of Formula I dissolves in solution under 30 minutes in a dissolution assay conducted in a dissolution medium containing a phosphate buffer solution, pH 6.8 with 0.5% (v/v) Tween 80, at 50 revolutions per minute (RPM). In various embodiments, (S)-4,5-Dihydro-2-[2-hydroxy-3-(3,6,9-trioxadecyloxy)phenyl]-4-methyl-4-thiazolecarboxylate magnesium hydroxide Form A, B, C, D, or E polymorph may be used in a solid dosage form described herein.

In certain embodiments, a solid dosage form according to the invention further comprises croscarmellose sodium and magnesium stearate. In particular embodiments, the present invention provides a solid dosage form comprising about 96% of (S)-4,5-Dihydro-2-[2-hydroxy-3-(3,6,9-trioxadecyloxy)phenyl]-4-methyl-4-thiazolecarboxylate magnesium hydroxide; 3% of croscarmellose sodium; and 1% of magnesium stearate.

In some embodiments, the compound of Formula I used in a solid dosage form according to the invention is a suitable salt which is a 3'-desazadesferrithiocin polyether di-sodium salt. In some embodiments, a suitable salt is a 3'-desazadesferrithiocin polyether di-potassium salt.

In some embodiments, a solid dosage form provided is a capsule or tablet with a strength (e.g., total fill weight) of, for example, about 50 mg, 100 mg, 150 mg, 200 mg, 250 mg, 300 mg, 325 mg, 350 mg, 375 mg, 400 mg, 425 mg, 450 mg, 475 mg or 500 mg. In some embodiments, the compound of Formula I constitutes greater than 50%, 55%, 50%, 65%, 70%, 75%, 80%, 85%, 90%, 92%, 94%, 95%, 96%, 98% or more of the total fill weight (i.e., total weight of the drug substance in a solid dosage form).

In another aspect, the present invention provides use of an oral formulation (e.g., a solid dosage form) described herein in treating metal overload such as iron overload (e.g., transfusional iron overload), uranium overload and other types of metal overload.

In some embodiments, the present invention provides the use of an oral formulation or a solid dosage form described herein, for the preparation of a medicament for treating metal overload.

In some embodiments, the present invention provides the use of a compound of Formula I for the preparation of a medicament for treating metal overload, wherein the medicament comprises a compound of Formula I at a daily dose of at least 10 mg/kg of body weight.

In an alternate embodiment, the present invention provides the use of a compound of Formula I for the preparation of a medicament for the treatment of a microbial infection by a microbial strain whose growth is stimulated by the excessive availability of iron in the host, wherein the medicament comprises a compound of Formula I at a daily dose of at least 10 mg/kg of body weight. An iron requiring strain may be selected from the group consisting of *Aspergillus, Candida, Cryptococcus, Histoplasma, Mucor, Paracoccidiodes, Pneu-*

*mocystis, Pythium, Rhizopus, Trichosporon, Entamoeba, Leishmania, Naegleria, Plasmodium, Toxoplasma, Trichomonas, Tritrichomonas, Trypanasoma, Bacillus, Clostridium, Corynebacterium, Erysipelothrix, Listeria, Mycobacterium, Staphylococcus, Streptococcus, Tropheryma, Acinetobacter, Aeromonas, Alcaligenes, Campylobacter, Capnocytophaga, Chlamydia, Coxiella, Ehrlichia, Enterobacter, Escherichia, Helicobacter, Klebsiella, Legionella, Moraxella, Neisseria, Pasteurella, Proteus, Pseudomonas, Salmonella, Shigella, Vibrio,* and *Yersinia.*

In some embodiments, the compound of Formula I is a 3'-desazadesferrithiocin polyether, or a salt or polymorph thereof.

In some embodiments, a suitable salt is selected from the group consisting of calcium, magnesium, potassium, di-potassium, sodium, di-sodium, zinc, piperazine, and combination thereof, and optionally as required by charge, includes an anion such as halide, carbonate, bicarbonate, hydroxide, carboxylate, sulfate, bisulfate, phosphate, nitrate, alkoxy having from 1 to 6 carbon atoms, sulfonate, and aryl sulfonate (e.g., $MgOH^+$).

In certain embodiments, a suitable salt is (S)-4,5-Dihydro-2-[2-hydroxy-3-(3,6,9-trioxadecyloxy)phenyl]-4-methyl-4-thiazolecarboxylate magnesium hydroxide. In particular embodiments, a salt suitable for the use according to the present invention is (S)-4,5-Dihydro-2-[2-hydroxy-3-(3,6,9-trioxadecyloxy)phenyl]-4-methyl-4-thiazolecarboxylate magnesium hydroxide Form A polymorph. In other embodiments, a salt suitable for the use according to the present invention is (S)-4,5-Dihydro-2-[2-hydroxy-3-(3,6,9-trioxadecyloxy)phenyl]-4-methyl-4-thiazolecarboxylate magnesium hydroxide Form B, C, D, or E polymorph. In other embodiments, a salt suitable for the use according to the present invention is amorphous (S)-4,5-Dihydro-2-[2-hydroxy-3-(3,6,9-trioxadecyloxy)phenyl]-4-methyl-4-thiazolecarboxylate magnesium hydroxide.

In some embodiments, a suitable salt is a 3'-desazadesferrithiocin polyether di-sodium salt. In some embodiments, a suitable salt is a 3'-desazadesferrithiocin polyether di-potassium salt.

In some embodiments, a suitable daily dose for use according to the present invention is at least about 10 mg/kg of body weight (e.g., at least about 12 mg/kg, 14 mg/kg, 16 mg/kg, 18 mg/kg, 20 mg/kg, 24 mg/kg, 28 mg/kg, 32 mg/kg of body weight). In certain embodiments, such daily doses are useful in the treatment of conditions such as non-transfusion dependent thalassemia.

In some embodiments, a suitable daily dose for use according to the present invention is at least about 32 mg/kg of body weight (e.g., at least about 34 mg/kg, 36 mg/kg, 38 mg/kg of body weight).

In some embodiments, a suitable daily dose for use according to the present invention is at least about 40 mg/kg of body weight (e.g., at least about 45 mg/kg, 50 mg/kg, 55 mg/kg, 60 mg/kg, 65 mg/kg, 70 mg/kg, 75 mg/kg, 80 mg/kg of body weight). In certain embodiments, such daily doses are useful in the treatment of conditions such as transfusion dependent hereditary and acquired anemias.

In some embodiments, a suitable daily dose for use according to the present invention ranges from about 10-250 mg/kg of body weight (e.g., about 10-200 mg/kg, 10-150 mg/kg, 10-100 mg/kg, 16-250 mg/kg, 16-200 mg/kg, 16-150 mg/kg, 16-100 mg/kg, 16-80 mg/kg, 32-250 mg/kg, 32-200 mg/kg, 32-150 mg/kg, 32-100 mg/kg, 32-80 mg/kg, 40-250 mg/kg, 40-200 mg/kg, 40-150 mg/kg, 40-100 mg/kg, 40-80 mg/kg, 40-60 mg/kg of body weight).

In some embodiments, a suitable daily dose for use according to the present invention is selected from 10 mg/kg, 16 mg/kg, 32 mg/kg, 40 mg/kg, 45 mg/kg, 50 mg/kg, 55 mg/kg, 60 mg/kg, 65 mg/kg, 70 mg/kg, or 75 mg/kg of body weight. In some embodiments, a suitable daily dose for use according to the present invention is selected from 40 mg/kg, 45 mg/kg, 50 mg/kg, 55 mg/kg, 60 mg/kg, 65 mg/kg, 70 mg/kg, or 75 mg/kg of body weight.

In some embodiments, the suitable daily dose described herein is the initial dose for the treatment. For example, the initial daily dose for the treatment can be at least 10 mg/kg of body weight, 16 mg/kg of body weight, 20 mg/kg of body weight, 30 mg/kg of body weight, 40 mg/kg of body weight, or higher.

In various embodiments, use of the compound of Formula I results in no substantial adverse effects.

In some embodiments, the metal overload that can be treated using a of the invention is uranium overload caused by, for example, radiation poisoning.

In some embodiments, the metal overload that can be treated using an oral formulation (e.g., a solid dosage form) of the invention is iron overload.

In various embodiments, the iron overload that can be treated using an oral formulation (e.g., a solid dosage form) of the invention is due to repeated blood transfusion (i.e., transfusional iron overload) or increased iron absorption.

In various embodiments, the invention can be used to treat a subject suffering from anaemia that results in increased accumulation of iron in the body either due to need for repeated blood transfusions or increased iron absorption. Exemplary causes of anaemia include, but are not limited to, beta thalassemia major or intermedia, and other anemias including but not limited to non-transfusion dependent Thalassemia (NTDT—i.e. patients with clinically milder forms of thalassemia, such as β-thalassemia intermedia, α-thalassemia (HbH disease), and HbE/β-thalassemia, who require occasional or no blood transfusions), Blackfan-Diamond anemia, Fanconi's anemia and other inherited bone marrow failure syndromes, Sideroblastic anemia, congenital dyserythropoietic anemias, sickle cell disease, pyruvate kinase deficiency (and other red cell enzyme deficiency causing hemolytic anemia), aplastic anemia, refractory anemias, red cell aplasia, Myelodysplasia (MDS), chronic myelofibrosis, paroxysmal nocturnal hemoglobinuria); from increased absorption of dietary iron (in conditions such as hereditary hemochromatosis and porphyria cutanea tarda); from maldistribution or redistribution of iron in the body (e.g., resulted from conditions such as atransferrinemia, aceruloplasminemia, and Friedreich's ataxia); from transfusional iron overload from off-therapy leukemias, before and after bone marrow transplant and myelodysplastic syndrome; from diabetes or obesity; and/or from liver diseases (e.g., hepatitis).

In some embodiments, the invention can be used to treat a subject suffering from β-thalassemia-intermedia. In some embodiments, a use of the invention can be used to treat a subject suffering from β-thalassemia-major.

In some embodiments, the invention can be used to treat a subject suffering from iron overload due to repeated blood transfusions as a consequence of the subject suffering from sickle cell disease. In some embodiments, a use of the invention can be used to treat a subject suffering from Myelodysplastic Syndrome (MDS).

In some embodiments, the invention can be used to treat a subject who is an adult. In some embodiments, the invention can be used to treat a subject who is a pediatric patient. In some embodiments, the invention can be used to treat a subject who has a serum ferritin level greater than about 500 μg/L (e.g., greater than about 600 μg/L, 700 μg/L, 800 μg/L, 900 μg/L). In some embodiments, the invention can be used to treat a subject who has a serum ferritin level greater than about 1000 μg/L (e.g., greater than about 1200 μg/L, 1500 μg/L, 1800 μg/L, 2000 μg/L, 2500 μg/L). In some embodiments, a use of the invention can be used to maintain a serum ferritin level of about or below about 1000 μg/L (e.g., of about or below about 900 μg/L, 800 μg/L, 700 μg/L, 600 μg/L, or 500 μg/L). In some embodiments, the invention can be used to treat a subject who has liver iron concentration (LIC) greater than about 1 mg/g dry weight (e.g., greater than about 2, 3, 4, 5, 6, 7, 8, 9, or 10 mg/g dry weight or more). In some embodiments, the invention can be used to treat a subject who has liver iron concentration (LIC) greater than 7 mg/g dry weight (e.g., greater than about 8, 9, 10, 11, 12, 13, 14, or mg/g dry weight or more). In some embodiments, the invention can be used to maintain a liver iron concentration (LIC) of about or below 7 mg/g dry weight (e.g., about or below 6, 5, 4, 3, 2, or 1 mg/g dry weight) in a subject. In some embodiments, the invention can be used to treat a subject who has cardiac T2 value less than about 20 ms (e.g., less than about 18, 16, 14, 12, 10, 8, 6, 4 or 2 ms). In some embodiments, a use of the invention can be used to maintain a cardiac T2 value of or greater than about 20 ms (e.g., of or greater than about 22, 24, 26, 28, or 30 ms).

In various embodiments, the use of the compound of Formula I results in reduction of liver iron concentration (LIC) in the subject as compared to a baseline control (e.g., pre-treatment level). In some embodiments, the use of the compound of Formula I results in the level of LIC in the subject below 7 mg/g dry weight (e.g., below about 6, 5, 4, 3, 2, or 1 mg/g dry weight). In some embodiments, the use of the compound of Formula I results in a reduction of LIC of about 2-5 mg/g over a one year period. In some embodiments, the use of the compound of Formula I results in a reduction of LIC of about 2-4 mg/g over a one year period. In some embodiments, the use of the compound of Formula I results in a reduction of LIC of about 3 mg/g over a one year period. The LIC level may be determined by MRI.

In some embodiments, the use of the compound of Formula I results in reduction of serum ferritin level in the subject as compared to a baseline control. In some embodiments, the use of the compound of Formula I results in the serum ferritin level in the subject below 1000 μg/L (e.g., about 900 μg/L, 800 μg/L, 700 μg/L, 600 μg/L, or 500 μg/L).

In some embodiments, the administration of the compound of Formula I results in reduction of cardiac iron level in the subject as compared to a baseline control. The cardiac iron level may be measured using T2*MRI. In some embodiments, the administration of the compound of Formula I results in cardiac T2 value great than about 20 ms (e.g., greater than about 22, 24, 26, 28, or 30 ms).

In some embodiments, the daily dose for use is provided in a single dose.

In some embodiments, the daily dose for use is provided in two or more separate doses. In some embodiments, the two separate or more doses are divided equally. In some embodiments, the doses are divided such that at least 75% of the total daily amount is delivered in the first dose, and the remainder in the second dose. In some embodiments, the doses are given at least 6, 8 or 12 hours apart.

In some embodiments, a use according to the invention further comprises a step of adjusting the daily dose based on LIC level, cardiac iron level, serum ferritin level and/or serum creatinine in the subject.

In another aspect, the present invention provides a method for treating metal overload in a subject in need of treatment, comprising the step of administering to the subject a compound of Formula I (as described above), or a salt or polymorph thereof, at an oral daily dose of at least 10 mg/kg of body weight.

In some embodiments, the method of Formula I is a 3'-desazadesferrithiocin polyether, or a salt or polymorph thereof.

In some embodiments, a suitable salt is selected from the group consisting of calcium, magnesium, potassium, di-potassium, sodium, di-sodium, zinc, piperazine, and combination thereof, and optionally as required by charge, includes an anion such as halide, carbonate, bicarbonate, hydroxide, carboxylate, sulfate, bisulfate, phosphate, nitrate, alkoxy having from 1 to 6 carbon atoms, sulfonate, and aryl sulfonate (e.g., $MgOH^+$).

In some embodiments, the salt is selected from the group consisting of calcium, magnesium, potassium, sodium, di-sodium, di-potassium, zinc, piperazine and combination thereof.

In certain embodiments, the salt of the method of the invention is (S)-4,5-Dihydro-2-[2-hydroxy-3-(3,6,9-trioxadecyloxy)phenyl]-4-methyl-4-thiazolecarboxylate magnesium hydroxide. In particular embodiments, the salt of the method of the invention is the (S)-4,5-Dihydro-2-[2-hydroxy-3-(3,6,9-trioxadecyloxy)phenyl]-4-methyl-4-thiazolecarboxylate magnesium hydroxide Form A polymorph. In other embodiments, the salt of the method of the invention is the (S)-4,5-Dihydro-2-[2-hydroxy-3-(3,6,9-trioxadecyloxy)phenyl]-4-methyl-4-thiazolecarboxylate magnesium hydroxide Form B, C, D, or E polymorph.

In some embodiments, the salt of the method of the invention is a 3'-desazadesferrithiocin polyether di-sodium salt. In some embodiments, the salt of the method of the invention is a 3'-desazadesferrithiocin polyether di-potassium salt.

In some embodiments, a suitable daily dose according to the method of the invention is at least about 10 mg/kg of body weight (e.g., at least about 12 mg/kg, 14 mg/kg, 16 mg/kg, 18 mg/kg, 20 mg/kg, 24 mg/kg, 28 mg/kg, 32 mg/kg of body weight) of the compound for use. In certain embodiments, such daily doses are useful in the treatment of conditions such as non-transfusion dependent thalassemia.

In some embodiments, a suitable daily dose according to the method of the invention is at least about 10 mg/kg of body weight (e.g., at least about 12 mg/kg, 14 mg/kg, 16 mg/kg, 18 mg/kg, 20 mg/kg, 24 mg/kg, 28 mg/kg, 32 mg/kg of body weight).

In some embodiments, a suitable daily dose according to the method of the invention is at least about 32 mg/kg of body weight (e.g., at least about 34 mg/kg, 36 mg/kg, 38 mg/kg of body weight).

In some embodiments, a suitable daily dose according to the method of the invention is at least about 40 mg/kg of body weight (e.g., at least about 45 mg/kg, 50 mg/kg, 55 mg/kg, 60 mg/kg, 65 mg/kg, 70 mg/kg, 75 mg/kg, 80 mg/kg of body weight). In certain embodiments, such daily doses are useful in the treatment of conditions such as transfusion dependent hereditary and acquired anemias.

In some embodiments, a suitable daily dose according to the method of the invention ranges from about 10-250 mg/kg of body weight (e.g., about 10-200 mg/kg, 10-150 mg/kg, 10-100 mg/kg, 16-250 mg/kg, 16-200 mg/kg, 16-150 mg/kg, 16-100 mg/kg, 16-80 mg/kg, 32-250 mg/kg, 32-200 mg/kg, 32-150 mg/kg, 32-100 mg/kg, 32-80 mg/kg, 40-250 mg/kg, 40-200 mg/kg, 40-150 mg/kg, 40-100 mg/kg, 40-80 mg/kg, 40-60 mg/kg of body weight).

In some embodiments, a suitable daily dose according to the method of the invention is selected from 10 mg/kg, 16 mg/kg, 32 mg/kg, 40 mg/kg, 45 mg/kg, 50 mg/kg, 55 mg/kg, 60 mg/kg, 65 mg/kg, 70 mg/kg, or 75 mg/kg of body weight. In some embodiments, a suitable daily dose for use according to the method of the invention is selected from 40 mg/kg, 45 mg/kg, 50 mg/kg, 55 mg/kg, 60 mg/kg, 65 mg/kg, 70 mg/kg, or 75 mg/kg of body weight.

In some embodiments, the suitable daily dose of the compound described herein is the initial dose for the treatment. For example, the initial daily dose for the treatment can be at least 10 mg/kg of body weight, 16 mg/kg of body weight, 20 mg/kg of body weight, 30 mg/kg of body weight, 40 mg/kg of body weight, or higher.

In some embodiments, the suitable daily dose of the compound described herein selected from 10 mg/kg, 16 mg/kg, 32 mg/kg, 40 mg/kg, 45 mg/kg, 50 mg/kg, 55 mg/kg, 60 mg/kg, 65 mg/kg, 70 mg/kg, or 75 mg/kg of body weight.

In various embodiments, the method of treatment using a compound of Formula I results in no substantial adverse effects.

In some embodiments, the metal overload that can be treated according to a method as described above, is uranium overload caused by, for example, radiation poisoning.

In some embodiments, the metal overload that can be treated according to a method as described above, is iron overload.

In various embodiments, the iron overload that can be treated according to a method as described above, is due to repeated blood transfusion (i.e., transfusional iron overload) or increased iron absorption.

In various embodiments, the invention provides a method to treat a subject suffering from β-thalassemia-intermediate, β-thalassemia-major, non-transfusion dependent Thalassaemia (NTDT), Blackfan-Diamond anemia, Sideroblastic anemia, sickle cell disease, aplastic anemia, red cell aplasia, Myelodysplasia (MDS), chronic myelofibrosis, paroxysmal nocturnal hemoglobinuria, off-therapy leukemia, hereditary hemochromatosis, or porphyria cutanea tarda.

In some embodiments, the invention provides a method to treat a subject suffering from β-thalassemia-intermedia. In some embodiments, invention provides a method to treat a subject suffering from β-thalassemia-major.

In some embodiments, the invention provides a method to treat a subject suffering from iron overload due to repeated blood transfusions as a consequence of the subject suffering from sickle cell disease. In some embodiments, the invention provides a method to treat a subject suffering from Myelodysplastic Syndrome (MDS).

In some embodiments, the invention provides a method as described above for treating a subject who is an adult. In some embodiments, the invention provides a method as described above for treating a subject who is a pediatric patient. In some embodiments, the invention provides a method as described above to treat a subject who has a serum ferritin level greater than about 500 μg/L (e.g., greater than about 600 μg/L, 700 μg/L, 800 μg/L, 900 μg/L). In some embodiments, the invention provides a method as described above to treat a subject who has a serum ferritin level greater than about 1000 μg/L (e.g., greater than about 1200 μg/L, 1500 μg/L, 1800 μg/L, 2000 μg/L, 2500 μg/L). In some embodiments, the invention provides a method to maintain a serum ferritin level of about or below about 1000 μg/L (e.g., of about or below about 900 μg/L, 800 μg/L, 700 μg/L, 600 μg/L, or 500 μg/L). In some embodiments, the invention provides a method as described above to treat a subject who has liver iron concentration (LIC) greater than about 1 mg/g dry weight (e.g., greater than about 2, 3, 4, 5, 6, 7, 8, 9, or 10 mg/g dry weight or more). In some embodiments, the invention provides a method as described above to treat a subject who has liver iron concentration (LIC) greater than 7 mg/g dry weight (e.g., greater than about 8, 9, 10, 11, 12, 13, 14, or 15 mg/g dry weight or more). In some embodiments, the invention provides a method as described above to maintain a liver iron concentration (LIC) of about or below 7 mg/g dry weight (e.g., about or below 6, 5, 4, 3, 2, or 1 mg/g dry weight) in a subject. In some embodiments, a method as described above to treat a subject who has cardiac T2 value less than about 20 ms (e.g., less than about 18, 16, 14, 12, 10, 8, 6, 4 or 2 ms). In some embodiments, the invention provides a method as described above to maintain a cardiac T2 value of or greater than about 20 ms (e.g., of or greater than about 22, 24, 26, 28, or 30 ms).

In various embodiments, a method as described above, using a compound of Formula I results in reduction of liver iron concentration (LIC) in the subject as compared to a baseline control (e.g., pre-treatment level). In some embodiments, a method as described above, using a compound of Formula I results in the level of LIC in the subject below 7 mg/g dry weight (e.g., below about 6, 5, 4, 3, 2, or 1 mg/g dry weight). In some embodiments, a method as described above, using a compound of Formula I results in a reduction of LIC of about 2-5 mg/g over a one year period. In some embodiments, a method as described above, using a compound of Formula I results in a reduction of LIC of about 2-4 mg/g over a one year period. In some embodiments, a method as described above, using a compound of Formula I results in a reduction of LIC of about 3 mg/g over a one year period. The LIC level may be determined by MRI.

In some embodiments, a method as described above, using a compound of Formula I results in reduction of serum ferritin level in the subject as compared to a baseline control. In some embodiments, a method as described above, using a compound of Formula I results in the serum ferritin level in the subject below 1000 μg/L (e.g., about 900 μg/L, 800 μg/L, 700 μg/L, 600 μg/L, or 500 μg/L).

In some embodiments, a method as described above, comprises the step of administration of the compound of Formula I which results in reduction of cardiac iron level in the subject as compared to a baseline control. The cardiac iron level may be measured using T2*MRI. In some embodiments, a method as described above, comprises the step of administration of the compound of Formula I results in cardiac T2 value great than about 20 ms (e.g., greater than about 22, 24, 26, 28, or 30 ms).

In some embodiments, the invention provides a method as described above, wherein the daily dose for the compound is provided in a single dose.

In some embodiments, the daily dose for the compound is provided in two separate doses. In some embodiments, the two separate doses are divided equally. In some embodiments, the doses are divided such that at least 75% of the total daily amount is delivered in the first dose, and the remainder in the second dose. In some embodiments, the doses are given at least 6, 8 or 12 hours apart.

In some embodiments, a method according to the invention further comprises a step of adjusting the daily dose based on LIC level, cardiac iron level, serum ferritin level and/or serum creatinine in the subject.

In various embodiments, the invention provides a method as described above, comprising a compound of Formula I in a solid dosage form (e.g., a capsule or tablet).

In particular embodiments, the invention provides an oral formulation comprising (S)-4,5-Dihydro-2-[2-hydroxy-3-(3,6,9-trioxadecyloxy)phenyl]-4-methyl-4-thiazolecarboxylate magnesium hydroxide, croscarmellose sodium, and magnesium stearate, for use in treating iron overload in a subject who has liver iron concentration (LIC) greater than about 1 mg/g dry weight (e.g., greater than about 2, 3, 4, 5, 6, 7, 8, 9, 10, 11, 12, 13, 14, or 15 mg/g dry weight or more) at a daily dose greater than about 16 mg/kg of body weight (e.g., greater than about 18, 20, 22, 24, 26, 28, or 30 mg/kg of body weight). In particular embodiments, the invention provides an oral formulation comprising (S)-4,5-Dihydro-2-[2-hydroxy-3-(3,6,9-trioxadecyloxy)phenyl]-4-methyl-4-thiazolecarboxylate magnesium hydroxide, croscarmellose sodium, and magnesium stearate, for use in treating iron overload in a subject who has liver iron concentration (LIC) greater than about 1 mg/g dry weight (e.g., greater than about 2, 3, 4, 5, 6, 7, 8, 9, 10, 11, 12, 13, 14, or 15 mg/g dry weight or more) at a daily dose greater than about 32 mg/kg of body weight (e.g., greater than about 40, 45, 50, 55, 60, 65, 70, 75, or 80 mg/kg of body weight).

In particular embodiments, the invention provides an oral formulation comprising a di-sodium salt of (S)-4,5-Dihydro-2-[2-hydroxy-3-(3,6,9-trioxadecyloxy)phenyl]-4-methyl-4-thiazolecarboxylate, croscarmellose sodium, and magnesium stearate, for use in treating metal overload (e.g., iron overload) at a daily dose greater than about 16 mg/kg of body weight (e.g., greater than about 18, 20, 22, 24, 26, 28, or 30 mg/kg of body weight). In particular embodiments, the invention provides an oral formulation comprising a di-sodium salt of (S)-4,5-Dihydro-2-[2-hydroxy-3-(3,6,9-trioxadecyloxy)phenyl]-4-methyl-4-thiazolecarboxylate, croscarmellose sodium, and magnesium stearate, for use in treating metal overload (e.g., iron overload) at a daily dose greater than about 32 mg/kg of body weight (e.g., greater than about 40, 45, 50, 55, 60, 65, 70, 75, or 80 mg/kg of body weight).

In particular embodiments, the invention provides an oral formulation comprising a di-potassium salt of (S)-4,5-Dihydro-2-[2-hydroxy-3-(3,6,9-trioxadecyloxy)phenyl]-4-methyl-4-thiazolecarboxylate, croscarmellose sodium, and magnesium stearate, for use in treating metal overload (e.g., iron overload) at a daily dose greater than about 16 mg/kg of body weight (e.g., greater than about 18, 20, 22, 24, 26, 28, or 30 mg/kg of body weight). In particular embodiments, the invention provides an oral formulation comprising a di-potassium salt of (S)-4,5-Dihydro-2-[2-hydroxy-3-(3,6,9-trioxadecyloxy)phenyl]-4-methyl-4-thiazolecarboxylate, croscarmellose sodium, and magnesium stearate, for use in treating metal overload (e.g., iron overload) at a daily dose greater than about 32 mg/kg of body weight (e.g., greater than about 40, 45, 50, 55, 60, 65, 70, 75, or 80 mg/kg of body weight).

In various embodiments, the invention provides a solid dosage form comprising 96% of (S)-4,5-Dihydro-2-[2-hydroxy-3-(3,6,9-trioxadecyloxy)phenyl]-4-methyl-4-thiazolecarboxylate magnesium hydroxide, 3% of croscarmellose sodium, and 1% of magnesium stearate; wherein the solid dosage form has a strength of 50, 100, 200, 250 mg, 375 mg, or 500 mg.

In various embodiments, the invention provides a solid dosage form comprising 96% of a di-sodium salt of (S)-4,5-Dihydro-2-[2-hydroxy-3-(3,6,9-trioxadecyloxy)phenyl]-4-methyl-4-thiazolecarboxylate, 3% of croscarmellose sodium, and 1% of magnesium stearate; wherein the solid dosage form has a strength of 50, 100, 200, 250 mg, 375 mg, or 500 mg.

In various embodiments, the invention provides a solid dosage form comprising 96% of a di-potassium salt of (S)-4,5-Dihydro-2-[2-hydroxy-3-(3,6,9-trioxadecyloxy)phenyl]-4-methyl-4-thiazolecarboxylate, 3% of croscarmellose sodium, and 1% of magnesium stearate; wherein the solid dosage form has a strength of 50, 100, 200, 250 mg, 375 mg, or 500 mg.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The following drawings and figures are for illustration purposes only, not for limitation.

DEFINITIONS

Figure 1:
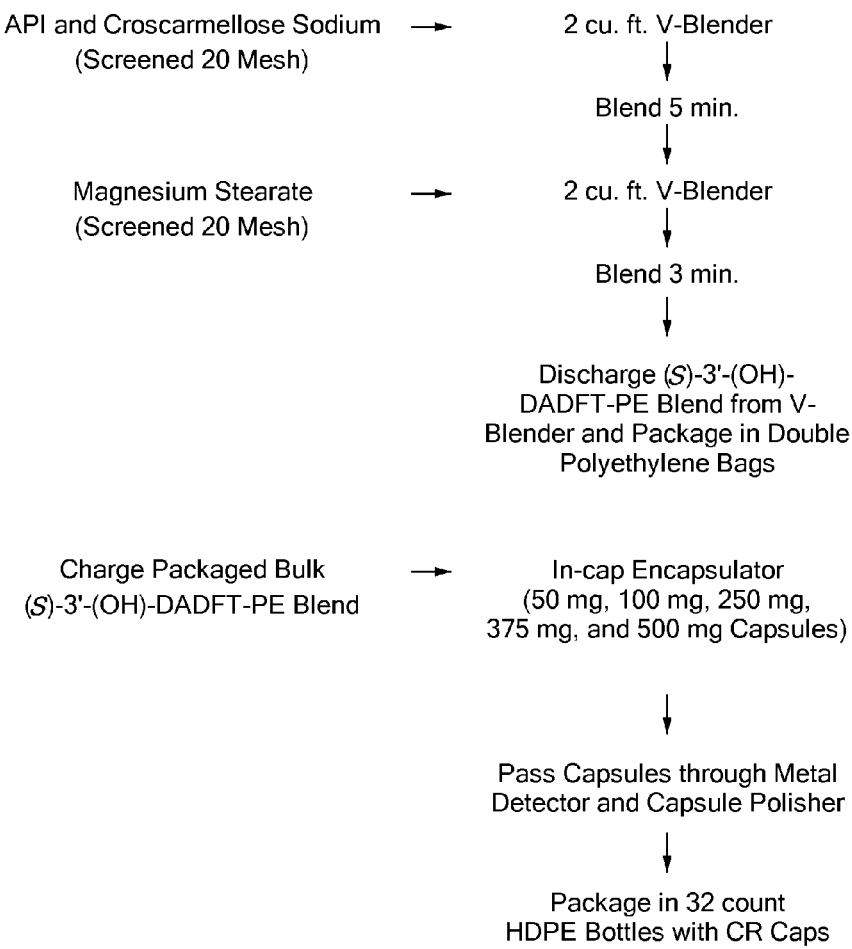
FIG. 1. (S)-3'-(OH)-DADFT-PE 50 mg, 100 mg, 200 mg, 250 mg, 375 mg, and 500 mg Capsules Exemplary Summary Flow Diagram.

In order for the present invention to be more readily understood, certain terms are first defined below. Additional definitions for the following terms and other terms are set forth throughout the specification.

Amorphous form: As used herein, the term "amorphous form" refers to a noncrystalline form of a substance.

Analogue: As used herein, the term "analogue" refers to a compound having a structure similar to that of another one, but differing from it in respect of a certain component. It can differ in one or more atoms, functional groups, or substructures, which are replaced with other atoms, groups, or substructures.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a hamster, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Analogue: As used herein, the term "analogue" refers to a compound having a structure similar to that of another one, but differing from it in respect of a certain component. It can differ in one or more atoms, functional groups, or substructures, which are replaced with other atoms, groups, or substructures.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Bioavailability: As used herein, the term "bioavailability" generally refers to the percentage of the administered dose that reaches the blood stream of a subject.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Chelation: As used herein, the term "chelation" means to coordinate (as in a metal ion) with and inactivate. Chelation also includes decorporation, a term which itself encompasses chelation and excretion.

Compound: As used herein, the term "compound" is meant to be interchangeable with the term "active compound" or "drug," and refers to a compound having beneficial prophylactic and/or therapeutic properties when administered to a patient and/or activity against a biological target which is associated with a disease.

Counterion: When the phrase "X is a counterion" is used in any formulae herein, and neither the compound nor the counterion is drawn showing explicit ionic character, such ionic character may be inferred and a corresponding charges on each moiety be assumed to be present or absent. For example, if X is a monovalent cation such as $Mg(OH)^+$, it may be inferred that the coupled compound has lost a proton to form an ionic bond with X, despite the formulae being drawn to explicitly show all protons in place. Similarly, when X is an anion, the coupled compound takes on cationic character. As used herein, the term counterion encompasses all possible placement where on a compound a counterion has bound and ratios of charges. Additionally, counterions and compounds may combine in uneven molar ratios to form solid salts. As those of skill in the art will recognize, different ratios of counterions may form stable arrangements and solid forms, including 1:1, 2:1, and 3:1 based on preferred oxidation states of each ion, salt formation conditions (including solvent), etc. All such forms are contemplated here.

Derivative: As used herein, the term "derivative" refers to a compound that is derived from a similar compound by some chemical or physical process.

Desolvated solvate: The term, "desolvated solvate," as used herein, refers to a crystal form of a substance which can only be made by removing the solvent from a solvate.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment. The "dosage strength" refers to the total drug content of the dosage form.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, the therapeutic agent is administered continuously over a predetermined period. In some embodiments, the therapeutic agent is administered once a day (QD) or twice a day (BID). In some embodiments, the therapeutic agent is administered once every two days. In some embodiments, the therapeutic agent is administered once a week.

Excipient: As used herein, the term "excipient" refers to any inert substance added to a drug and/or formulation for the purposes of improving its physical qualities (i.e. consistency), pharmacokinetic properties (i.e. bioavailability), pharmacodynamic properties and combinations thereof.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Pharmaceutically acceptable: As used herein, the term "pharmaceutically-acceptable" refers to any entity or composition that does not produce an undesirable allergic or antigenic response when administered to a subject.

Polymorphs: As used herein, the terms "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Prodrug: As used herein, the term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Solid: As used herein, "solid" when referring to a salt form means relatively solid, at room temperature, and/or containing a substantial amount of solids. A solid may be amorphous in form and/or be a solvated solid with some quantity of residual or coordinated of solvent molecules. A crystalline salt is an example of a solid. By way of example, a wax could be considered a solid, whereas an oil would not be. A "solid composition" as used herein includes a salt of a compound, or a polymorph or amorphous solid form thereof.

Solvate: As used herein, the term "solvate" refers to a crystal form of a substance which contains solvent. The term "hydrate" refers to a solvate wherein the solvent is water.

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, oral formulations for treatment of metal overload, in particular, iron overload, based on desazadesferrithiocin analogs and derivatives.

Various aspects of the invention are described in detail in the following sections. The use of sections is not meant to limit the invention. Each section can apply to any aspect of the invention. In this application, the use of "or" means "and/or" unless stated otherwise.

Desazadesferrithiocin Analogs, Salts and Polymorphs

The present invention can be used to formulate various desazadesferrithiocin analogs and derivatives including salts, polymorphs, esters, prodrugs, amides, or solvates.

In some embodiments, a suitable desazadesferrithiocin analog is a compound of Formula I:

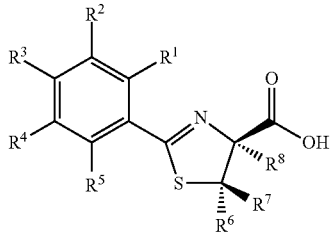

I or a salt or polymorph thereof, wherein:
$R^1$, $R^2$, $R^3$, $R^4$, and $R^5$ are independently chosen from hydrogen, hydroxy, alkyl, arylalkyl, alkoxy, and $CH_3O((CH_2)_n-O)_m-$, any of which may be optionally substituted;
$R^6$, $R^7$, and $R^8$ are independently chosen from hydrogen, halogen, hydroxy, lower alkyl, and lower alkoxy;
m is an integer from 0 to 8; and
n is an integer from 0 to 8;
or a salt or polymorph thereof.

In some embodiments, $R^8$ is chosen from hydrogen and methyl.

In some embodiments, $R^6$ and $R^7$ are independently chosen from hydrogen and methoxy.

In some embodiments, $R^1$ is hydroxy (OH).

In some embodiments, $R^2$, $R^3$, $R^4$, and $R^5$ are independently chosen from hydrogen and $CH_3O((CH_2)_n-O)_m-$.

In some embodiments, $R^2$ is $CH_3O((CH_2)_n-O)_m-$. In some embodiments, $R^2$ is $CH_3O((CH_2)_n-O)_m-$, n is 2 and m is 3.

In some embodiments, $R^3$ is $CH_3O((CH_2)_n-O)_m-$. In some embodiments, $R^3$ is $CH_3O((CH_2)_n-O)_m-$, n is 2 and m is 3.

In some embodiments, $R^2$ or $R^3$ is $CH_3O((CH_2)_n-O)_m-$. In some embodiments, $R^2$ or $R^3$ is $CH_3O((CH_2)_n-O)_m-$, n is 2 and m is 3.

In certain embodiments, salts of Formula I are solid.
In further embodiments, salts of Formula I are crystalline.
In further embodiments, salts of Formula I are amorphous.

It will be appreciated that where the present disclosure refers to a compound of Formula I, salts and polymorphs of a compound of Formula I are also included.

In some embodiments, compounds disclosed herein are salts or polymorphs thereof having structural Formula II:

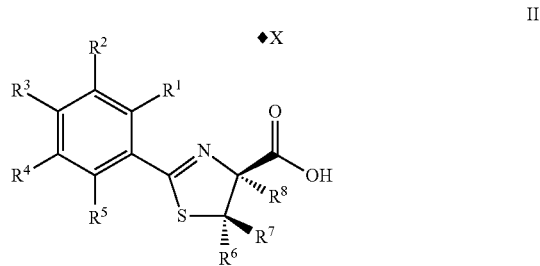

II or a salt or polymorph thereof,
wherein:
X is a counterion; and
each of $R^1$, $R^2$, $R^3$, $R^4$, $R^5$, $R^6$, $R^7$, and $R^8$ are as defined above and described in classes and subclasses herein, both singly and in combination. As used herein, the phrase "X is a counterion" may be inferred and a corresponding charges on each moiety be assumed to be present or absent. For example, if X is a monovalent cation such as $Mg(OH)^+$, it may be inferred that the coupled compound has lost a proton to form an ionic bond with X, despite the formulae being drawn to explicitly show all protons in place. Similarly, when X is an anion, the coupled compound takes on cationic character. As used herein, the term counterion encompasses all possible placement where on a compound a counterion has bound and ratios of charges. Additionally, counterions and compounds may combine in uneven molar ratios to form solid salts. As those of skill in the art will recognize, different ratios of counterions may form stable arrangements and solid forms, including 1:1, 2:1, and 3:1 based on preferred oxidation states of each ion, salt formation conditions (including solvent), etc. All such forms are contemplated here.

In certain embodiments, $R^8$ is chosen from hydrogen and methyl.

In further embodiments, $R^6$ and $R^7$ independently chosen from hydrogen and methoxy.

In further embodiments, $R^1$ is hydroxy.

In further embodiments, $R^2$, $R^3$, $R^4$, and $R^5$ are independently chosen from hydrogen and $CH_3O((CH_2)_n-O)_m-$.

In certain embodiments, salts of Formula II are solid.
In further embodiments, salts of Formula II are crystalline.
In further embodiments, salts of Formula II are amorphous.

In certain embodiments, the counterion X of Formula II is chosen from lysine, N-methyl-D-glucamine (NMG), tromethamine, calcium, magnesium, potassium, di-potassium, sodium, di-sodium, zinc, and piperazine. In some embodiments, X includes one or more metal cations and optionally, as required by charge, an anion such as halide, carbonate, bicarbonate, hydroxide, carboxylate, sulfate, bisulfate, phosphate, nitrate, alkoxy having from 1 to 6 carbon atoms, sulfonate, and aryl sulfonate (e.g., $MgOH^+$).

In further embodiments, salts and polymorphs thereof have structural formula III:

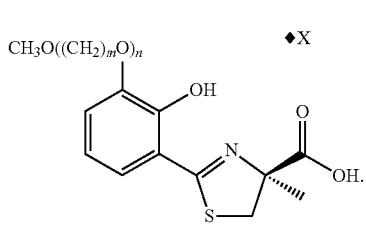

In further embodiments, salts and polymorphs thereof have structural formula IIIa:

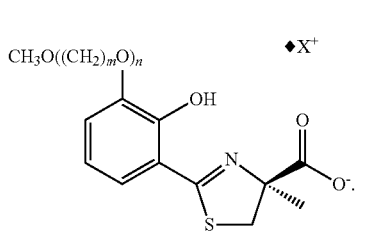

In certain embodiments, the salts and polymorphs thereof have structural formula IIIb:

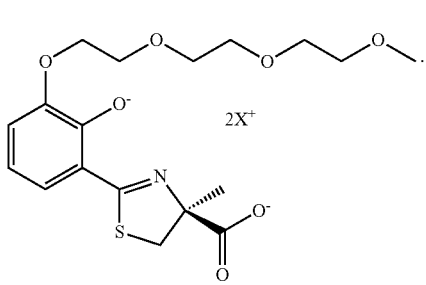

In certain embodiments, salts of Formula III, IIIa, and IIIb are solid.

In further embodiments, salts of Formula III, IIIa, and IIIb are crystalline.

In further embodiments, salts of Formula III, IIIa, and IIIb are amorphous.

In further embodiments, the counterion X is chosen from calcium, magnesium, potassium, di-potassium, sodium, di-sodium, zinc, and piperazine, and optionally as required by charge, includes an anion (e.g., $MgOH^+$). Exemplary such anions include, without limitation, halide, carbonate, bicarbonate, hydroxide, carboxylate, sulfate, bisulfate, phosphate, nitrate, alkoxy having from 1 to 6 carbon atoms, sulfonate, and aryl sulfonate.

In further embodiments, m is 2 and n is 3.

In further embodiments, the salt is the magnesium salt, or a polymorph thereof.

In further embodiments, the salt is magnesium 3'-desazadesferrithiocin polyether hydroxide or a polymorph thereof.

In further embodiments, said polymorph of magnesium 3'-desazadesferrithiocin polyether hydroxide is Form A.

In certain embodiments, salts and polymorphs thereof have structural formula IV:

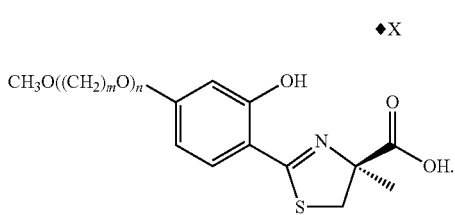

In further embodiments, salts and polymorphs thereof have structural formula IVa:

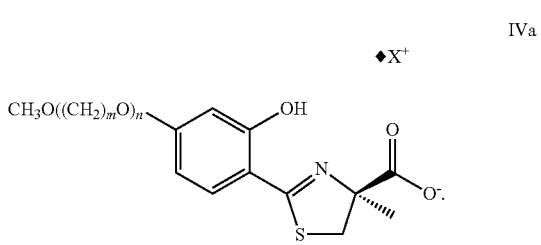

In certain embodiments, salts of Formula IV and IVa are solid.

In further embodiments, salts of Formula IV and IVa are crystalline.

In further embodiments, salts of Formula IV and IVa are amorphous.

In further embodiments, X is chosen from lysine, NMG, tromethamine, calcium, and magnesium, and optionally as required by charge includes an anion such as halide, carbonate, bicarbonate, hydroxide, carboxylate, sulfate, bisulfate, phosphate, nitrate, alkoxy having from 1 to 6 carbon atoms, sulfonate, and aryl sulfonate (e.g., $MgOH^+$).

In certain embodiments, salts and polymorphs thereof have structural formula V:

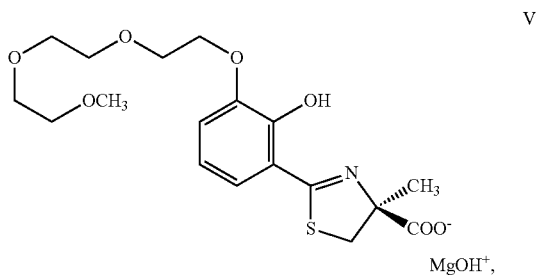

or, equivalently, magnesium hydroxide (S)-3'-desazadesferrithiocin polyether (Mg(OH).3'-DADFT-PE), or (S)-2-(2-hydroxy-3-(2-(2-(2-methoxyethoxy)ethoxy)ethoxy)phenyl)-4-methyl-4,5-dihydrothiazole-4-carboxylate magnesium hydroxide.

In certain embodiments, salts and polymorphs thereof have structural formula Va:

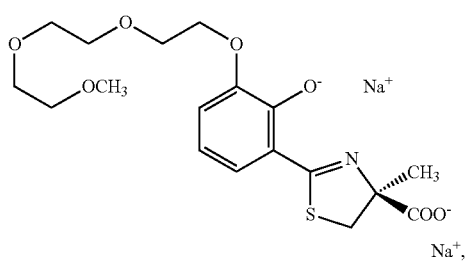

or, equivalently, di-sodium (S)-3'-desazadesferrithiocin polyether (Mg(OH).3'-DADFT-PE), or (S)-2-(2-hydroxy-3-(2-(2-(2-methoxyethoxy)ethoxy)ethoxy)phenyl)-4-methyl-4,5-dihydrothiazole-4-carboxylate disodium.

In certain embodiments, salts of Formula V and Va are solid.

In further embodiments, salts of Formula V and Va are crystalline.

In further embodiments, salts of Formula V and Va are amorphous.

The compound of formula V may exist in three substantially crystalline polymorphic forms referred to hereafter as Forms A, B, C, as well as an amorphous form, which differ from each other in their stability, physicochemical properties, and spectral characteristics. In particular embodiments, a suitable polymorph is Form A. The polymorph Forms A, B, and C are described in International Application WO 2010/009120, entitled "NOVEL SALTS AND POLYMORPHS OF DESAZADESFERRITHIOCIN POLYETHER ANALOGUES AS METAL CHELATION AGENTS," the disclosure of which is hereby incorporated by reference. The compound of formula V may exist in two other substantially crystalline polymorphic forms referred to hereafter as Forms D and E, as well as an amorphous form, which differ from each other in their stability, physicochemical properties, and spectral characteristics. In particular embodiments, a suitable polymorph is Form D. In particular embodiments, a suitable polymorph is Form E. Polymorphic Forms A, B, C, D, and E are further described in detail in Example 13.

In certain embodiments, salts and polymorphs thereof have structural formula VI:

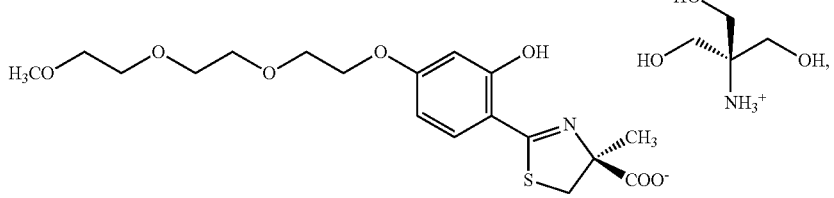

or, equivalently, tromethamine (S)-3'-desazadesferrithiocin polyether (tromethamine.4'-DADFT-PE), or 1,3-dihydroxy-2-(hydroxymethyl)propan-2-aminium (S)-2-(2-hydroxy-4-(2-(2-(2-methoxyethoxy)ethoxy)ethoxy)phenyl)-4-methyl-4,5-dihydrothiazole-4-carboxylate.

In certain embodiments, salts of Formula VI are solid.
In further embodiments, salts of Formula VI are crystalline.

In further embodiments, salts of Formula VI are amorphous.

As non-limiting examples, a suitable compound for the present invention is 3'-desazadesferrithiocin polyether, or a salt or polymorph thereof. A particular suitable salt is (S)-4,5-Dihydro-2-[2-hydroxy-3-(3,6,9-trioxadecyloxy)phenyl]-4-methyl-4-thiazolecarboxylate magnesium hydroxide. In certain particular embodiments, said (S)-4,5-Dihydro-2-[2-hydroxy-3-(3,6,9-trioxadecyloxy)phenyl]-4-methyl-4-thiazolecarboxylate magnesium hydroxide is the Form A polymorph.

In other embodiments, a suitable salt is a disodium salt of (S)-4,5-Dihydro-2-[2-hydroxy-3-(3,6,9-trioxadecyloxy)phenyl]-4-methyl-4-thiazolecarboxylate.

As used herein, when ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The terms "benzo" and "benz," as used herein, alone or in combination, refer to the divalent group $C_6H_4$=derived from benzene. Examples include benzothiophene and benzimidazole.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "hydroxy," as used herein, alone or in combination, refers to —OH.

The term "lower," as used herein, alone or in a combination, where not otherwise specifically defined, means containing from 1 to and including 6 carbon atoms.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridine, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The compounds disclosed herein can exist as therapeutically acceptable salts. Such salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid.

In addition to specific exemplary salts described above, representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, zinc, and calcium salts of the compounds disclosed herein, and the like.

Basic addition salts can be prepared during the final isolation and purification of the compounds, often by reacting a carboxy group with a suitable base such as the hydroxide, carbonate, or bicarbonate of a metal cation or with ammonia or an organic primary, secondary, or tertiary amine. The cations of therapeutically acceptable salts include, without limitation, lithium, sodium (e.g., NaOH), potassium (e.g., KOH), calcium (including Ca(OH)$_2$), magnesium (including Mg(OH)$_2$ and magnesium acetate), zinc, (including Zn(OH)$_2$ and zinc acetate) and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids such as l-glycine and l-arginine, and amino acids which may be zwitterionic at neutral pH, such as betaine (N,N,N-trimethylglycine) are also contemplated. See, for example, Berge et al. (1977) "Pharmaceutical Salts", *J. Pharm. Sci.* 66:1-19; incorporated herein by reference.

In certain embodiments, the salts may include lysine, N-methyl glutarate (NMG), tromethamine, calcium, magnesium, potassium, di-potassium, sodium, di-sodium, zinc, and piperazine salts of compounds disclosed herein. In some embodiments, the salts include one or more metal cations and, as required by charge, an anion such as halide, carbonate, bicarbonate, hydroxide, carboxylate, sulfate, bisulfate, phosphate, nitrate, alkoxy having from 1 to 6 carbon atoms, sulfonate, and aryl sulfonate (e.g., MgOH$^+$).

Salts disclosed herein may combine in 1:1 molar ratios, and in fact this is often how they are initially synthesized. However, it will be recognized by one of skill in the art that the stoichiometry of one ion in a salt to the other may be otherwise. Salts shown herein may be, for the sake of convenience in notation, shown in a 1:1 ratio; all possible stoichiometric arrangements are encompassed by the scope of the present invention.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), thermal gravimetric analysis (TGA), dynamic vapor sorption/desorption (DVS), single crystal X-ray diffractometry, vibrational spectroscopy, e.g. IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

Certain compounds, salts, and polymorphs from which pharmaceutical compositions as disclosed herein may be formed can be synthesized as described in US 20100137383 and Bergeron, R J et al., "Design, Synthesis, and Testing of Non-Nephrotoxic Desazadesferrithiocin Polyether Analogues," *J Med. Chem.* 2008, 51(13), 3913-23, which are hereby incorporated by reference in their entireties. Additional synthetic protocols for compounds disclosed herein may be found in US20080214630A1 published Sep. 4, 2008; US20100093812A1, published Apr. 15, 2010, and WO2011017054A2, published Feb. 10, 2011.

Formulations

According to the present invention, various desazadesferrithiocin analogs, salts and polymorphs described herein may be formulated for effective treatment of metal overload.

Oral Formulations

Among other things, the present invention provides effective oral formulations. Certain embodiments of the invention are based, at least in part, on the discovery that various formulations disclosed herein facilitate the effective oral delivery and distribution of a desazadesferrithiocin analog, salt or polymorph thereof, to serum, targeted tissues, cells and/or organelles, providing unexpectedly superior pharmacological, pharmacokinetic, and toxicity profiles. Among other things, formulations described herein are capable of solubilizing an active ingredient (e.g., a desazadesferrithiocin analog, salt or polymorph) at a desired amount suitable for the treatment of metal overload and are characterized by desired stability and tolerability when administered orally to a subject in need of treatment.

Accordingly, provided herein are pharmaceutical formulations which contain an active ingredient, i.e., a desazadesferrithiocin analog disclosed herein, or a pharmaceutically acceptable polymorph, salt, ester, prodrug, amide, or solvate thereof, together with one or more pharmaceutically acceptable carriers. The carrier(s) must be "acceptable" in the sense of being compatible with the other ingredients of the formulation and not deleterious to the recipient thereof.

Typically, an active ingredient is present in a therapeutically effective amount for treatment of metal overload. As used herein, the term "therapeutically effective amount" means an amount that is sufficient, when administered to a subject suffering from metal overload, to treat, prevent, and/or delay the onset of the symptom(s) associated with metal overload. It will be appreciated by those of ordinary skill in the art that a therapeutically effective amount is typically administered via a dosing regimen comprising one or more unit doses. Therapeutically effective amount of an active ingredient may be determined by various means. In some embodiments, a therapeutically effective amount is determined by daily doses. For example, a suitable formulation according to the invention may contain an active ingredient at an amount sufficient to provide a daily dose of at least about 10 mg/kg of body weight (e.g., at least about 12 mg/kg, 14 mg/kg, 16 mg/kg, 18 mg/kg, 20 mg/kg, 24 mg/kg, 28 mg/kg, 32 mg/kg, 34 mg/kg, 36 mg/kg, 38 mg/kg, 40 mg/kg, 45 mg/kg, 50 mg/kg, 55 mg/kg, 60 mg/kg, 65 mg/kg, 70 mg/kg, 75 mg/kg, 80 mg/kg of body weight). In some embodiments, a suitable formulation according to the invention may contain an active ingredient at an amount sufficient to provide a daily dose ranging from about 10-250 mg/kg of body weight (e.g., about 10-200 mg/kg, 10-150 mg/kg, 10-100 mg/kg, 16-250 mg/kg, 16-200 mg/kg, 16-150 mg/kg, 16-100 mg/kg, 16-80 mg/kg, 32-250 mg/kg, 32-200 mg/kg, 32-150 mg/kg, 32-100 mg/kg, 32-80 mg/kg, 40-250 mg/kg, 40-200 mg/kg, 40-150 mg/kg, 40-100 mg/kg, 40-80 mg/kg, 40-60 mg/kg of body weight).

In some embodiments, a therapeutically effective amount is determined by the maximum or total serum concentrations over time desired for effective treatment of metal overload. For example, a suitable formulation according to the invention may contain a therapeutically effective amount of an active ingredient that, once administered regularly at an administration interval, results in serum $AUC_{inf}$ of the active within a range from approximately 120 to about 400 µg·h/mL (e.g., approximately 120-350 µg·h/mL, 120-300 µg·h/mL, 120-250 µg·h/mL, 120-200 µg·h/mL, 150-400 µg·h/mL, 150-350 µg·h/mL, 150-300 µg·h/mL, 150-250 µg·h/mL, 180-400 µg·h/mL, 180-350 µg·h/mL, 180-300 µg·h/mL, 180-250 µg·h/mL, 200-400 µg·h/mL, 200-350 µg·h/mL, 200-300 µg·h/mL).

In some embodiments, a suitable formulation according to the invention may contain a therapeutically effective amount of an active ingredient that, once administered regularly at an administration interval, results in maximum serum concentration ($C_{max}$) of the active within a range from approximately 60 to about 150 µg/mL (e.g., approximately 60-140 µg/mL, 60-130 µg/mL, 60-120 µg/mL, 60-110 µg/mL, 60-100 µg/mL, 70-150 µg/mL, 70-140 µg/mL, 70-130 µg/mL, 70-120 µg/mL, 70-110 µg/mL, 70-100 µg/mL, 80-150 µg/mL, 80-140 µg/mL, 80-130 µg/mL, 80-120 µg/mL, 80-110 µg/mL, 80-100 µg/mL).

In some embodiments, formulations described herein are provided in various dosage forms. As used herein, dosage forms refer to a mixture of active ingredient and inactive components. Various dosage forms may be used according to the invention, including but not limited to, liquid dosage forms, solid dosage forms and semisolid dosage forms. In some embodiments, suitable dosage forms include a solution or a suspension in an aqueous liquid or a non-aqueous liquid; or as an oil-in-water liquid emulsion or a water-in-oil liquid emulsion, or suspension, drink or syrup. Formulations may also be presented as a bolus, electuary or paste. In some embodiments, solid dosage forms such as pills, cachets, tablets or capsules are used.

Excipients may be utilized to formulate the active ingredient (i.e., a desazadesferrithiocin analog, salt or polymorph) into tablets, capsules, suspensions, powders for suspension, granules, and the like. Excipients may include, without limitation, surfactants, pH modifiers, fillers, disintegrants, pigments, binders, lubricants, glidants, flavorants, colorants, preservatives, and any other conventional formulation excipients well-known in the art (e.g., as described in Remington: *The Science and Practice of Pharmacy* 2Qth ed. 2000). Such excipients may be used for customary purposes and in typical amounts without adversely affecting the properties of the compositions.

Examples of fillers, or diluents, include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Fillers may also be proprietary, such in the case of the filler PROSOLV® (available from JRS Pharma). PROSOLV is a proprietary, optionally high-density, silicified microcrystalline cellulose composed of 98% microcrystalline cellulose and 2% colloidal silicon dioxide. Silicification of the microcrystalline cellulose is achieved by a patented process, resulting in an intimate association between the colloidal silicon dioxide and microcrystalline cellulose. ProSolv comes in different grades based on particle size, and is a white or almost white, fine or granular powder, practically insoluble in water, acetone, ethanol, toluene and dilute acids and in a 50 g/l solution of sodium hydroxide.

Examples of disintegrants include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxy propyl cellulose, starch, pregelatinized starch, and sodium alginate.

Examples of lubricants include, without limitation, calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include, without limitation, silicon dioxide ($SiO_2$), talc cornstarch, and poloxamers. Poloxamers (or LUTROL®, available from the BASF Corporation) are A-B-A block copolymers in which the A segment is a hydrophilic polyethylene glycol homopolymer and the B segment is hydrophobic polypropylene glycol homopolymer.

Examples of tablet binders include, without limitation, acacia, alginiC acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

Examples of surfactants include, without limitation, fatty acid and alkyl sulfonates; commercial surfactants such as benzethanium chloride (HYAMINE® 1622, available from Lonza, Inc., Fairlawn, N.J.); DOCUSATE SODIUM® (available from Mallinckrodt Spec. Chem., St. Louis, Mo.); polyoxyethylene sorbitan fatty acid esters (TWEEN®, available from lCl Americas Inc., Wilmington, Del.; LIPOSORB® P-20, available from Lipochem Inc., Patterson N.J.; CAPMUL® POE-0, available from Abitec Corp., Janesville, Wis.), polyoxyethylene (20) sorbitan monooleate (TWEEN 80®, available from lCl Americas Inc., Wilmington, Del.); and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug Examples of drug complexing agents or solubilizers include, without limitation, the polyethylene glycols, caffeine, xanthene, gentisic acid and cylodextrins.

The addition of pH modifiers such as acids, bases, or buffers may also be beneficial, retarding or enhancing the rate of dissolution of the composition, or, alternatively, helping to improve the chemical stability of the composition.

Solid Dosage Forms

In some embodiments, oral formulations according to the invention are provided in solid dosage forms including, but not limited to, tablets, capsules (e.g., push-fit capsules made of gelatin, as well as soft, sealed capsules made of gelatin and a plasticizer, such as glycerol or sorbitol). Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds, salts and polymorphs may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In addition to various excipients described above, taste masking agents, preservatives, lubricants, stabilizers, bulking agents, flavorants and/or solubilizing agents are particularly useful for solid dosage forms.

Various solid dosage forms may have differing amounts of ingredients and differing ingredients as well. Typically, the total fill weight of all ingredients present in a solid dosage form is referred to as the strength of the solid dosage form. For example, the total fill weight of a tablet or capsule is typically referred to as the strength of the tablet or capsule. In some embodiments, the strength (i.e., the total fill weight) of a solid dosage form (e.g., tablet or capsule) may be at least about 50 mg, 100 mg, 150 mg, 200 mg, 250 mg, 300 mg, 325 mg, 350 mg, 375 mg, 400 mg, 425 mg, 450 mg, 475 mg, 500 mg or more. In some embodiments, the strength (i.e., the total fill weight) of a solid dosage form (e.g., tablet or capsule) may be or less than about 2000 mg, 1900 mg, 1800 mg, 1700 mg, 1600 mg, 1500 mg, 1400 mg, 1300 mg, 1200 mg, 1100 mg, 1000 mg, 900 mg, 800 mg, 700 mg, 600 mg, 500 mg, 400 mg, 300 mg, or 250 mg. In some embodiments, the strength (i.e., the total fill weight) of a solid dosage form (e.g., tablet or capsule) may range from about 50-1000 (e.g., from about 50-900 mg, 50-800 mg, 50-700 mg, 50-600 mg, 50-500 mg, 100-1000 mg, 100-900 mg, 100-800 mg, 100-700 mg, 100-600 mg, or 100-500 mg).

In some embodiments, the amount of the active ingredient (e.g., a desazadesferrithiocin analog, salt or polymorph) may constitute a substantial weight percentage of a solid dosage form. For example, the active ingredient (e.g., a desazadesferrithiocin analog, salt or polymorph) may constitute at least about 50%, 55%, 60%, 65%, 70%, 75%, 80%, 85%, 90%, 91%, 92%, 93%, 94%, 95%, 96%, 97%, 98%, 99%, or more of the total fill weight of a solid dosage form (e.g., tablet or capsule). Thus, as non-limiting examples, for a solid dosage form having a strength of about 200 mg, each solid dosage unit (e.g., tablet or capsule) may contain the active ingredient (e.g., a desazadesferrithiocin analog, salt or polymorph) at an amount of or greater than about 100 mg, 110 mg, 120 mg, 130 mg, 140 mg, 150 mg, 160 mg, 170 mg, 180 mg, 182 mg, 184 mg, 186 mg, 188 mg, 190 mg, 192 mg, 194 mg, 196 mg, 198 mg, or more. The amount of the active ingredient in solid dosage forms with different strength may be calculated similarly.

In some embodiments, a solid dosage form (e.g., tablet or capsule) typically contain an amount of the active ingredient that effects daily dose of at least about 10 mg/kg of body weight (e.g., at least about 12 mg/kg, 14 mg/kg, 16 mg/kg, 18 mg/kg, 20 mg/kg, 24 mg/kg, 28 mg/kg, 32 mg/kg, 34 mg/kg, 36 mg/kg, 38 mg/kg, 40 mg/kg, 45 mg/kg, 50 mg/kg, 55 mg/kg, 60 mg/kg, 65 mg/kg, 70 mg/kg, 75 mg/kg, 80 mg/kg of body weight); or a daily dose ranging from about 10-250 mg/kg of body weight (e.g., about 10-200 mg/kg, 10-150 mg/kg, 10-100 mg/kg, 16-250 mg/kg, 16-200 mg/kg, 16-150 mg/kg, 16-100 mg/kg, 16-80 mg/kg, 32-250 mg/kg, 32-200 mg/kg, 32-150 mg/kg, 32-100 mg/kg, 32-80 mg/kg, 40-250 mg/kg, 40-200 mg/kg, 40-150 mg/kg, 40-100 mg/kg, 40-80 mg/kg, 40-60 mg/kg of body weight). An actual amount of the active ingredient in each discrete dosage unit (e.g., each table or capsule) may be readily calculated based on the frequency of daily dosing (e.g., once daily, twice daily, etc.) and how many units (e.g., how many tables, capsules) are administered each time.

As non-limiting examples, a solid dosage form according to the present invention is a capsule that contains, by weight, at least 50% (e.g., 55%, 60%, 65%, 70%, 75%, 80%, 85%, 90%, 95%, or more) of (S)-4,5-Dihydro-2-[2-hydroxy-3-(3, 6,9-trioxadecyloxy)phenyl]-4-methyl-4-thiazolecarboxylate magnesium hydroxide (compound 1) or tromethamine 4'-desazadesferrithiocin polyether. In particular embodiments, a solid dosage form according to the present invention is a capsule that contains, by weight, 96% of (S)-4,5-Dihydro-2-[2-hydroxy-3-(3,6,9-trioxadecyloxy)phenyl]-4-methyl-4-thiazolecarboxylate magnesium hydroxide or tromethamine 4'-desazadesferrithiocin polyether. In some embodiments, a solid dosage form according to the present invention is a capsule that contains about 48 mg, 96 mg, 192 mg, 240 mg, 360 mg, or 480 mg of said (S)-4,5-Dihydro-2-[2-hydroxy-3-(3,6,9-trioxadecyloxy)phenyl]-4-methyl-4-thiazolecarboxylate magnesium hydroxide or tromethamine 4'-desazadesferrithiocin polyether.

In certain embodiments, a solid dosage form according to the present invention is a capsule that contains, by weight, about 0-99% (e.g., about 1-10%, 10-20%, 20-30%, 30-40%, 40-50%, 50-60%, 60-70%, 70-80%, 80-90%, or 90-99%) of (S)-4,5-Dihydro-2-[2-hydroxy-3-(3,6,9-trioxadecyloxy)phenyl]-4-methyl-4-thiazolecarboxylate magnesium hydroxide or tromethamine 4'-desazadesferrithiocin polyether.

In certain embodiments, a solid dosage form according to the present invention is a capsule that contains, by weight, about 0-99.8% (e.g., about 0-90%, 0-80%, 0-70%, 0-60%, 0-50%, 0-40%, 0-30%, 0-25%, 0-20%, 0-15%, 0-10%, 0-9%, 0-8%, 0-7%, 0-6%, 0-5%, 0-4%, 0-3%, 0-2%, 0-1%) of croscarmellose sodium.

In certain embodiments, a solid dosage form according to the present invention is a capsule that contains, by weight, about 0-10% (e.g., about 0-9%, 0-8%, 0-7%, 0-6%, 0-5%, 0-4%, 0-3%, 0-2%, 0-1%) of sodium starch glycolate. In certain embodiments, a solid dosage form according to the present invention is a capsule that contains, by weight, about 0-5% (e.g., about 0-4%, 0-3%, 0-2%, 0-1%) of magnesium stearate.

The present invention encompasses various combinations of the components described herein. As a non-limiting example, a solid dosage form according to the invention may be a capsule that contains, by weight, about 0.2-99% (e.g., about 10-99%, 20-99%, 30-99%, 40-99%, 50-99%, 60-99%, 70-99%, 80-99%) of (S)-4,5-Dihydro-2-[2-hydroxy-3-(3,6,9-trioxadecyloxy)phenyl]-4-methyl-4-thiazolecarboxylate magnesium hydroxide or tromethamine 4'-desazadesferrithiocin polyether; about 0-99.8% (e.g., about 0-90%, 0-80%, 0-70%, 0-60%, 0-50%, 0-40%, 0-30%, 0-20%, 0-10%, 0-5%, 0-4%, 0-3%, 0-2%, 0-1%) of croscarmellose sodium; about 0-10% (e.g., about 0-9%, 0-8%, 0-7%, 0-6%, 0-5%, 0-4%, 0-3%, 0-2%, 0-1%) of sodium starch glycolate; and about 0-5% (e.g., about 0-4%, 0-3%, 0-2%, 0-1%) of magnesium stearate.

As another non-limiting example, a solid dosage form according to the invention may be a capsule that contains, by weight, about 90-99% (e.g., about 90%, 91%, 92%, 93%, 94%, 95%, 96%, 97%, 98%, or 99%) of (S)-4,5-Dihydro-2-[2-hydroxy-3-(3,6,9-trioxadecyloxy)phenyl]-4-methyl-4-thiazolecarboxylate magnesium hydroxide or tromethamine 4'-desazadesferrithiocin polyether; about 1-5% (e.g., about 1%, 1.5%, 2%, 2.5%, 3%, 3.5%, 4%, 4.5%, or 5%) of croscarmellose sodium; and about 0.5-2% (e.g., about 0.5%, 1.0%, 1.5%, 2%) of magnesium stearate.

As yet another non-limiting example, a solid dosage form according to the invention may be a capsule that contains, by weight, 96% of (S)-4,5-Dihydro-2-[2-hydroxy-3-(3,6,9-trioxadecyloxy)phenyl]-4-methyl-4-thiazolecarboxylate magnesium hydroxide or tromethamine 4'-desazadesferrithiocin polyether; 3% of croscarmellose sodium; and 1% of magnesium stearate.

In some embodiments, croscarmellose sodium is NF Type A and said magnesium stearate is NF/EP Non-Bovine #5712. In some embodiments, a capsule has a fill weight (i.e., strength) of about 50 mg, 100 mg, 200 mg, 250 mg, 300 mg, 350 mg, 375 mg, 400 mg, 425 mg, 450 mg, 475 mg, or 500 mg.

Solid dosage forms described herein may be prepared using various methods. As a non-limiting example, a solid dosage form containing (S)-4,5-Dihydro-2-[2-hydroxy-3-(3,6,9-trioxadecyloxy)phenyl]-4-methyl-4-thiazolecarboxylate magnesium hydroxide, a filler, and a lubricant may be prepared using a process including the steps of: (a) screening said (S)-4,5-Dihydro-2-[2-hydroxy-3-(3,6,9-trioxadecyloxy)phenyl]-4-methyl-4-thiazolecarboxylate magnesium hydroxide using a 20 mesh screen; (b) screening said filler using a 20 mesh screen; (c) mixing said (S)-4,5-Dihydro-2-[2-hydroxy-3-(3,6,9-trioxadecyloxy)phenyl]-4-methyl-4-thiazolecarboxylate magnesium hydroxide and said filler; (d) screening said lubricant using a 20 mesh screen; (e) adding and mixing said lubricant; and (f) encapsulating the resulting mixture, e.g., into a capsule or tablet. In particular embodiments, said (S)-4,5-Dihydro-2-[2-hydroxy-3-(3,6,9-trioxadecyloxy)phenyl]-4-methyl-4-thiazolecarboxylate magnesium hydroxide is the Form A polymorph. A suitable filler is croscarmellose sodium, for example, NF Type A; a suitable lubricant is magnesium stearate, for example, NF/EP Non-Bovine #5712.

Several different types of coatings may be applied individually or in combination to the overall dosage form or particles, granules or beads that make up the dosage form. A functional coating, such as an enteric polymer, may be used, to prevent or retard dissolution until the dosage form leaves the stomach. Exemplary enteric coating materials include HPMCAS, HPMCP, CAP, CAT, carboxymethylethyl cellulose, carboxylic acid-functionalized polymethacrylates, and carboxylic acid-functionalized polyacrylates. Alternatively, a "non-functional" coating, such as a sugar-containing coating to facilitate swallowing, which does not substantially affect dissolution or other pharmacokinetic properties, may be used.

Solubility

Typically, oral formulations described herein facilitate solubilizing an active ingredient (e.g., a desazadesferrithiocin analog, salt or polymorph) at a desired amount or rate suitable for the treatment of metal overload. As used herein, the term "solubility" is generally intended to be synonymous with the term "aqueous solubility," and refers to the ability, and the degree of the ability, of a compound to dissolve in water or an aqueous solvent or buffer, as might be found under physiological conditions. Aqueous solubility is, in and of itself, a useful quantitative measure, but it has additional utility as a correlate and predictor, with some limitations which will be clear to those of skill in the art, of oral bioavailability. Typically, a soluble compound is generally desirable, and the more soluble, the better. In liquid formulations, solubility is typically reported in mg/mL, but other measures, such as g/g, may be used. Solubilities typically deemed acceptable may range from 1 mg/mL into the hundreds or thousands of mg/mL.

Solubility may be measured under varying conditions. For example, it may be measured under conditions similar to those found in the body, such as at gastric pH or at physiologic or near-physiologic pH. "Gastric pH" as used herein means about pH 1. "Near-physiologic pH," as used herein refers to the typical pH of bodily tissues and fluids, such as blood and plasma, or cytoplasm, generally about 7.4.

For solid dosage forms, dissolution rates can be used to assess the ability, and the degree of the ability, of an active compound within a solid formulation to dissolve into a solution, as might be found under physiological conditions.

Various dissolution assays are available such as those conducted per a standard USP, European Pharmacopoeia, British Pharmacopoeia protocol. For example, a suitable dissolution assay can be conducted in a dissolution medium which includes a phosphate buffer solution, pH 6.8 with 0.5% (v/v) Tween™ 80. In some embodiments, such a medium is prepared by dissolving 6.8 g of potassium phosphate monobasic and approximately 896 mg of sodium hydroxide in 1 L water. Confirm pH of 6.8+/−0.05. Adjust, if needed, with either phosphoric acid or sodium hydroxide. Dearate the medium with helium sparge. Add 5 mL of Tween 80 to an aliquot of the medium. Stir at, e.g., about 50, 60, 70, 80, 90, 100 or more RPM, until dissolved and reintroduce back into the carboy and mix well. Such dissolution medium may be scaled up as desired. In some embodiments, a Paddle method can be used to assess dissolution rates at 50 rpm in 900 ml of pH 6.0 buffer prepared with 0.01 mol/L sodium monohydrogenphosphate and 0.005 mol/L citric acid. In some embodiments, a solid dosage form according to the invention is characterized with a dissolution rate that results in greater than 10%, 15%, 20%, 25%, 30%, 35%, 40%, 45%, 50%, 55%, 60%, 65%, 70%, 75%, 80%, 85%, 90%, 95% or more of the active ingredient (e.g., a desazadesferrithiocin analog, salt or polymorph such as a compound of Formula I) dissolves in solution under 20, 30, 40, 50, or 60 minutes in a dissolution assay (e.g., a dissolution assay using a phosphate buffer solution, pH 6.8 with 0.5% (v/v) Tween 80, at 50 RPM) described herein or known in the art. In some embodiments, a solid dosage form according to the invention is characterized with a dissolution rate that results in greater than 50%, 55%, 60%, 65%, 70%, 75%, 80%, 85%, 90%, 95% of the active ingredient (e.g., the a desazadesferrithiocin analog, salt or polymorph such as a compound of Formula I) dissolves in solution under 30 minutes in a dissolution assay (e.g., a dissolution assay using a phosphate buffer solution, pH 6.8 with 0.5% (v/v) Tween 80, at 50 RPM) described herein or known in the art. In some embodiments, a solid dosage form according to the present invention is characterized with a dissolution rate that results in substantial disintegration under 30 minutes in a dissolution assay (e.g., a dissolution assay using a phosphate buffer solution, pH 6.8 with 0.5% (v/v) Tween 80, at 50 RPM) described herein or known in the art. In some embodiments, a solid dosage form according to the present invention is characterized with a dissolution rate that results in substantial disintegration under 60 minutes in a dissolution assay (e.g., a dissolution assay using a phosphate buffer solution, pH 6.8 with 0.5% (v/v) Tween 80, at 50 RPM) described herein or known in the art. As non-limiting examples, a capsule according to the present invention is characterized with a dissolution rate that results in about 7.3% to about 78.6% dissolved at 10 minutes, about 16.8% to about 95.8% dissolved at 20 minutes, about 25.0% to about 100% dissolved at 30 minutes, about 34.7% to about 100% dissolved at 45 minutes, and about 43.1% to about 100% dissolved at 60 minutes in a dissolution assay described herein (e.g., a dissolution assay using a phosphate buffer solution, pH 6.8 with 0.5% (v/v) Tween 80, at 50 RPM). As another non-limiting example, a capsule is at least 70% dissolved at 60 minutes in a dissolution assay described herein (e.g., a dissolution assay using a phosphate buffer solution, pH 6.8 with 0.5% (v/v) Tween 80, at 50 RPM).

Stability

Typically, formulations according to the present invention are capable of stabilizing, or alternatively slowing or preventing the degradation, of an active ingredient formulated therewith (i.e., a desazadesferrithiocin analog, salt or polymorph). As used herein, the term "stable" refers to the ability of the active ingredient (i.e., a desazadesferrithiocin analog, salt or polymorph) to maintain its therapeutic efficacy (e.g., all or the majority of its intended biological activity and/or physiochemical integrity) over extended periods of time. The stability of an active ingredient, and the capability of a formulation to maintain stability of such active ingredient, may be assessed over extended periods of time (e.g., preferably for at least 1, 3, 6, 12, 18, 24, 30, 36 months or more). In the context of a formulation, a stable formulation is one in which the active ingredient therein essentially retains its physical and/or chemical integrity and biological activity upon storage and during processes. For example, stability at a given time point may be compared against stability at an earlier time point (e.g., upon formulation day 0) or against unformulated compound and the results of this comparison expressed as a percentage. Preferably, a formulation of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the active's biological activity or physiochemical integrity over an extended period of time (e.g., as measured over at least about 6-12 months, at room temperature or under accelerated storage conditions).

In some embodiments, if formulations are provided in solid dosage forms, the stability can also be measured by the change of water content (i.e., moisture content) over extended periods of time (e.g., preferably for at least 1, 3, 6, 12, 18, 24, 30, 36 months or more). For example, a desired solid dosage form (e.g., capsule or tablet) of the present invention maintain at least 100%, at least 99%, at least 98%, at least 97% at least 95%, at least 90%, of the water content over an extended period of time (e.g., as measured over at least about 6-12 months, at room temperature or under accelerated storage conditions). In some embodiments, the change (i.e., increase or decrease) of water content of a desired solid dosage form (e.g., capsule or tablet) of the present invention is no greater than about 10%, 9%, 8%, 7%, 6%, 5%, 4%, 3%, 2%, 1%, 0.5%, or less over an extended period of time (e.g., as measured over at least about 6-12 months (e.g., 6, 7, 8, 9, 10, 11, or 12 month), at room temperature or under accelerated storage conditions). As a non-limiting example, a capsule of the invention has an increase in moisture content of less than about 10% over an 12-month period. As another non-limiting example, a capsule of the invention has an increase in moisture content of less than about 2% over an 12-month period.

Immediate Vs. Controlled Release

Various formulations described herein may be formulated for immediate or controlled/slow release.

In some embodiments, formulations may be provided in a controlled release dosage form. In one such dosage form, the composition of the drug and polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the particles of low-solubility drug that are at least partially coated with a precipitation-inhibiting polymer. The aqueous-swollen matrix gradually erodes, swells, disintegrates or dissolves in the environment of use, thereby controlling the release of the drug mixture to the environment of use.

Alternatively, compounds may be administered by or incorporated into a non-erodible matrix device.

Alternatively, compounds may be delivered using a coated osmotic controlled release dosage form. This dosage form has two components: (a) the core which contains an osmotic agent and the coated compound particles; and (b) an outer coating surrounding the core, the outer coating controlling the influx of water to the core from an aqueous environment of use so as to cause compound release by extrusion of some or all of the core to the environment of use. The osmotic agent contained in the core of this device may be an aqueous-swellable hydrophilic polymer, hydrogel, osmogen, or osmagent. The outer coating surrounding the core is preferably polymeric, aqueous-permeable, and has at least one delivery port.

Alternatively, compounds may be delivered via a coated hydrogel controlled release dosage form having three components: (a) a compound-containing composition containing the coated compound particles, (b) a water-swellable composition wherein the water-swellable composition is in a separate region within a core formed by the compound-containing composition and the water-swellable composition, and (c) an outer coating around the core that is water-permeable, and has at least one delivery port therethrough. In use, the core imbibes water through the outer coating, swelling the water-swellable composition and increasing the pressure within the core, and fluidizing the compound-containing composition. Because the outer coating surrounding the core remains intact, the compound-containing composition is extruded out of the delivery port into an environment of use.

Provided herein is for compositions having controlled release of at least a portion of the compound contained in the dosage form over a sustained length of time. Such an embodiment may have utility where it is desired to release at least a portion of the compound in a target organ such as the stomach, the small intestine, the colon, or any combination of these. In this embodiment, the compound may be coated with an enteric, precipitation-inhibiting polymer. Preferred enteric precipitation-inhibiting polymers include HPMCAS, CAP, CAT, HPMCP, and CMEC. The compound particles may be fully encapsulated with the precipitation-inhibiting polymer to prevent early dissolution of the compound in a gastric environment. The precipitation-inhibiting polymer may be water impermeable at low pH to prevent the compound from dissolving and leaching out of the dosage form in the gastric environment. This embodiment has particular utility for providing controlled release of low-solubility, basic compounds to the small intestine or colon.

Alternatively, compounds may be delivered via a rapid-melt or rapidly disintegrating tablet, for the purpose of enhancing delivery across mucosal membranes. Additional optional excipients for such a dosage form might include effervescent agents or taste-masking agents. Such a dosage form would be deliverable buccally or sublingually, and might find use where improved bioavailability or accelerated the onset of action of some active drug ingredients is desired.

In addition to the above additives, excipients, and processes, use of any conventional materials and procedures for preparation of suitable dosage forms using the compositions disclosed herein known by those skilled in the art are potentially useful.

Other Types of Formulations

In some embodiments, the compounds, salts and polymorphs described herein may also be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds, salts and polymorphs which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds, salts and polymorphs to allow for the preparation of highly concentrated solutions.

In addition to the formulations described previously, a compound, salt, or polymorph as disclosed herein may also be formulated as a depot preparation. Such long acting formulations may be administered by implantation (for example subcutaneously or intramuscularly) or by intramuscular injection. Thus, for example, the compounds, salts and polymorphs may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds, salts and polymorphs may also be formulated in rectal compositions such as suppositories or retention enemas, e.g., containing conventional suppository bases such as cocoa butter, polyethylene glycol, or other glycerides.

Certain compounds, salts and polymorphs disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds, salts and polymorphs may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds, salts and polymorphs disclosed herein may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Intranasal delivery, in particular, may be useful for delivering compounds to the CNS. It had been shown that intranasal drug administration is a noninvasive method of bypassing the blood-brain barrier (BBB) to deliver neurotrophins and other therapeutic agents to the brain and spinal cord. Delivery from the nose to the CNS occurs within minutes along both the olfactory and trigeminal neural pathways. Intranasal delivery occurs by an extracellular route and does not require that drugs bind to any receptor or undergo axonal transport. Intranasal delivery also targets the nasal associated lymphatic tissues (NALT) and deep cervical lymph nodes. In addition, intranasally administered therapeutics are observed at high levels in the blood vessel walls and perivascular spaces of the cerebrovasculature. Using this intranasal method in animal models, researchers have successfully reduced stroke damage, reversed Alzheimer's neurodegeneration, reduced anxiety, improved memory, stimulated cerebral neurogenesis, and treated brain tumors. In humans, intranasal insulin has been shown to improve memory in normal adults and patients with Alzheimer's disease. Hanson L R and Frey W H, $2^{nd}$, *J Neuroimmune Pharmacol.* 2007 March; 2(1):81-6. Epub 2006 Sep. 15.

Typically, unit dosage formulations contain an effective dose of the active ingredient. Effective doses of the active ingredient described in connection with oral formulations may be adapted for other types of formulations.

The amount of active ingredient that may be combined with the carrier materials to produce a single dosage form will vary depending upon the host treated and the particular mode of administration. Preferred unit dosage formulations are those containing an effective dose, as herein described, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Pharmacokinetics, Pharmacodynamics, and Bioavailability

Among other things, formulations, in particular, oral formulations, described herein provides unexpectedly superior pharmacokinetics, pharmacodynamics and bioavailability. The following standard abbreviations are used to represent the associated pharmacokinetic parameters.

$AUC_{inf}$ Area under the plasma concentration versus time curve up to the last measurable concentration plus the AUC, calculated using the linear trapezoidal rule from the zero time point to the last quantifiable concentration and extrapolated from the last measurable concentration ($C_{last}$ at $t_{last}$) to infinity: $AUC_{INFobs}=AUC_{0-tlast}+C_{last}/$ Lambda z (where λz is the first order rate constant associated with the terminal (log-linear) portion of the curve)

$AUC_{0-12}$ Area under the curve between the time of dose and the 12 h time point $AUC_{0-24}$ Area under the curve between the time of dose and the 24 h time point F Fraction available (bioavailability):
$F=[AUC_{oral}]\cdot dose_{iv}/[AUC_{iv}]\cdot dose_{oral}$ CL Clearance CLr Renal clearance, calculated for the 24-hour steady-state period according to $$CL_r = \frac{Ue(0\text{-}24)}{AUC(0\text{-}24)}$$

Where Ue is excreted drug

Cl/F Apparent total body clearance as a function of bioavailability $$CL/F = \frac{\text{Dose}}{AUC(0\text{-}24)}$$

$V_{ss}$ Steady state volume of distribution $V_d$ Volume of distribution $V_z$/F Apparent terminal phase volume of distribution as a function of bioavailability $$Vz/F = \frac{\text{Dose}}{\lambda z \times AUC(0\text{-}24)}$$

$t_{1/2}$ Terminal half-life ($HL_{\lambda z}$), calculated by the equation $t\frac{1}{2}=0.693/k_{el}$ $C_{max}$ The maximum observed concentration, obtained directly from the plasma concentration time profile $T_{max}$, The time of $C_{max}$; at more than one time point, the first is chosen Λz elimination rate constant, calculated as the negative of the slope of the terminal log-linear segment of the plasma concentration-time curve, where slope is determined from a linear regression of the natural logarithm of the terminal plasma concentrations against time; at least 3 terminal plasma concentration time points, beginning with the final concentration≥LOQ, will be selected for the determination of λz and the regression will need coefficient of determination ($r^2$)≥0.9000.

$k_{el}$ The terminal elimination rate constant will be obtained from the slope of the line, fitted by linear least squares regression, through the terminal points of the log(base e) concentration-time profiles.

In general, an active ingredient (e.g., a compound of formula I or a salt or polymorph thereof) delivered using a formulation according to the present invention has sufficiently long half-time in serum. In some embodiments, an active ingredient (e.g., a compound of formula I or a salt or polymorph thereof) delivered using a formulation according to the present invention may have a half-life of at least approximately 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or longer. In some embodiments, an active ingredient (e.g., a compound of formula I or a salt or polymorph thereof) delivered using a formulation according to the present invention may have a half-life ranging between about 6 and about 24 hours (e.g., between about 6 and about 20 hours, between about 6 and about 18 hours, between about 8 and about 24 hours, between about 8 and about 22 hours, between about 10 and about 24 hours, between about 10 and about 22 hours, between about 10 and about 20 hours, between about 12 and about 24 hours, between about 12 and about 22 hours, or between about 12 and about 20 hours).

In some embodiments, an active ingredient (e.g., a compound of formula I or a salt or polymorph thereof) delivered according to the present invention may retain detectable level or activity in bloodstream after 4 hours, 6 hours, 8 hours, 10 hours, 12 hours, 14 hours, 16 hours, 18 hours, 20 hours, 22 hours, 24 hours, 30 hours, 36 hours, 42 hours, 48 hours, or longer following administration. Detectable level or activity for metal chelation may be determined using various methods known in the art.

Typically, formulations described herein facilitate rapid distribution of an active ingredient (e.g., a compound of formula I or a salt or polymorph thereof) to the blood stream. For example, an active ingredient (e.g., a compound of formula I or a salt or polymorph thereof) delivered according to the present invention may reach the maximum concentration in serum ($C_{max}$) within about 30, 40, 50, 60, 70, 80, 90, 100, 110, or 120 minutes following oral administration.

In some embodiments, formulations described herein, once administered regularly at an administration interval, results in maximum serum concentration ($C_{max}$) of the active ingredient within a range from approximately 60 to about 150 μg/mL (e.g., approximately 60-140 μg/mL, 60-130 μg/mL, 60-120 μg/mL, 60-110 μg/mL, 60-100 μg/mL, 70-150 μg/mL, 70-140 μg/mL, 70-130 μg/mL, 70-120 μg/mL, 70-110 μg/mL, 70-100 μg/mL, 80-150 μg/mL, 80-140 μg/mL, 80-130 μg/mL, 80-120 μg/mL, 80-110 μg/mL, 80-100 μg/mL).

In some embodiments, formulations described herein, once administered regularly at an administration interval, results in serum $AUC_{inf}$ of the active ingredient within a range from approximately 120 to about 400 μg·h/mL (e.g., approximately 120-350 μg·h/mL, 120-300 μg·h/mL, 120-250 μg·h/mL, 120-200 μg·h/mL, 150-400 μg·h/mL, 150-350 μg·h/mL, 150-300 μg·h/mL, 150-250 μg·h/mL, 180-400 μg·h/mL, 180-350 μg·h/mL, 180-300 μg·h/mL, 180-250 μg·h/mL, 200-400 μg·h/mL, 200-350 μg·h/mL, 200-300 μg·h/mL).

Without wishing to be bound by particular theory, it is contemplated that the superior pharmacokinetics, pharmacodynamics and bioavailability provided by formulations of the present invention permits effective treatment of metal overload by single daily dose. For example, various daily doses described herein may be provided in a single dose.

However, the present invention is not limited to single daily dosing. For example, various daily doses described herein may be provided in two or more separate doses. In some embodiments, two separate doses are used. In some embodiments, the two separate doses are divided equally. In some embodiments, the doses are divided such that at least 75% of the total daily amount is delivered in the first dose, and the remainder in the second dose. In some embodiments, the doses are given at least 6, 8 or 12 hours apart.

Treatment of Metal Overload

Inventive formulations described herein may be used to effectively treat metal overload. As used herein, the term "metal overload" refers to a condition in which the body has reached its limit to absorb and excrete a particular metal, resulting in an excess amount of the metal accumulated in various tissues inside the body that lead to toxicity or other pathological conditions. Inventive formulations described herein may be used to chelate, sequester, reduce, or eliminate such accumulated metals including, but not limited to, iron, heavy metals (e.g., $Hg^{2+}$), uranium, and other radioactive isotopes such as lanthanide and actinide series. As used herein, the term "treat," "treatment," or "treating" refers to any method used to reduce metal levels (e.g., iron levels) as compared to a baseline control level and/or partially or completely alleviate, ameliorate, relieve, inhibit, prevent, delay onset of, reduce severity of and/or reduce incidence of one or more symptoms or features of a disease, disorder, and/or condition associated with metal overload.

Iron Overload

In some embodiments, the present invention provides methods to treat iron overload. As used herein, the term "iron overload" refers to a condition in which an excess amount of iron accumulate inside a body that leads to toxic or other pathological conditions. Without wishing to be bound by theory, iron overload can be toxic in part through the generation by iron of reactive oxygen species such as $H_2O_2$. In the presence of $Fe^{2+}$, $H_2O_2$ is reduced to the hydroxyl radical (HO.), a highly reactive species, a process known as the Fenton reaction. The hydroxyl radical reacts very quickly with a variety of cellular constituents and can initiate free radicals and radical-mediated chain processes that damage DNA and membranes, as well as produce carcinogens.

Typically, under normal conditions, iron absorption and loss are balanced at about 1 mg/day. Iron overload can be caused by repeated blood transfusion (i.e., transfusional iron overload) or increased iron absorption required in patients suffering from various congenital and acquired anemias. Exemplary causes of anaemia include, but are not limited to, β-thalassemia-major, non-transfusion dependent Thalassaemia (NTDT) such as β-thalassemia-intermedia, Blackfan-Diamond anemia, Sideroblastic anemia, sickle cell disease, aplastic anemia, red cell aplasia, Myelodysplasia (MDS), chronic myelofibrosis, paroxysmal nocturnal hemoglobinuria.

Typically, transfused blood contains 200-250 mg of iron per unit. Hence, patients with β-thalassemia major (TM) or other refractory anemias receiving 2-4 units of blood per month have an annual intake of 5000-10,000 mg of iron or 0.3-0.6 mg/kg per day.

Thus, in some embodiments, iron overload refers to a condition under which a subject has an iron intake greater than 1 mg/day, 5 mg/day, 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day or 100 mg/day. In some embodiments, iron overload refers to a condition under which a subject has an iron intake greater than 0.1 mg/kg per day, 0.2 mg/kg per day, 0.3 mg/kg per day, 0.4 mg/kg per day, 0.5 mg/kg per day, 0.6 mg/kg per day, 0.7 mg/kg per day, 0.8 mg/kg per day, or more. In some embodiments, iron overload refers to a condition under which a subject has an iron intake of approximately 0.1 to 0.7 mg/kg per day. In some embodiments, iron overload refers to a condition under which a subject has an iron intake of approximately 0.2 to 0.6 mg/kg per day.

In some embodiments, iron overload refers to a condition under which a subject has an iron intake of approximately 0.2 to 0.5 mg/kg per day, for example, approximately 0.25 to 0.5 mg/kg per day, approximately 0.25 to 0.45 mg/kg per day, approximately 0.25 to 0.4 mg/kg per day, approximately 0.25 to 0.35 mg/kg per day, approximately 0.3 to 0.5 mg/kg per day, approximately 0.3 to 0.45 mg/kg per day, approximately 0.3 to 0.4 mg/kg per day, approximately 0.35 to 0.5 mg/kg per day, approximately 0.35 to 0.45 mg/kg per day. In certain embodiments, iron overload refers to a condition under which a subject has an iron intake of approximately 0.2 mg/kg per day, 0.25 mg/kg per day, 0.3 mg/kg per day, 0.35 mg/kg per day, 0.4 mg/kg per day, 0.45 mg/kg per day, 0.5 mg/kg per day.

Without effective treatment, iron overload may cause iron levels progressively increases with deposition in various tissues including, but not limited to, the liver, heart, pancreas, and other endocrine organs. Iron accumulation may also produce (i) liver disease that may progress to cirrhosis and hepatocellular carcinoma, (ii) diabetes related both to iron-induced decreases in pancreatic β-cell secretion and increases in hepatic insulin resistance and (iii) heart disease. Iron overload is also known to facilitated microbial infection in vertebrates by different strains of fungi, protozoa, gram positive, gram negative and acid-fast bacteria. This condition also facilitates viral infections in humans. Iron overload in humans is known to change the chemotactic and phagocytic properties of neutrophils, which leads to the reduction of their ability to kill invading pathogens. The T-cell function is also affected by these high concentrations of iron.

Formulations according to the present invention may be used to treat various iron overload conditions including, but not limited to, iron overload resulted from red blood cells chronic transfusion (necessary in conditions such as beta thalassemia major or intermedia, and other anemias including but not limited to non-transfusion dependent Thalassaemia (NTDT—i.e. patients with clinically milder forms of thalassemia, such as β-thalassemia intermedia, α-thalassemia (HbH disease), and HbE/β-thalassemia, who require occasional or no blood transfusions), Blackfan-Diamond anemia, Fanconi's anemia and other inherited bone marrow failure syndromes, Sideroblastic anemia, congenital dyserythropoietic anemias, sickle cell disease, pyruvate kinase deficiency (and other red cell enzyme deficiency causing hemolytic anemia), aplastic anemia, refractory anemias, red cell aplasia, Myelodysplasia (MDS), chronic myelofibrosis, paroxysmal nocturnal hemoglobinuria); from increased absorption of dietary iron (in conditions such as hereditary hemochromatosis and porphyria cutanea tarda); from mal-distribution or redistribution of iron in the body (e.g., resulted from conditions such as atransferrinemia, aceruloplasminemia, and Fredreich's ataxia); from transfusional iron overload from off-therapy leukemias, before and after bone marrow transplant and myelodysplastic syndrome; from diabetes or obesity; and/or from liver diseases (e.g., hepatitis).

In some embodiments, formulations of the present invention may be used to treat a microbial infection by a strain whose growth is stimulated by the presence of excess iron in body fluids, cells, tissues or intact vertebrate hosts. In various embodiments, formulations of the present invention may be used to treat a microbial infection by a strain whose growth is stimulated by the presence of iron selected from the group consisting of *Aspergillus, Candida, Cryptococcus, Histoplasma, Mucor, Paracoccidiodes, Pneumocystis, Pythium, Rhizopus, Trichosporon, Entamoeba, Leishmania, Naegleria, Plasmodium, Toxoplasma, Trichomonas, Tritrichomonas, Trypanasoma, Bacillus, Clostridium, Corynebacterium, Erysipelothrix, Listeria, Mycobacterium, Staphylococcus, Streptococcus, Tropheryma, Acinetobacter, Aeromonas, Alcaligenes, Campylobacter, Capnocytophaga, Chlamydia, Coxiella, Ehrlichia, Enterobacter, Escherichia, Helicobacter, Klebsiella, Legionella, Moraxella, Neisseria, Pasteurella, Proteus, Pseudomonas, Salmonella, Shigella, Vibrio,* and *Yersinia* in a patient suffering from iron overload. The administration of the formulation of the present invention results in the reduction of the excess iron body fluids, cells, tissues or intact infected hosts decreasing the growth and replication of the infecting microbial organism.

In various embodiments, formulations of the present invention may be used to treat acute iron toxicity from ingestion or infusion of iron; to reduce total body iron secondary to transfusion or excess iron dietary absorption; and/or for maintenance of iron balance after total body iron has been satisfactorily reduced and only excess daily transfusional or dietary iron needs to be excreted. Thus, in some embodiments, administration of a formulation described herein results in excretion between 0.2 and 0.5 mg Fe/kg body weight of the patient per day (e.g., about 0.2, 0.3, 0.4, or 0.5 mg Fe/kg body weight of the patient per day). In some embodiments, this amount of excretion is recommended for chronic iron overload secondary to transfusion. In some embodiments, administration of a formulation described herein results in excretion between 0.25-0.5 mg Fe/kg/d of patient body weight (e.g., about 0.25, 0.30, 0.35, 0.40, 0.45, 0.50 mg Fe/kg body weight of the patient per day). In some embodiments, this amount of excretion is recommended to achieve iron balance neutrality and/or for maintenance treatment.

In some embodiments, the efficacy of treatment according to the present invention may be measured by iron-clearing efficiency. As used herein, the term "iron-clearing efficiency (ICE)" refers to the molar efficiency or efficaciousness of a given dose or concentration of chelator in clearing iron from the body or one of its tissues, organs or parts. Efficaciousness in turn concerns quantity of iron removed from a target system (which may be a whole body, an organ, a tissue or other) in a unit of time. Iron clearing efficiency (ICE) is calculated by subtracting total iron excretion before treatment from total iron excreted after treatment and dividing that value by the theoretical amount of iron that could have been bound by the dose of chelator administered times 100.

In some embodiments, measurement of certain markers will be used as a proxy to assess therapeutic efficacy. In iron overload diseases, for example, the free iron species, non-transferrin-bound iron (NTBI), and labile plasma iron (LPI, also called redox-active iron) in the circulation, and the labile and chelatable iron pool within the cells, are responsible for iron toxicity through the generation of reactive oxygen species. The characteristic features of advanced iron overload are dysfunction and failure of vital organs such as liver and heart in addition to endocrine dysfunctions. For the estimation of body iron, there are direct and indirect methods available. See, e.g., Kohgo Y "Body iron metabolism and pathophysiology of iron overload," *Int J Hematol.,* 2008 88(1): 7-15 (epub 2008 Jul. 2); Angelucci E et al. "Hepatic Iron Concentration and Total Body Iron Stores in Thalassemia Major," *NEJM,* 2000 343(5): 327-331.

In some embodiments, measurement of serum ferritin can be used for monitoring efficacy. Ferritin is a globular cytoplasmic protein consisting of 25 heterodimeric subunits of H and L that stores iron as ferric hydroxide phosphate in a controlled manner, which may be found in the plasma in low concentration. By quantitative phlebotomy, it has been demonstrated that serum ferritin (SF) correlates with total body iron stores. However, the level of SF may be affected by acute and chronic inflammation and infections. There is also a difference between the standard values of SF concentration in males and females (normal range 10-220 µg/L in males; 10-85 µg/L in females). Therefore, data should be interpreted carefully when using SF as a biological marker for evaluation of body iron stores. Clinically, in order to detect organ dysfunctions, serum ferritin determinations should be conducted once every 1-3 months. According to the guidelines of the International MDS Symposium, 1,000 µg/L represents the threshold of the target SF value at which iron chelation therapy should be initiated in patients with transfusion iron overload. When serum ferritin levels exceed 1,500 μg/L, patients should be examined for the symptoms of cardiac failure or arrhythmias, and periodical cardiac echograms may also be useful in diagnosis. The concentration of heart iron is increased when SF levels become greater than 1,800 μg/L, and the prevalence of cardiac events is significantly increased when SF levels are more than 2,500 μg/L.

The present disclosure recognizes that even serum ferritin levels greater than 500 μg/L can be cause for iron chelation therapy. Thus, in some embodiments, the present invention may be used to treat a subject that has a serum ferritin level greater than about 500 μg/L (e.g., greater than about 600 μg/L, 700 μg/L, 800 μg/L, 900 μg/L). In some embodiments, the present invention may be used to treat a subject that has a serum ferritin level greater than about 1,000 μg/L (e.g., greater than about 1,200 μg/L, 1,500 μg/L, 1,800 μg/L, 2,000 μg/L, 2,200 μg/L, or 2,500 μg/L). In various embodiments, administration of a formulation according to the present invention results in reduction of serum ferritin level in the subject as compared to a baseline control. In some embodiments, administration of a formulation according to the present invention results in the serum ferritin level in the subject being treated below about 1,000 μg/L (e.g., below about 900 μg/L, 800 μg/L, 700 μg/L, 600 μg/L, or 500 μg/L).

An alternate method of assessing iron level in the body is via the measurement of labile plasma iron, a redox active form of non-transferrin bound iron that is chelatable, making it potentially available for transport into extrahepatic tissues. LPI can be accurately and reproducibly assayed by fluorescent method; see, e.g., Esposito B P et al., "Labile plasma iron in iron overload: redox activity and susceptibility to chelation," *Blood*, 2003, 102(7):2670-7 (Epub 2003 Jun. 12) and Wood, J C et al., "Relationship between labile plasma iron, liver iron concentration and cardiac response in a deferasirox monotherapy trial," *Haematologica*, 2011 96(7): 1055-1058 (epub 2011 Mar. 10). LPI measurements may be influenced by antioxidant and iron-binding activities of sera. Since LPI measurements are performed on intact serum or plasma, they should represent the sum of the pro-oxidant potential of the chelatable iron and the antioxidant activity of the sample. The total antioxidant activity of human plasma/serum has been estimated in the range of 1 mM and can be influenced by a variety of factors including diet and clinical conditions. Therefore, it is possible that sera containing similar concentrations of NTBI might have different levels of LPI, due to masking by antioxidants. It has also been suggested that chronic control of circulating LPI may be an important goal for iron chelation therapy in order to prevent oxidative damage, and to lower the risk of extrahepatic organ dysfunction.

Alternatively, iron concentration in a target organ or tissue may be measured directly. The measurement of liver iron concentration (LIC) by liver biopsy has traditionally been viewed as the most reliable means to assess body iron storage. The LIC level may also be determined by magnetic resonance imaging (MRI). The liver is the most important organ for iron storage with the largest capacity to sequester excess iron. In patients with β-thalassemia, the risk of organ dysfunction is increased when LIC values are greater than 7 mg/g (liver, dry weight), and LIC levels of over 15 mg/g (liver, dry weight) increase the risk of early cardiac death due to iron deposition in the myocardium. Studies in the deferasirox clinical development program in β-thalassemia also demonstrated a correlation between the reduction in LIC and SF values (R=0.63). In some embodiments, the present invention may be used to treat a subject that has an LIC level greater than about 7 mg/g (liver, dry weight) (e.g., greater than about 8, 9, 10, 11, 12, 13, 14, or 15 mg/g (liver, dry weight)). In some embodiments, the present invention may be used to treat a subject that has an LIC level greater than about 1 mg/g (liver, dry weight) (e.g., greater than about 2, 3, 4, 5, or 6 mg/g (liver, dry weight)). In some embodiments, administration of a formulation according to the present invention results in reduction of the LIC level in the subject as compared to a baseline control. In some embodiments, administration of a formulation according to the present invention results in the LIC level in the subject being treated below about 7 mg/g (liver, dry weight) (e.g., below about 6, 5, 4, 3, or 2 mg/g (liver, dry weight)).

The determination of cardiac iron concentration is clinically important because one of the major causes of death in iron overload is sudden cardiac arrest. Additionally, pancreatic beta cells are another important target of iron toxicity, which cause glucose intolerance and diabetes mellitus.

Recently, physical detection methods using magnetic resonance imaging (MRI) and superconducting quantum interference devices (SQUID) have become available to indirectly estimate iron concentration in liver, pancreas, and myocardium. In some embodiments, the cardiac iron level may be measured by MRI $R2^*$ or $T2^*$MRI. It has been reported that a shortening of myocardial $T2^*$ to less than 20 ms (implying increased myocardial iron above normal) is associated with an increased likelihood of decreased left ventricular ejection fraction (LVEF), whereas patients with $T2^*$ values greater than 20 ms have a very low likelihood of decreased LVEF. In some embodiments, the present invention may be used to treat a subject that has a myocardial $T2^*$ value less than about 20 ms (e.g., less than about 18, 16, 14, 10, 8, 6, 4, 2 ms). In some embodiments, administration of a formulation according to the present invention results in the reduction of cardiac iron level in the subject as compared to a baseline control. In some embodiments, the administration of a formulation according to the present invention results in myocardial $T2^*$ value greater than about 20 ms.

Appropriate baseline controls described herein (e.g., for serum ferritin, LIC, and/or cardiac iron level) are indicative of the pre-treatment levels in the corresponding tissues.

The subject (also referred to as "patient" or "individual") being treated can be a child, adolescent, or adult human. Besides being useful for human treatment, certain compounds and formulations disclosed herein may also be useful for veterinary treatment of companion animals, exotic animals and farm animals, including mammals, rodents, and the like. More preferred animals include horses, dogs, and cats.

As shown in the Examples below, the administration of a formulation according to the present invention results in no substantial adverse effects in subjects being treated even at a high dose (e.g., at or above about 40 mg/kg body weight per day) without titration. As used herein, no substantial adverse effects typically refers to no clinically apparent toxic effects on the kidney, bone marrow, thymus, liver, spleen, heart or adrenal glands. In some embodiments, substantial adverse effects do not include headaches, elevated transaminases, flatulence, chromaturia, and/or upper abdominal pain. In various embodiments, formulations described herein are well tolerated by the subject to whom such formulations are administered.

Thus, the initial daily dose for the treatment may start at any suitable doses. For example, the initial daily dose may be at least 10 mg/kg of body weight, 16 mg/kg of body weight, 20 mg/kg of body weight, 30 mg/kg of body weight, 40 mg/kg of body weight, or higher.

In some embodiments, the daily dose may be adjusted based on various markers such as, for example, LIC level, cardiac iron level, serum ferritin level and/or serum creatinine in the subject. In some embodiments, a method according to the invention may include two dose levels, the initial dose and a maintenance dose. Typically, the initial dose may be higher than the maintenance dose. In some embodiments, the initial dose may be lower than the maintenance dose. In some embodiments, daily dose may be repeated or skipped depending on the LIC level, cardiac iron level, serum ferritin level and/or serum creatinine in the subject being treated. For example, instead of daily dosing, a subject may be dosed twice a day, three times a day, four times a day, once every two days, twice a week, once a week, once every two weeks, twice a month, once every three weeks, once a month, once every two months, or at variable intervals. In some embodiments, the dose is once daily. In some embodiments, the dose is twice daily. In some embodiments, the dose is three times a day. In some embodiments, the dose is four times a day.

Combination Therapy

In some embodiments, formulations provided herein for treating diseases, disorders or conditions relating to metal toxicity or overload in a human or animal subject in need of such treatment can be used in combination with one or more additional agents that are beneficial for the treatment of such diseases, disorders or conditions and/or can reduce side effects.

In certain instances, it may be appropriate to administer a formulation described herein in combination with supplements of essential trace minerals required by the body for proper functioning, for example zinc and magnesium, to replace those which will inadvertently be lost to chelation therapy. Or, by way of example only, the therapeutic effectiveness of a formulation described herein may be enhanced by co-administration of an adjuvant (i.e., by itself the adjuvant may only have minimal therapeutic benefit, but in combination with another therapeutic agent, the overall therapeutic benefit to the patient is enhanced). Or, by way of example only, the benefit of a formulation described herein may be enhanced with another therapeutic agent (which also includes a therapeutic regimen) that also has therapeutic benefit for treating metal overload. By way of example only, in a treatment for thalassemia involving administration of a formulation described herein, increased therapeutic benefit may result by also providing the patient with another therapeutic agent for thalassemia, for example deferoxamine. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain formulations as disclosed herein with: deferasirox, deferiprone, deferoxamine, DTPA (diethylene triamine pentaacetic acid), EGTA (ethylene glycol tetraacetic acid), EDTA (ethylenediamine tetraacetic acid), DMSA (dimercaptosuccinic acid), DMPS (dimercapto-propane sulfonate), BAL (dimercaprol), BAPTA (aminophenoxyethane-tetraacetic acid), D-penicillamine, and alpha lipoic acid.

In various embodiments, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneously, the timing between the multiple doses may be any duration of time ranging from a few minutes to weeks.

Example 1

Synthesis of (S)-4,5-Dihydro-2-[2-hydroxy-3-(3,6,9-trioxadecyloxy)phenyl]-4-methyl-4-thiazolecarboxylate magnesium hydroxide (Compound 1)

Step 1: Synthesis of Ts-TEG

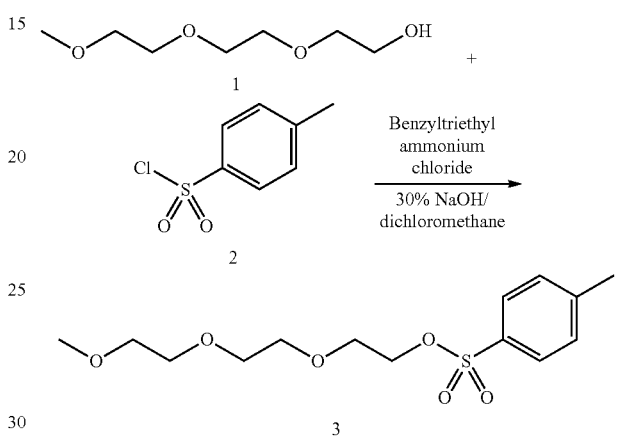

A 300 gallon glass lined reactor was charged with p-toluene sulfonyl chloride (2) and methylene chloride. A second 300 gallon glass lined reactor was charged with USP water, sodium hydroxide, methylene chloride, triethyleneglycol monomethyl ether (TEG) (1), and benzyltriethyl ammonium chloride. The p-toluene sulfonyl chloride solution was slowly added over 2 hours to the TEG solution while maintaining a temperature of 0-25° C. The reaction mixture was agitated for 1 hour and sampled for reaction completion analysis by HPLC. The product was isolated by separating the methylene chloride layer (product layer) from the aqueous layer. The organic layer was washed twice with water and the methylene chloride was replaced with toluene by vacuum distillation to yield 2-(2-(2-methoxyethoxy)ethoxy)ethyl 4-methylbenzenesulfonate (Ts-TEG) (3).

Step 2: Synthesis of sodium 2-cyano-6-(2-(2-(2 methoxyethoxy)ethoxy)ethoxy) phenolate

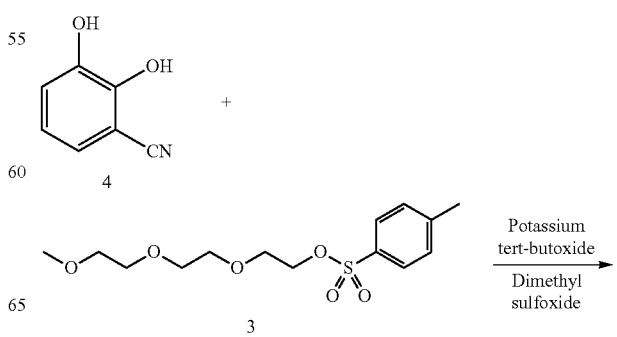

-continued

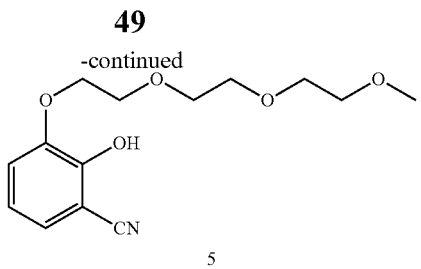

5

A 100 gallon glass lined reactor was charged with 2,3-dihydroxybenzonitrile (4) and dimethyl sulfoxide. A 300 gallon glass lined reactor was charged with potassium tert-butoxide and dimethyl sulfoxide. The 2,3-dihydroxybenzonitrile solution was slowly charged over 1 hour to the potassium tert-butoxide solution maintaining the temperature at ≤50° C. The reaction mixture was agitated. 2-(2-(2-Methoxyethoxy)ethoxy)ethyl 4-methylbenzenesulfonate (3) was charged over a 1 hour period to the reaction mixture. The reaction mixture was agitated for 2 hours and sampled for reaction completion analysis by HPLC. The reaction was quenched by charging USP water and agitating for 1 hour. The product was isolated first by washing the reaction mixture twice with methyl t-butyl ether. 6N HCl was charged to the aqueous mixture. The product was then extracted twice with methylene chloride. The organic layers (product layers) were combined and the solvent was exchanged into ethanol by vacuum distillation. A 30% sodium hydroxide solution was charged to the product dissolved in ethanol. Methyl t-butyl ether was added to help completely precipitate the product. The product was isolated by vacuum filtration. The wet cake was dried for over 15 hours in a tumble drier at 40° C. The reaction yielded sodium 2-cyano-6-(2-(2-(2-methoxyethoxy)ethoxy) ethoxy)phenolate (5).

Step 3: Synthesis of (S)-4,5-Dihydro-2-[2-hydroxy-3-(3,6,9-trioxadecyloxy) phenyl]-4-methyl-4-thiazolecarboxylate magnesium hydroxide

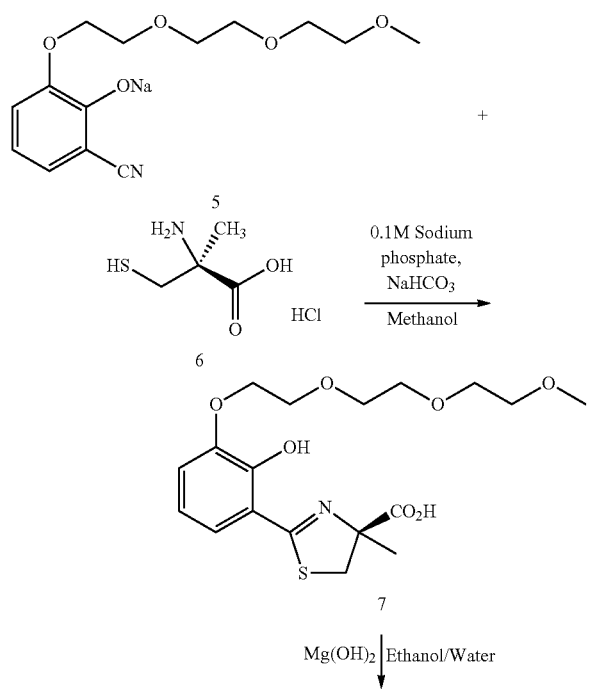

-continued

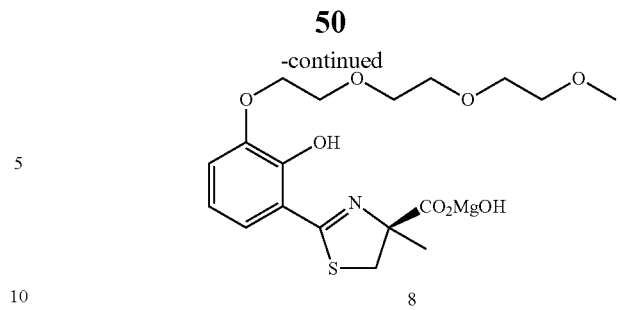

8

A 100 L glass jacketed reactor and 100 L glass jacketed flask were pre-rinsed with aqueous HCl followed by a USP water rinse. Sodium phosphate monobasic monohydrate, sodium phosphate dibasic, USP Water, methanol were charged to the 100 L glass jacketed reactor and agitated for 15 minutes. The solution was purged with a stream of nitrogen for 24 minutes. 2-cyano-6-(2-(2-(2-methoxyethoxy)ethoxy) ethoxy)phenolate (5) and 2-methyl-D-cysteine HCl (6) were charged to the reactor. Sodium bicarbonate was slowly charged to the reactor. The reaction was heated to 70° C. and held at this temperature for over 4 hours. After the in-process HPLC reaction completion sample passed specification some solvent was removed by vacuum distillation. The aqueous product solution was purified by washing twice with ethyl acetate. The product precipitated when 6N HCl was charged to the reactor. The product was extracted into ethyl acetate. The solvent was exchanged into ethanol by vacuum distillation. An in-process analysis was performed to measure the yield of (S)-2-(2-hydroxy-3-(2-(2-(2-methoxyethoxy) ethoxy)phenyl)-4-methyl-4,5-dihydrothiazole-4-carboxylic acid (7) and this value was used to calculate the amount of magnesium hydroxide solution to prepare. The magnesium salt was prepared and precipitated by addition of magnesium hydroxide and methyl t-butyl ether. The product was collected by filtration and dried in a tumble drier at 45° C. for over 21 hours. The product was forced through a 20 Mesh sieve and continued to dry for over 18 hours to yield (S)-4,5-Dihydro-2-[2-hydroxy-3-(3,6,9-trioxadecyloxy)phenyl]-4-methyl-4-thiazolecarboxylate magnesium hydroxide ((S)-3'-(OH)-DADFT-PE MgOH) (8) (Compound 1).

The $^1$H-NMR spectrum was obtained using a Bruker 400 MHz NMR. The reference standard was prepared by dissolving (S)-3'-(OH)-DADFT-PE MgOH into deuterated dimethylsulfoxide. The $^1$H-NMR spectrum confirms the structure of (S)-3'-(OH)-DADFT-PE MgOH.

The $^{13}$C-NMR spectrum was obtained using a GE 300 MHz QE Plus. The reference standard was prepared by dissolving (S)-3'-(OH)-DADFT-PE MgOH into deuterated dimethylsulfoxide. The $^{13}$C-NMR spectrum confirms the structure of (S)-3'-(OH)-DADFT-PE MgOH.

The chemical purity was determined using a Varian Prostar HPLC with the conditions specified in Table 1. The chemical purity of the reference standard was 97.5% (peak area %).

TABLE 1

| Chemical Purity Parameters | |
|---|---|
| Column: | Phenomenex Luna C18, 5 μm, 4.6 × 150 mm, |
| Mobile Phase: | A = 49:51 20 mM Potassium phosphate buffer, pH 6.5:Methanol |
| | B = Methanol |
| | Time   A   B |
| Gradient: | 0       100   0 |
| | 12      100   0 |

TABLE 1-continued

Chemical Purity Parameters

| | | | |
|---|---|---|---|
| | 20 | 20 | 80 |
| | 25 | 20 | 80 |
| | 26 | 100 | 0 |
| | 36 | 100 | 0 |
| Sample Solvent: | Methanol | | |
| Flow Rate: | 1.0 mL/min | | |
| Wavelength: | 222 nm | | |
| Injection Volume: | 10 μL | | |
| Run Time: | 25 minutes | | |
| Column Temperature: | 30° C. | | |
| Sample Temperature: | Ambient | | |
| Sample Concentration: | ~0.6 mg/mL Methanol | | |

The chiral purity was determined using a Waters 2695 Separations Module with the conditions specified in Table 2. No (R)-3'-(OH)-DADFT-PE was observed during the analysis.

TABLE 2

Chiral Purity Parameters

| | |
|---|---|
| Column: | ChiralPak AD, 10 μm, 4.6 × 250 mm, |
| Mobile Phase: | 70:30:0.1 Hexanes:Isopropyl alcohol:Trifluoroacetic acid |
| Sample Solvent: | 70:30 Hexanes:Isopropyl alcohol |
| Flow Rate: | 1.0 mL/min |
| Wavelength: | 220 nm |
| Injection Volume: | 10 μL |
| Run Time: | 15 minutes |
| Column Temperature: | Ambient |

TABLE 2-continued

Chiral Purity Parameters

| | |
|---|---|
| Sample Temperature: | Ambient |
| Sample Concentration: | ~0.45 mg/mL Sample Solvent |

The (S)-3'-(OH)-DADFT-PE MgOH was tested by XRPD at SSCI, West Layfayette, 1N, to confirm its Form. The acceptance criteria for the test is that the sample diffractogram compares favorably with that of the Form A reference pattern. The XRPD pattern was collected using a PA Nanytical X'Pert Pro diffractometer. An incident beam of CU Kα radiation was produced using an Optix long, fine-focu sourcer. An elliptically graded multilayer mirror was used to focus the CU Kα X-rays of the X'Pert Pro Data Collector software (v. 2.2b). Prior to the analysis, a silicone specimen (NIST SRM 640c) was analyzed to verify the Si 111 peak position. The specimen was sandwiched between 3 μm thick films, analyzed in transmission geometry, and rotated to optimize orientation statistics. A beam-stop and anti-scattering extension were used to minimize the background generated by air scattering. Helium was not used. Soller slits were used for the incident and diffracted beams to minimize axial divergence. Diffraction patterns were collected using a scanning-sensitive detector (X'Celerator™) located 240 mm from the specimen. The pattern was collected using the following diffraction conditions:

X-ray Tube Voltage: 4 kV
X-ray Tube Current: 40 mA
X-ray Tube Radiation: Cu Kα (1.54060 A)
Automatic Step Scans:
(a) Step-Size: 0.017° 2θ
(b) Count time per step: 1.0 second
Scan Speed: ½°/min
Fixed Slits: ½ SS° divergence/0.2° receiving
Graphite Crystal Monochromator
Temperature: Ambient Lab
Scan Range: 1.0-39.98 °θ

The XRPD analysis of (S)-3'-(OH)-DADFT-PE indicated it exists as crystalline Form A, described in more detail in Example 13. See also US 2010/0137383 for additional characterization data for Form A, the entire contents of which are hereby incorporated by reference.

Example 2

Tromethamine salt of (S)-4'-(OH)-DADFT-PE (Compound 2)

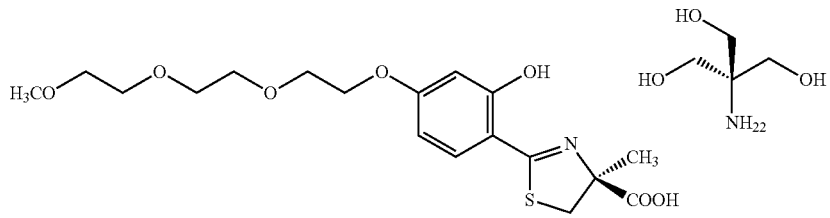

Compound 2 has been and may be synthesized as described in Bergeron, R J et al., "Design, Synthesis, and Testing of Non-Nephrotoxic Desazadesferrithiocin Polyether Analogues," *J Med. Chem.* 2008, 51(13), 3913-23, and as described in US20080214630A1 published Sep. 4, 2008.

Base was added to an ethanolic solution of the API. A clear solution was obtained by stirring at room temperature for ~3 hr. Fast evaporation of the solution yielded the tromethamine salt of the API. Tromethamine salt candidate is consistent with crystalline unsolvated tromethamine salt of 4'-(OH)-DADFT-PE with ~1:1 ratio of tromethamine to API. The salt exhibited significant aqueous solubility (above ~124 mg/mL) and showed no apparent deliquescence upon ~75% RH stress. The salt showed a small water uptake (~1.5 wt %) below ~65% RH above which it gained ~50.3 wt % indicating lower hygroscopicity compared to magnesium and NMG salt candidates.

Example 3

Capsule formulations of (S)-4,5-Dihydro-2-[2-hydroxy-3-(3,6,9-trioxadecyloxy)phenyl]-4-methyl-4-thiazolecarboxylate magnesium hydroxide ((S)-3'-(OH)-DADFT-PE MgOH) (Compound 1)

Prototypes of two different blends were manufactured and put on a 6 week stability program with testing at week 2, 4, and 6. The first blend was 96% API, 3% Croscarmellose Sodium NF Type A, and 1% Magnesium Stearate. The second blend consisted of 96% API, 3% Sodium Starch Glycolate NF (Explotab), and 1% Stearic Acid Powder NF. Although the analytical results were similar, the first formulation was chosen for development. Prototype hard gelatin capsules with 96% API, 3% Croscarmellose Sodium NF Type A, and 1% Magnesium Stearate of 50, 100, 250 mg, 375 mg, and 500 mg strengths were manufactured and put on an ICH 2 year stability program.

Sufficient stability from clinical trial materials has been accrued on all capsule strengths. Six-month accelerated stability data, as well as 9-24 months at the recommended storage temperature demonstrate that there are no issues with capsule stability to date. The drug product has been shown to be stable across a range of doses (50 mg, 100 mg, 200 mg, 250 mg, 375 mg and 500 mg), across a range of capsule sizes (size 4, size 2, size 0 and size 00), and across a range of capsule colors (white, blue, orange, gray and Swedish orange). Given the body of data accrued, use of capsules made with slightly larger capsules shells (size 00E) or with slight dye changes (replacement of FD&C dyes with iron oxide) is not expected to affect stability. Drug product manufactured with these capsule variations will be placed on stability.

The batch formulas for the (S)-3'-(OH)-DADFT-PE MgOH Blend are provided Table 3 below. Similar formulations can be mase comprising other chelator compounds as disclosed herein. Additionally, those of skill in the art will understand that each excipient may serve more than one purpose in a formulation.

TABLE 3

(S)-3'-(OH)-DADFT-PE MgOH Blend Batch Formula

| Component | Quality Standard | Function | Composition Quantity % (w/w) | Theo Batch Quantity (Kg) | Actual Batch Quantity (Kg) |
|---|---|---|---|---|---|
| (S)-3'-(OH)-DADFT-PE MgOH | Manufacturer's Specifications | Active | 96.0 | 3.072 | 3.072 |
| Croscarmellose Sodium | NF Type A | Diluent | 3.0 | 0.096 | 0.096 |
| Magnesium Stearate | NF/EP Non-Bovine #5712 | Lubricant/Glidant | 1.0 | 0.032 | 0.032 |

The (S)-3'-(OH)-DADFT-PE MgOH blend formulation is filled into empty hard gelatin capsule using the appropriate encapsulator in the calculated amounts to produce the appropriate capsules strengths. A flow diagram for the drug product (S)-3'-(OH)-DADFT-PE MgOH 50 mg, 100 mg, 200 mg, 250 mg, 375 mg, and 500 mg capsules manufacturing process is provided in FIG. 1.

The excipients blended in the formulation with (S)-3'-(OH)-DADFT-PE MgOH are compendial and are tested in accordance with the current compendial methods (see Tables 4-10). These excipients are not of human or animal origin.

The hard gelatin capsules are manufactured from a blend of pharmaceutical gelatins. When bovine gelatin is used, it is alkaline processed, pharmaceutical grade, and in compliance with pharmaceutical regulatory requirements.

TABLE 4

Exemplary Capsule Specifications

| Test | Method | Specification |
|---|---|---|
| Appearance | Visual | Off-white to yellow to light brown solid contained in a hard gelatin capsule. |

TABLE 4-continued

Exemplary Capsule Specifications

| Test | Method | Specification |
|---|---|---|
| Identification (HPLC) | HPLC | The retention time of the main peak in the sample is within ±5% of the main peak in the standard solution |
| Assay | HPLC | 90.0% to 110.0% of label claim |
| Related Substances | | |
| Individual impurity | HPLC | Individual Impurities: Report results (report RRT and area % for all impurities ≥0.05%) No individual impurity >1.0% |
| Total impurities | | ≤3% |
| Moisture | USP <921> Water Determination Method 1a (Direct Titration) | 3-15% |
| Dissolution | HPLC | Q = 70% at 60 min |
| Disintegration | USP <701> Disintegration | NMT 19 min |
| Content Uniformity | USP <905> Uniformity of Dosage Units, Weight Variation | Meets USP requirements |
| Microbial Enumeration Tests: | | |
| Total Aerobic Microbial Count (TAMC) | (Harmonized USP <61> and Ph. Eur. 2.6.12) | NMT 1000 cfu/g |
| Total Yeast and Mold Count (TYMC) | (Harmonized USP <61> and Ph. Eur. 2.6.12) | NMT 100 cfu/g |
| Tests for Specified Microorganisms | (Harmonized USP <62> and Ph. Eur. 2.6.13) | Absence of *E. coli*, *P. aeruginosa*, *Salmonella* spp., and *S. aureus* |

TABLE 5

50 mg capsule (Capsule 2)

| Component | Function | Specification | Quantity per capsule | Percent Weight |
|---|---|---|---|---|
| (S)-3'-(OH)-DADFT-PE MgOH | Active | Manufacturer's Specifications | 48 mg | 96% |
| Croscarmellose Sodium | Diluent | NF Type A | 1.5 mg | 3% |
| Magnesium Stearate | Lubricant/Glidant | NF/EP Non-Bovine #5712 | 0.5 mg | 1% |
| Total Fill Weight | | | 50 mg | |

TABLE 6

100 mg capsule (Capsule 3)

| Component | Function | Specification | Quantity per capsule | Percent Weight |
|---|---|---|---|---|
| ((S)-3'-(OH)-DADFT-PE MgOH | Active | Manufacturer's Specifications | 96 mg | 96% |
| Croscarmellose Sodium | Diluent | NF Type A | 3 mg | 3% |
| Magnesium Stearate | Lubricant/Glidant | NF/EP Non-Bovine #5712 | 1 mg | 1% |
| Total Fill Weight | | | 100 mg | |

TABLE 7

200 mg capsule (Capsule 4)

| Component | Function | Specification | Quantity per capsule | Percent Weight |
|---|---|---|---|---|
| (S)-3'-(OH)-DADFT-PE MgOH | Active | Manufacturer's Specifications | 192.0 mg | 96% |
| Croscarmellose Sodium | Diluent | NF Type A | 6 | 3% |
| Magnesium Stearate | Lubricant/Glidant | NF/EP Non-Bovine #5712 | 2.0 mg | 1% |
| Total Fill Weight | | | 200 mg | |

TABLE 8

250 mg capsule (Capsule 5)

| Component | Function | Specification | Quantity per capsule | Percent Weight |
|---|---|---|---|---|
| (S)-3'-(OH)-DADFT-PE MgOH | Active | Manufacturer's Specifications | 240 mg | 96% |
| Croscarmellose Sodium | Diluent | NF Type A | 7.5 mg | 3% |
| Magnesium Stearate | Lubricant/Glidant | NF/EP Non-Bovine #5712 | 2.5 mg | 1% |
| Total Fill Weight | | | 250 mg | |

TABLE 9

375 mg capsule (Capsule 6)

| Component | Function | Specification | Quantity per capsule | Percent Weight |
|---|---|---|---|---|
| (S)-3'-(OH)-DADFT-PE MgOH | Active | Manufacturer's Specifications | 360 mg | 96% |
| Croscarmellose Sodium | Diluent | NF Type A | 11.25 mg | 3% |
| Magnesium Stearate | Lubricant/Glidant | NF/EP Non-Bovine #5712 | 3.75 mg | 1% |
| | | Total Fill Weight | 375 mg | |

TABLE 10

500 mg capsule (Capsule 7)

| Component | Function | Specification | Quantity per capsule | Percent Weight |
|---|---|---|---|---|
| (S)-3'-(OH)-DADFT-PE MgOH | Active | Manufacturer's Specifications | 480 mg | 96% |
| Croscarmellose Sodium | Diluent | NF Type A | 15.0 mg | 3% |
| Magnesium Stearate | Lubricant/Glidant | NF/EP Non-Bovine #5712 | 5.0 mg | 1% |
| | | Total Fill Weight | 500 mg | |

Dissolution Analysis and Characterization of Capsules 2-5

Dissolution analysis may be conducted per standard USP, European Pharmacopoeia, British Pharmacopoeia, or other protocols. The dissolution profile of capsules 2-5 is determined by utilizing a standard apparatus (e.g., basket) and removing samples at timed intervals. Samples are analyzed by reverse-phase HPLC chromatography and compared against a known standard to quantify the potency of (S)-3'-(OH)-DADFT-PE MgOH API in solution. Six samples were tested per batch of capsules prepared, then the mean percent dissolution was calculated for each batch. Results are shown below in Table 11.

TABLE 11

| Time, min. | Percent Dissolution Capsule 2 | Percent Dissolution Capsule 3 | Percent Dissolution Capsule 4 | Percent Dissolution Capsule 5 |
|---|---|---|---|---|
| 10 | 20.3-78.6% | 10.0-55.7% | 7.3-63.4% | 19.9-33.8% |
| 20 | 61.1-95.8% | 37.8-80.6% | 16.8-89.6% | 41.2-71.0% |
| 30 | 74.8-100.2% | 56.5-91.5% | 25.0-95.9% | 54.4-81.2% |
| 45 | 88.1-102% | 79.1-100.0% | 34.7-101.0% | 64.7-90.1% |
| 60 | 92.2-102.2% | 86.8-102.9% | 43.1-104.2% | 73.4-94.3% |

Hygroscopicity Analysis of Capsules 2-5

Capsules 2-5 were tested for stability under controlled, accelerated conditions. Capsules 2-5 were stored at 60% relative humidity and 25° C. for up to twelve months. Results are shown below in Table 12.

TABLE 12

| Ex. | Water Content, Initial | Water Content, 1 Month | Water Content, 2 Months | Water Content, 3 Months | Water Content, 6 Months | Water Content, 9 Months | Water Content, 12 Months |
|---|---|---|---|---|---|---|---|
| 2 | 6.9-7.7% | 7.3-7.6% | 7.1-7.8% | 7.2-8.2% | 7.6-8.0% | 7.8-8.0% | 7.2-8.2% |
| 3 | 6.5-7.5% | 7.3-7.8% | 7.2-7.5% | 7.0-7.9% | 7.3-7.7% | 7.7% | 7.0-8.1% |
| 4 | 6.5-7.1% | 6.9-7.1% | 6.7-7.3% | 6.7-7.5% | 7.0-7.5% | 7.5% | 6.9-7.6% |
| 5 | 6.5-7.1% | 7.0% | 6.9% | 6.8-7.5% | 6.9% | 7.3% | 7.6% |

Hygroscopicity Analysis of Capsules 2-5

Capsules 2-5 were tested for stability under controlled, accelerated conditions. Capsules of Examples 2-5 were stored at 75% relative humidity and 40° C. for two months. Results are shown below in Table 13.

TABLE 13

| Ex. | Water Content, Initial | Water Content, 1 Month | Water Content, 2 Months | Water Content, 3 Months | Water Content, 6 Months |
|---|---|---|---|---|---|
| 2 | 6.9-7.7% | 7.3-7.6% | 7.0-7.5% | 7.0-7.6% | 7.3-7.9% |
| 3 | 6.5-7.5% | 7.0-7.6% | 7.2-7.5% | 7.1-7.5% | 7.3-7.8% |
| 4 | 6.5-7.1% | 7.3-7.4% | 7.1-7.2% | 7.0-7.3% | 7.3-7.8% |
| 5 | 6.5% | 7.2% | 7.1% | 7.2% | 7.2% |

Capsule formulations of (S)-2-(2-hydroxy-4-(2-(2-(2-methoxyethoxy)ethoxy) ethoxy)phenyl)-4-methyl-4,5-dihydrothiazole-4-carboxylate-(S)-4'-(OH)-DADFT-PE (Compound 2)

Capsule formulations of (S)-2-(2-hydroxy-4-(2-(2-(2-methoxyethoxy)ethoxy)ethoxy)phenyl)-4-methyl-4,5-dihydrothiazole-4-carboxylate, also known as (S)-4'-(OH)-DADFT-PE, can be prepared using the process described above.

Dosing Formulations

Unless otherwise indicated, the formulation of compound 1 used in the following Examples is a blended formulation of 96% (wt/wt) of compound 1 (powder) with 3% (wt/wt) croscarmellose sodium and 1% (wt/wt) magnesium stearate dispensed into hard gelatin capsules. A single blend is used for all strengths; the dose is dependent only on fill weight. The capsules are manufactured in strengths of 50, 100, 200, 250, 375, and 500 mg of total fill weight. The route of administration is oral.

Example 4

Seven-Day Dosing in Iron-Overloaded Human Subjects

A dose-escalation study to assess the safety, tolerability, pharmacokinetics and pharmacodynamics of Compound 1, which correspond to a capsule formulation of (S)-3'-(OH)-DADFT-PE was conducted in 16 adult patients with iron overloaded consequent to transfusions. Compound 1 was given daily for 7 days at doses up to 32 mg/kg and was well tolerated at all dose levels. Compound 1 was supplied as capsules containing 50 mg, 100 mg, or 250 mg. The capsules were manufactured in accordance with Annex 13 and the principle of cGMP at Aptuit (10245 Hickman Mills Drive, Kansas City, Mo. 64137).

Patients.

Patients 18 years or older with documented transfusional iron overload requiring chronic treatment with deferiprone, deferasirox or deferoxamine were eligible. Causes of iron overload included β-thalassemia major, α-thalassemia or α-thalassemia hydrops)(α°α°, sickle cell disease, and congenital dyserythropoietic anemia. Each of the four cohorts contained four patients. For the purposes of this study, transfusion dependence was defined as requiring eight or more transfusions per year. The iron burden inclusion criteria were defined as: (i) liver iron concentration greater than 2 mg/g (dry weight, liver) as determined by R2 magnetic resonance imaging; (ii) a cardiac magnetic resonance imaging T2* greater than 12 ms; and (iii) serum ferritin in excess of 600 ng/mL. Eligible patients who consented to participation in the study discontinued their regular chelation therapy for up to 5 days during a wash-out period prior to their first dose of Compound 1. Patients received Compound 1 in capsules taken orally in a fasted state.

Pharmacokinetic Analysis.

In this study, a standard pharmacokinetic protocol of plasma sampling was performed throughout the 7 days of dosing and continuing for 3 days after the last dose on day 7. Actual blood sampling and urine collection times were used in all pharmacokinetic analyses. Per protocol times were used to calculate mean plasma concentrations for graphical displays. A formally validated bioanalytical method for quantifying total Compound 1 in human plasma and urine was developed. The drug was extracted from plasma using solid phase extraction and analyzed using high performance liquid chromatography with tandem mass spectrometric determination, and d3-[Compound 1] as an internal standard. The method was used to measure drug (MW 400) over the range of 5 to 2000 ng/mL (12.5-5000 nM) and at sample dilutions of 20- to 50-fold. Because of the low pH, the chromatographic eluent displaces all iron from chelate complexes and thus the bioanalytical method provides total drug concentration and does not differentiate drug bound to iron from unbound drug.

Pharmacokinetic parameters for Compound 1 were estimated using non-compartmental analysis. Only plasma and urine concentrations greater than the lower limits of quantitation (LOQ, 5 ng/mL in plasma, 5 ng/mL in urine) for the assays were used in the pharmacokinetic analysis. The following pharmacokinetic parameters for Compound 1 were determined from plasma concentration and urinary excretion data: the area under the plasma concentration versus time curve over the 24-hour time dosing interval ($AUC_{0-24}$); the maximum observed plasma concentration ($C_{max}$); the time to maximum plasma concentration (tmax); the terminal elimination rate constant ($\lambda z$) and half-life (t½); the apparent total plasma clearance of drug after oral administration (CL/F); the apparent volume of distribution during terminal phase after oral administration (Vz/F); the fraction of the oral dose excreted into urine (Ue); and renal clearance (CLr).

Statistical Analysis.

Plasma concentrations, blood sampling times, urine concentrations, urine volumes, and the amount excreted in each interval, and pharmacokinetic parameters were listed by dose group and patient. Plasma concentrations and pharmacokinetic parameters were summarized by dose group using descriptive statistics: linearity with respect to Cmax and AUC (0-24) was assessed using the power model, i.e. P=a×Doseb, where P represents the parameter and a and b are constants. A log-log plot of P versus Dose is linear and a value of b of ≈1 indicates linearity. The equation was fitted to the individual patients' data using non-linear least squares regression. Parameters were compared among doses using descriptive statistics. Due to the small numbers of patients per panel, no formal statistical analyses were done.

|  | 3 mg/kg | 8 mg/kg | 16 mg/kg | 32 mg/kg |
| --- | --- | --- | --- | --- |
| Cmax, ng/mL | 5910 ± 2298 | 15000 ± 4439 | 38,225 ± 3947 | 60250 ± 27519 |
| Tmax, h | 1.31 | 1.18 | 1 | 1.49 |
| $AUC_{(0-24)}$, ng · h/mL | 19476 ± 11327 | 44916 ± 30751 | 92261 ± 36560 | 157577 ± 43484 |
| t½, h | 16.2 ± 8.32 | 20.9 ± 11.3 | 21.3 ± 11.8 | 18.7 ± 4.48 |
| CL/F, mL/min | 162 ± 85 | 225 ± 142 | 206 ± 78.4 | 172 ± 60.1 |
| Vz/F, L | 185 ± 84.1 | 311 ± 137 | 339 ± 166 | 214 ± 2.94 |
| CLr, mL/min | 75.2 ± 46.8 | 105 ± 62.9 | 83.2 ± 36.5 | 73.6 ± 37.8 |

Plasma concentrations increased in a dose-related manner and decayed at essentially the same rate after all four doses, demonstrating dose-proportional, linear pharmacokinetics. The maximum plasma concentration ($C_{max}$) was reached within 60-90 minutes of dosing and the drug was rapidly distributed at the predicted therapeutic doses. Mean values for Cmax and AUC(0-24) also increased in a dose-proportional manner. There were no dose-related trends in either CL/F or Vz/F and the mean elimination half-life, t½, was independent of dose. CL/F is directly related to body weight, indicating that weight-based dosing is appropriate for Compound 1. The t½ of 19.2 hours demonstrates that once-daily dosing is feasible. There were no serious adverse events associated with the drug.

The protocol was later amended to include a 5th cohort of four patients at the 40 mg/kg dose level. The pharmacokinetics of the 40 mg/kg continued the dose-proportional trend. Mean half life (t½) was slightly longer at 26.6 h.

Example 5

Single-Dose Study—Iron-Overloaded Human Subjects

Example 5 was a single-dose, escalating study in iron-overloaded subjects. Men between the ages of 18-50 years qualified to participate if they were able to voluntarily give consent and had transfusional overload requiring treatment with an iron chelator and were willing to discontinue their chelation for a period of at least 7 days prior to screening and during the study. Eligible subjects had serum ferritin levels >300 ng/mL and ≤5000 ng/mL. Subjects had blood pressure in the normal range, ECG within normal limits and tested negative for drugs of abuse. Subjects were also HIV and Hepatitis B negative and agreed to use an approved method of contraception during the study.

The objectives of this study were to assess the safety, tolerability, and pharmacokinetics of ascending single doses of Compound 1. Additionally, dose proportionality and pharmacodynamics of Compound 1 were assessed. Four doses of Compound 1 (6, 10, 16, and 32 mg/kg), in capsule form, were evaluated in this study. Each dose level was tested in a single subject, with appropriate evaluation of safety done prior to escalating the dose. Following screening, the first subject was dosed and then confined to the clinical research unit for 24 hours to conduct safety and pharmacokinetic assessments. The subject was released from the clinic on Day 2 and returned daily for follow-up visits for 5 days post-dosing. This process was followed for each dose level.

All 4 subjects who received a dose of Compound 1 were included in the analysis of pharmacokinetic parameters.

Plasma Pharmacokinetic Parameters

Maximum total (free and iron bound complex) plasma concentrations following single oral administration of Compound 1 occurred between 0.7 and 1.0 hour with mean $t_{max}$ of 0.925 hours averaged across all dose levels. The mean terminal half-life of Compound 1 ranged from 16-30 hours with a mean $t_{1/2}$ of 23.7 hours averaged across all dose levels. There was no apparent dose-dependency of $t_{1/2}$. $C_{max}$ and AUC were dose-proportional across the 6-32 mg/kg dose range. The plasma concentrations at 24 hours post-dose in all subjects at the 6, 10, 16, and 32 mg/kg dose levels were <1% of $C_{max}$. On the basis of these data, it is anticipated there would be minimal accumulation of Compound 1 with repeated once-daily dose administration. These data are summarized in Table 14.

Example 6

Multiple-Dose Study—Iron-Overloaded Human Subjects

Example 6 was a multiple-dose, escalating study in iron-overloaded subjects conducted at 5 centers in the US, Australia, and Thailand.

Men and women at least 18 years of age qualified to participate if they were able to voluntarily give consent and had transfusional overload requiring treatment with an iron chelator and were willing to discontinue their chelation for a period of at least 5 days prior to screening and during the study for a total of up to 35 days. Specifically, subjects had a liver iron concentration ≥1.5 mg/g and cardiac iron determined by the T2* method of ≥12 msec. The mean of each subject's last 3 pre-transfusion hemoglobin levels (prior to screening) was ≥7.5 g/dL and their serum ferritin was >400 ng/mL. Subjects also agreed to use an approved method of contraception during the study.

The study enrolled 20 subjects with the following primary diagnoses requiring chronic transfusions:

Cohort 1 (3 mg/kg):
  2 β-thalassemia major
  2 sickle cell anemia

Cohort 2 (8 mg/kg):
  1 α-thalassemia major (α°/α°)
  2 β-thalassemia major
  1 congenital dyserythropoietic anemia Cohort 3 (16 mg/kg):
  4 β-thalassemia major Cohort 4 (32 mg/kg):
  1 α-thalassemia major (α°/α°)
  2 β-thalassemia/hemoglobin E
  1 sickle cell anemia Cohort 5 (40 mg/kg):
  2 β-thalassemia major
  2 β-thalassemia/hemoglobin E Pharmacokinetic parameters are summarized in Table 15. Maximum plasma concentrations following single oral administration of Compound 1 after 7 days of daily dosing occurred at times ranging from 1.0-1.49 hours with a mean of 1.24 hours. The $C_{max}$ and AUC were approximately dose-proportional. The median values for $t_{max}$ ranged from 1.00 to 1.49 hours and were not dependent on dose. There were no

TABLE 14

Summary of Plasma Pharmacokinetic Parameters

| Subject | Dose Level | Dose (mg) | $t_{max}$ (hr) | $C_{max}$ (ng/mL) | $AUC_{0-t}$ (ng·hr/mL) | $AUC_{0-\infty}$ (ng·hr/mL) | CL/F (L/hr) |
|---|---|---|---|---|---|---|---|
| 1 | 6 mg/kg | 360 | 1.00 | 14900 | 45901 | 46256 | 7.9 |
| 2 | 10 mg/kg | 583 | 0.77 | 35400 | 69239 | 69732 | 8.4 |
| 3 | 16 mg/kg | 1288 | 1.00 | 38500 | 122085 | 122184 | 10.6 |
| 4 | 32 mg/kg | 2214.4 | 1.00 | 47600 | 157134 | 158643 | 14.1 |

$AUC_{(0-t)}$ = area under the plasma concentration-time curve from time 0 to last sampling time; $AUC_{0-\infty}$ = area under the plasma concentration-time curve from time 0 to infinity; CL/F = relative clearance; $C_{max}$ = maximum plasma concentration; $t_{max}$ = time to $C_{max}$ Urine pharmacokinetic parameters of Compound 1 were determined in the 4 subjects. The total fraction of orally administered Compound 1 excreted in urine over the 24 hour post-dose period ranged from 28-51% across the 4 dose levels in a dose-independent manner (average 39%).

dose-related trends in either CL/F or Vz/F and the mean $t_{1/2}$ ranged from 12.9 to 21.3 hours and was independent of dose. Consistent with linear pharmacokinetics, the urinary recovery of Compound 1 was comparable across the 5 cohorts, with mean recovery ranging from 39.2 to 48.4% of the dose.

TABLE 15

Summary of Plasma Pharmacokinetic Parameters

| Parameter | Dose (mg/kg/day) | | | | |
|---|---|---|---|---|---|
| | 3 | 8 | 16 | 32 | 40 |
| $C_{max}$ (ng/mL) | 5910 ± 2298 (4) | 15000 ± 4439 | 38225 ± 3947 | 68250 ± 27519 | 68600 ± 10958 |
| $t_{max}$ (hr) | 1.31 | 1.18 | 1.0 | 1.49 | 1.26 |
| $AUC_{(0-24)}$ (hr × ng/mL) | 19476 ± 11327 | 44916 ± 30751 | 92261 ± 36560 | 157577 ± 43484 | 140923 ± 8068 |
| $\lambda z$ (hr$^{-1}$) | 0.0655 ± 0.0606 | 0.0424 ± 0.0249 | 0.0421 ± 0.0246 | 0.0381 ± 0.0091[a] | 0.0544 ± 0.0071 |
| $T_{1/2}$ (hr) | 16.2 ± 8.32 | 20.9 ± 11.3 | 21.3 ± 11.8 | 18.7 ± 4.48[a] | 12.9 ± 1.68 |
| CL/F (mL/min) | 162 ± 85.0 | 225 ± 142 | 206 ± 78.4 | 172 ± 60.1 | 223 ± 23.6 |
| Vz/F (L) | 185 ± 84.1 | 311 ± 137 | 339 ± 166 | 214 ± 2.94[a] | 249 ± 40.4 |
| $U_{e(0-24)}$ (mg) | 66.1 ± 24.0 | 201 ± 68.1 | 402 ± 103 | 641 ± 208 | 905 ± 247 |
| $F_{e(0-24)}$ (% oral dose) | 44.0 ± 16.0 | 47.2 ± 13.8 | 39.2 ± 5.86 | 43.1 ± 15.8 | 48.4 ± 14.0 |
| $Cl_r$ (mL/min) | 75.2 ± 46.8 | 105 ± 62.9 | 83.2 ± 3605 | 73.6 ± 37.8 | 107 ± 26.2 |

[a] N = 2. All other means are based on N = 4.
$AUC_{0-24}$ = area under the plasma concentration-time curve from time 0 to 24 hours;
CL/F = apparent oral-dose clearance;
CLr = renal clearance;
$C_{max}$ = maximum plasma concentration;
$F_{e(0-24)}$ = fraction excreted from time 0 to 24 h;
$t_{1/2}$ = apparent terminal-phase disposition half-life;
$t_{max}$ = time to $C_{max}$;
$U_{e(0-24)}$ = urinary excretion from time 0 to 24 h;
Vz/F = apparent volume of distribution;
$\lambda_Z$ = terminal-phase disposition rate constant.

Figure 10:
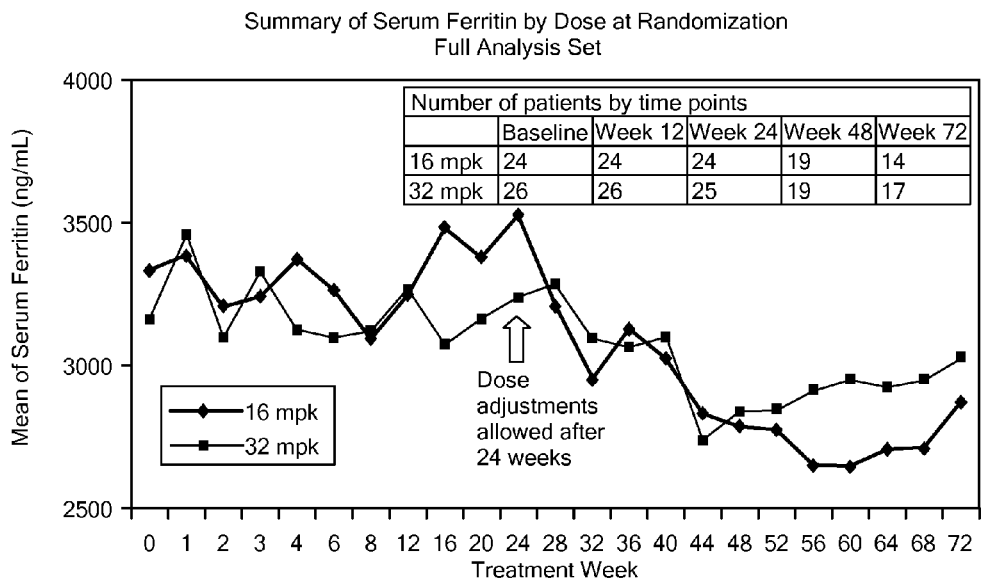
FIG. 10. Exemplary summary of serum ferritin by dose at randomization.

Preliminary analysis of the pharmacokinetic results from the clinical studies as a whole indicates that there was dose-proportionality in $C_{max}$ and AUC over the dosing range of 3 to 50 mg/kg with a possible less than proportional increase at 60 and 75 mg/kg. The results were similar across the common doses in the 4 studies. The $t_{max}$ was approximately 1 hour in each study; there were no data to date suggesting drug accumulation at steady state, that is, after 7 days of daily administration in subjects. See also FIG. 10.

Example 7

Safety and Tolerability of High Doses in Healthy Human Subjects

Subjects were male and female healthy human volunteers aged between 18 and 50 years, free from clinically significant illness or disease as determined by their medical/surgical history, physical examination etc., and having a serum ferritin>20 ng/mL. Subjects were given, in the fasted state, either 30, 40, 50, or 60 mg/kg Compound 1 as a blended formulation of 96% (wt/wt) drug substance (powder) with 3% (wt/wt) croscarmellose sodium and 1% (wt/wt) magnesium stearate dispensed in hard gelatin capsules in strengths of 50 mg, 100 mg, 250 mg, and 375 mg.

The 30 and 50 mg/kg dose groups each contained seven subjects; data from only four of these subjects was used to calculate $AUC_{inf}$, t½, CL/F, and $V_z$/F. The 40 and 60 mg/kg dose groups each contained three subjects; data from only three of these subjects was used to calculate $AUC_{inf}$, t½, CL/F, and $V_Z$/F.

Figure 2:
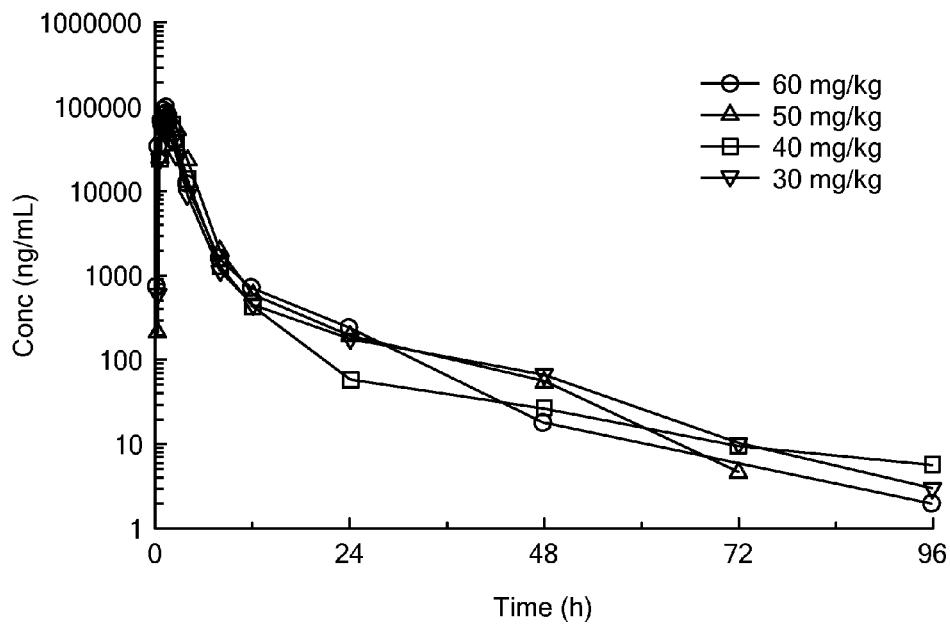
FIG. 2. Exemplary arithmetic mean plasma concentrations of Compound 1 after oral administration of single 30 mg/kg, 40 mg/kg, 50 mg/kg, and 60 mg/kg doses to healthy volunteers—semi-logarithmic axes.

Blood samples of approximately 7 mL were drawn via cannula at 0.25, 0.5, 0.75, 1, 1.25, 1.5, 2, 2.5, 4, 8, 12 and 24 hours post-dose, for pharmacokinetic analysis. (See FIG. 2.) Urine was collected over the time periods 0-4, 4-8, 8-12 and 12-24 hours post-dose for pharmacokinetic and pharmacodynamic assessment.

PK plasma and PK urine samples were assayed by a validated LC/MS/MS method, specific for the determination of Compound 1. Pharmacokinetic parameters for Compound 1 will be calculated using non-compartmental analysis. Only plasma and urine concentrations greater than the lower limits of quantitation (LOQ, 5 ng/mL in plasma and urine) for the assays will be used in the pharmacokinetic analysis.

| | 30 mg/kg | 40 mg/kg | 50 mg/kg | 60 mg/kg |
|---|---|---|---|---|
| Cmax, ng/mL | 68171 ± 17502 | 87900 ± 14992 | 91714 ± 18793 | 104133 ± 36734 |
| Tmax, h | 1.00 | 1.38 | 1.50 | 1.25 |
| $AUC_{inf}$, ng·h/mL | 160828 ± 24149 | 194617 ± 67338 | 235883 ± 58304 | 227160 ± 44663 |
| t½ h | 12.1 ± 3.05 | 18.6 ± 19.2 | 12.8 ± 7.66 | 8.44 ± 3.83 |
| CL/F, mL/min | 239 ± 17.2 | 290 ± 73.8 | 286 ± 56.1 | 381 ± 55.8 |
| $V_z$/F, L | 248 ± 58.8 | 542 ± 657 | 338 ± 272 | 285 ± 159 |
| CLr, mL/min | 139 ± 13.2 | 152 ± 18.0 | 103 ± 16.2 | 146 ± 34.4 |

Example 8

Single-Dose Study in Healthy Human Subjects

Example 8 was a double-blind, placebo-controlled single dose-escalating study in healthy subjects. Men between the ages of 18-45 years qualified to participate if they were able to voluntarily give consent and had no clinically significant abnormal findings at the screening evaluation. Specifically, subjects had blood pressure in the normal range, ECG and clinical laboratory values within normal limits, tested negative for drugs of abuse and had not recently donated blood. Subjects were also HIV, Hepatitis B, and Hepatitis C negative and agreed to use an approved method of contraception during the study.

The objectives of this study were to assess the safety, tolerability, and pharmacokinetics of ascending single doses of Compound 1 compared to placebo. Additionally, dose proportionality and pharmacodynamics of Compound 1 were assessed. Four doses of Compound 1 (3, 6, 10, and 16 mg/kg), in capsule form, were evaluated in this study. Following screening, subjects in a given cohort were randomly assigned to receive either Compound 1 or placebo. In the first cohort, 3 subjects received Compound 13 mg and 2 received placebo; in each of the subsequent remaining 3 cohorts, 3 subjects received the next higher dose of Compound 1 and 1 received placebo. Subjects were dosed and then confined to the clinical research unit for 24 hours to conduct safety and pharmacokinetic assessments. Subjects were released from the clinic on Day 2 and returned daily for follow-up visits for 5 days post-dosing.

All 12 subjects who received a dose of Compound 1 were included in the analysis of pharmacokinetic parameters. All 17 subjects enrolled in the study were included in the analysis of pharmacodynamics.

Plasma Concentration Data

Blood samples for determination of total (free and iron bound complex) plasma Compound 1 concentrations were collected on Day 1 at pre-dose (within 60 minutes prior to dose administration) and then at 0.25, 0.5, 0.75, 1, 1.5, 2, 2.5, 3, 3.5, 4, 8, 12 hours post-dose; on Day 2 at 24 and 36 hours post-dose; on Day 3 at 48 hours post-dose, on Day 4 at 72 hours post-dose; and on Day 5 at 96 hours post-dose.

Urine Concentration Data

Total urine collection for pharmacokinetic and pharmacodynamic assessment was performed at pre-dose and then for intervals 0-4, 4-8, 8-12, 12-24 hours post-dose. Collection of total urine for 24 hours post-dose for pharmacokinetic analysis was complete for all subjects who received a dose of Compound 1. It was noted, however, that Subject R105 (placebo) voided into the toilet once (at 3 minutes post-dose) during the 0-4 hour post-dose urine collection interval.

Pharmacokinetic Parameters

Plasma Pharmacokinetic Parameters

The plasma pharmacokinetic parameters are summarized in Table 16. Apparent terminal elimination rate was able to be determined for 11 of 12 subjects, with mean $t_{1/2}$ of 12.8 hours (standard deviation 10.1, median 7.32), ranging from 3.77-35.2 hours. From the concentration-time profiles, elimination appeared to be biphasic in some subjects. No specific modeling was performed.

TABLE 16

Plasma Pharmacokinetic Parameters

| Dose Level | Number of Subjects | $T_{max}$ hr | $C_{max}$ ng/mL | $AUC_{0-t}$ ng · hr/mL | $t_{1/2}$ hr | $k_{el}$ 1/hr | $AUC_{0-24}$ ng · hr/mL | $AUC_{0-\infty}$ ng · hr/mL |
|---|---|---|---|---|---|---|---|---|
| 3 mg/kg Cohort 1 | 3 | 1.33 (0.29) | 5413 (1040) | 12104 (968) | 4.40 (0.56) | 0.1595 (0.0216) | 12104 (968) | 12158 (959) |
| 6 mg/kg Cohort 2 | 3 | 0.92 (0.52) | 12233 (2026) | 25261 (3042) | 15.44 (4.46) | 0.0469 (0.0315) | 24720 (2931) | 26626 (3126) |
| 10 mg/kg Cohort 3 | 3 | 1.17 (0.29) | 16633 (1656) | 43391 (5029) | 16.12 (8.73) | 0.0562 (0.0378) | 42692 (4724) | 43587 (4907) |
| 16 mg/kg Cohort 4 | 3 | 1.00 (0.00) | 34833 (18911) | 75418 (29048) | 16.12 (16.57) | 0.0779 (0.0519) | 74620 (29633) | 75566 (28927) |

$AUC_{0-24}$ = area under the drug concentration-time curve from time 0 to 24 hours; $AUC_{0-t}$ = area under the drug concentration-time curve from time 0 to last sampling time; $AUC0-\infty$ = area under the drug concentration-time curve from time 0 to infinity; $C_{max}$ = maximum drug concentration; $K_{el}$ = elimination rate constant; $t_{1/2}$ = apparent terminal-phase disposition half-life; $t_{max}$ = time to $C_{max}$.

Urine Pharmacokinetic Parameters

The total fraction of administered drug excreted in urine over the 24 hour post-dose period ranged from 19-83% across all 4 dose levels (average 59%, standard deviation 18%) without apparent relation to dose.

Dose Dependence

Figure 9:
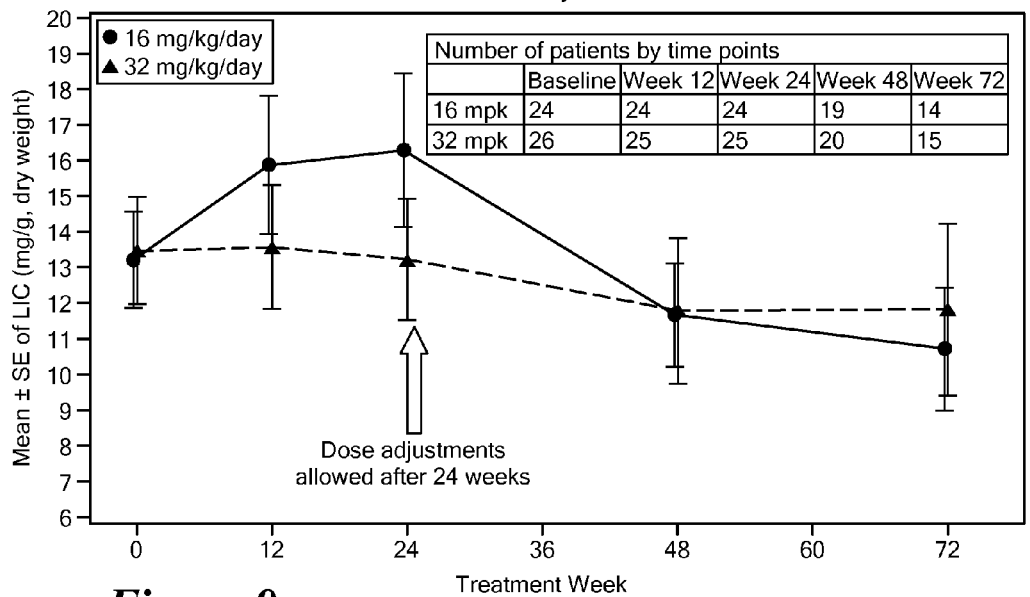
FIG. 9. Exemplary summary of liver iron concentration (LIC) by treatment group and week.

Mean $C_{max}$ and $AUC_{0-24}$ by dose level is presented graphically in FIG. 9. The primary Y axis is $C_{max}$ (ng/mL), while the secondary axis (to the right) is $AUC_{0-t}$ (ng·hr/mL). Each symbol is the mean of 3 individual subject values, error bars are standard deviations.

The mean trend appears linear across the dose range for both parameters.

Example 9

Single-Dose Study—Healthy Human Subjects

Example 9 was a single-dose escalating study in healthy volunteers. The objectives of the study were to assess the safety, tolerability, pharmacokinetic, and pharmacodynamics of single ascending doses of Compound 1. The doses tested were 30, 40, 50, 60, and 75 mg/kg once daily and a regimen of 20 mg/kg twice a day, which extended the range of doses evaluated. This Example confirms the earlier results obtained with higher dosage, as described in Example 7.

This was a single-center, double-blind, placebo-controlled study of ascending single oral doses of Compound 1. Six cohorts of 8 subjects (30 and 50 mg/kg single doses) or 5 subjects (40, 60, and 75 mg/kg single doses and 20 mg/kg×2 doses at 12 hour intervals) were dosed sequentially with Compound 1. Within each cohort, 7 or 4 subjects received Compound 1 and 1 subject received placebo. Subjects in the 20 mg/kg×2 doses cohort received a dose the evening prior to the study day (Day −1), approximately 12 hours prior to dosing on Day 1. The dose administered on Day −1 followed a 2-hour fast and that on Day 1 a 10-hour fast.

A total of 36 subjects were enrolled and all subjects completed the study. The 30 subjects that received active drug comprised the pharmacokinetic (PK) analysis population.

Individual Subject Concentration Data

Plasma Concentration Data

Four subjects receiving a single dose, blood samples for the measurement of the total (free and iron bound complex) plasma concentrations of Compound 1 were collected before and 0.25, 0.5, 0.75, 1, 1.25, 1.5, 2, 2.5, 4, 8, 12, 24, 48, 72, and 96 hours after dosing. Subjects receiving two doses of 20 mg/kg had blood collected prior and 0.5, 1, 1.5, 2, and 2.5 hours after the first dose. After the second dose in the morning of Day 1, the sampling schedule was identical to that used for subjects receiving a single dose.

Urine Concentration Data

In all cohorts, urine was collected in pooled intervals of 0-4, 4-8, 8-12 and 12-24 hours after the dose on Day 1 for the analysis of Compound 1 concentrations.

Pharmacokinetic Parameters

Plasma Pharmacokinetic Parameters

Plasma pharmacokinetic parameters are presented in Table 17. The median values for $T_{max}$ ranged from 1.00 to 1.50 hours and the $t_{1/2}$ ranged from 8.36 h to 18.6 hours; neither appeared to be dependent on dose. The mean values for CL/F, Vz/F, $t_{1/2}$, and CLr for the 20 mg/kg×2 cohort were in good agreement with those for the 40 mg/kg cohort and for the other single dose cohorts.

Urine Pharmacokinetic Parameters

After administration of 30 and 40 mg/kg, approximately 55% of the dose was recovered in the urine over the 24-hour post-dose period; this dropped to approximately 38% for the 3 higher doses. Renal clearance averaged approximately 140 mL/min and was not dependent upon dose. Although there seems to be a component of active secretion to the renal excretion of Compound 1, there is no apparent saturation over the range of doses and systemic exposures observed in this study.

Example 10

Efficacy Study in Human Subjects

In this Example, the safety and efficacy of Compound 1 in adults with transfusional iron overload over 48 weeks of treatment was assessed. Diagnosis and transfusional iron burden of patients (including Asians, Blacks/African Americans, and Whites) at randomization are as follows: 38 patients diagnosed with β-thalassemia major, 2 patients diagnosed with α-thalassemia major, 2 diagnosed with β-thalassemia intermedia (transfusion>7/year), 6 diagnosed with HbE-β thalassemia, and 3 diagnosed with Sickle cell disease. The patients were divided into two dosing groups: 14.5 mg/kg/day and 29 mg/kg/day. Average liver iron content at baseline (mg/g dry weight) was 13.2 with SD 6.64 for the 14.5 mg/kg/day dosing group and 13.9 with SD 7.82 for the 29 mg/kg/day dosing group. Median serum ferritin (ng/ml) was 2564 for the 14.5 mg/kg/day dosing group and 2624 for the 29 mg/kg/day dosing group. Mean pre-transfusion average haemoglobin of previous 3 transfusions (g/dL) was 9.6 (with SD of 0.56) for the 14.5 mg/kg/day dosing group and 9.8 (with SD of 0.79)

TABLE 17

Plasma Pharmacokinetic Parameters

| Parameter | Dose (mg/kg) | | | | | |
|---|---|---|---|---|---|---|
| | 30 | 40 | 50 | 60 | 75 | 20 × 2 [b] |
| | Mean ± SD (N) [a] | | | | | |
| $C_{max}$ (ng/mL) | 68,171 ± 17,502 (7) | 87,900 ± 14,992 (4) | 91,714 ± 18,793 (7) | 82,325 ± 52,934 (4) | 84,575 ± 52,609 (4) | 52,900 ± 20,693 (4) |
| $t_{max}$ (h) | 1.00 (7) | 1.38 (4) | 1.50 (7) | 1.38 (4) | 1.38 (4) | 0.75 (4) |
| $AUC_{(0-t)}$ (h·ng/mL) | 154,764 ± 24,324 (7) | 205,342 ± 59,685 (4) | 253,997 ± 90,414 (7) | 204,471 ± 58,032 (4) | 244,418 ± 132,356 (4) | 221,100 ± 71,902 (4) |
| $AUC_{inf}$ (h·ng/mL) | 160,828 ± 24,149 (5) | 194,617 ± 67,338 (3) | 235,883 ± 58,304 (4) | 204,758 ± 57,754 (4) | 246,714 ± 162,189 (3) | 230,827 ± 84,875 (3) |
| $\lambda_Z$ (h$^{-1}$) | 0.0615 ± 0.0200 (5) | 0.0677 ± 0.0439 (3) | 0.0664 ± 0.0292 (4) | 0.0786 ± 0.0393 (4) | 0.0943 ± 0.0383 (3) | 0.0744 ± 0.0158 (3) |
| $t_{1/2}$ (h) | 12.1 ± 3.05 (5) | 18.6 ± 19.2 (3) | 12.8 ± 7.66 (4) | 11.0 ± 5.99 (4) | 8.36 ± 3.84 (3) | 9.64 ± 2.28 (3) |
| CL/F (mL/min) | 239 ± 17.2 (5) | 290 ± 73.8 (3) | 286 ± 56.1 (4) | 435 ± 117.0 (4) | 540 ± 237 (3) | 235 ± 96.2 (3) |
| $V_Z$/F (L) | 248 ± 58.8 (5) | 542 ± 657 (3) | 338 ± 272 (4) | 454 ± 363 (4) | 342 ± 83.6 (3) | 208 ± 136 (3) |
| $Ue_{(0-24)}$ (mg) | 1,260 ± 255.3 (7) | 1,820 ± 397 (4) | 1,500 ± 434 (7) | 1,713 ± 480 (4) | 2,199 ± 1,189 (4) | 805 ± 208 (4) |
| $Fe_{(0-24)}$ (% Dose) | 54.8 ± 8.99 (7) | 57.1 ± 8.60 (4) | 40.2 ± 8.69 (7) | 33.7 ± 8.37 (4) | 35.0 ± 15.1 (4) | NC [c] |
| CLr (mL/min) | 139 ± 13.2 (7) | 152 ± 18.0 (4) | 103 ± 16.2 (7) | 147 ± 28.2 (4) | 165 ± 42.7 (4) | 131 ± 18.7 (4) |

[a] Arithmetic mean ± standard deviation (N), except $t_{max}$ for which the median (N) is reported.
[b] The 2 doses were given at 12-hour intervals, the first the evening of Day −1 and the second the morning of Day 1. $AUC_{(0-t)}$ and $AUC_{inf}$ are for the total dose of 40 mg/kg, which was also used to calculate CL/F and Vz/F. $C_{max}$ represents the maximum concentration and $t_{max}$ the time of $C_{max}$ for the second dose.
[c] Parameter could not be estimated due to the carryover of drug from the dose administered 12 hours previously on Day −1.

Figure 5:
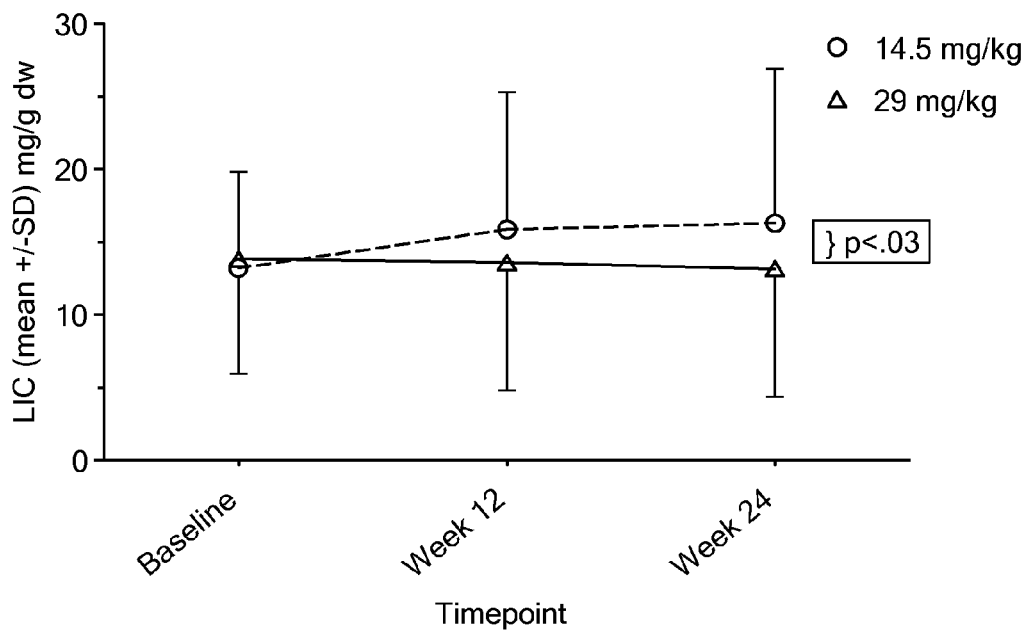
FIG. 5. Exemplary LIC in patients in the first 24 weeks of treatment.
Figure 6:
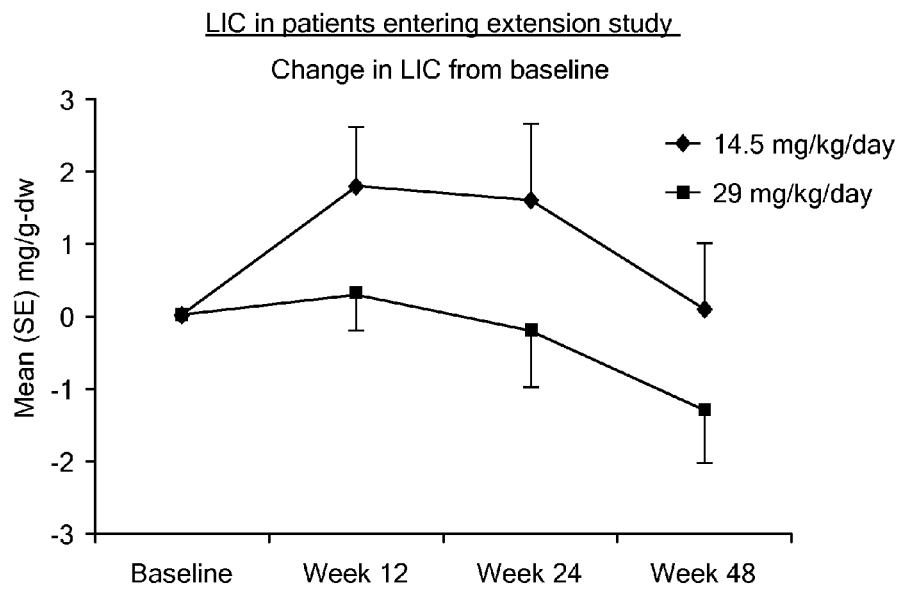
FIG. 6. Exemplary LIC in patients entering extension study.
Figure 7:
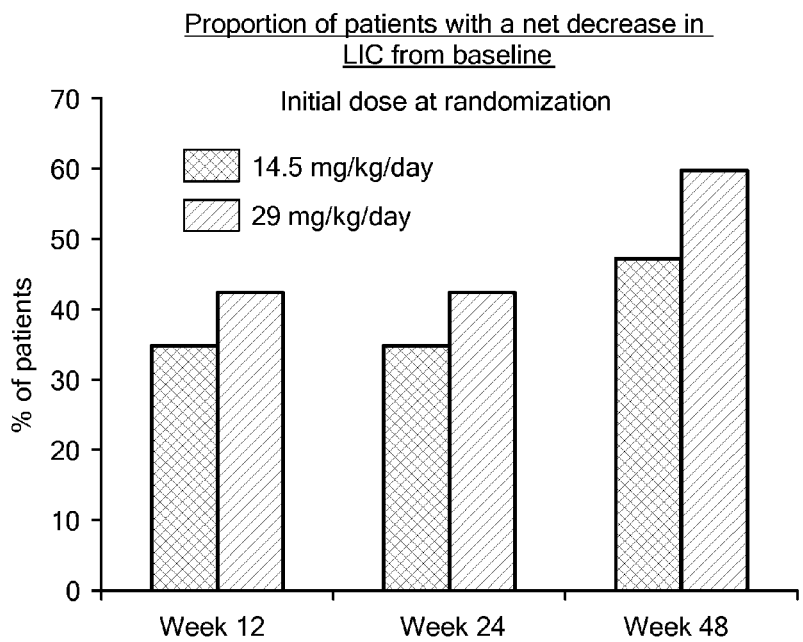
FIG. 7. Exemplary results illustrating proportion of patients with a net decrease in LIC from baseline.
Figure 8:
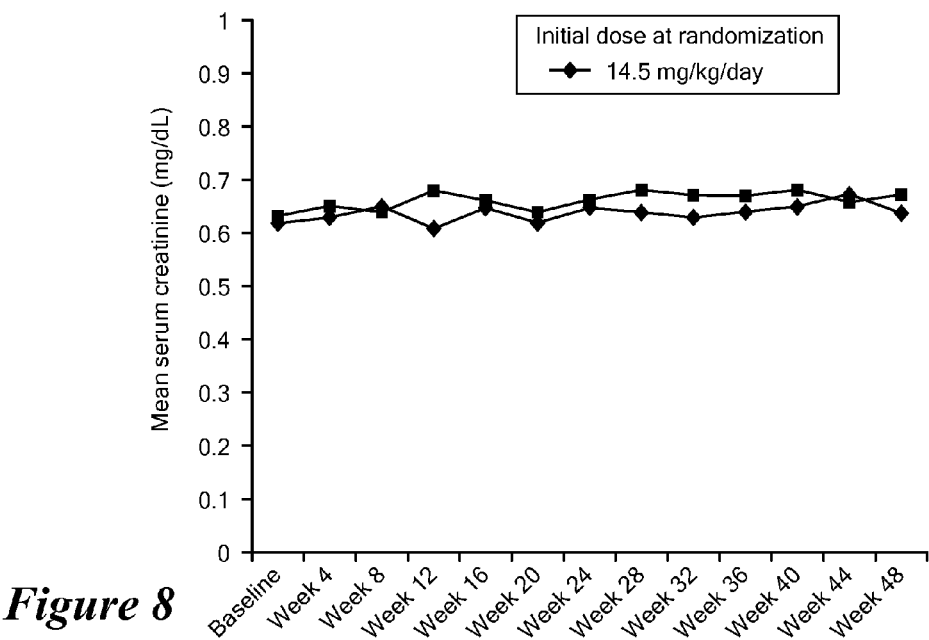
FIG. 8. Exemplary results illustrating serum creatinine in extension population.

$AUC_{(0-t)}$ = area under the plasma concentration-time curve from time 0 to time t; $AUC_{inf}$ = area under the plasma concentration-time curve from time 0 to infinity; CL/F = apparent oral-dose clearance; CLr = renal clearance; $C_{max}$ = maximum plasma concentration; $Fe_{(0-24)}$ = fraction excreted from time 0 to 24 h; $\lambda_Z$ = terminal-phase disposition rate constant; NC = not calculated; SD = standard deviation; $t_{1/2}$ = apparent terminal-phase disposition half-life; $t_{max}$ = time to $C_{max}$; $Ue_{(0-24)}$ = urinary excretion from time 0 to 24 h; $V_Z$/F = apparent volume of distribution.

for the 29 mg/kg/day dosing group. Mean daily transfusion iron intake (mg/kg/d) was about 0.36 (ranging 0.22-0.84) for the 14.5 mg/kg/day dosing group and 0.38 (ranging 0.17-0.60) for the 29 mg/kg/day dosing group. Exemplary results of LIC in patients in the first 24 weeks of treatment are shown in Table 18 and FIG. 5. Exemplary results of LIC in patients entering extension study are shown in Table 19 and FIG. 6. See also FIGS. 7 and 8.

TABLE 18

|  | 14.5 mg/kg | 29 mg/kg | P value |
|---|---|---|---|
| Mean net change in hepatic iron (mg/g-dw) | 3.1 | −0.3 | <0.03 |
| % with net iron reduction | 29 | 44 | NS |

TABLE 19

| Initial dose at randomization | Baseline | Week 12 | Week 24 | Week 48 |
|---|---|---|---|---|
| 14.5 mg/kg/day | 11.9 (1.32) | 13.7 (1.74) | 13.6 (1.94) | 11.7 (1.46) |
| 29 mg/kg/day | 13.0 (1.75) | 13.6 (2.04) | 12.8 (1.79) | 11.8 (2.04) |

Example 11

Additional Efficacy Study in Human Subjects

The goal of this experiment was to: 1. evaluate the safety and tolerability based on clinical assessments of two doses (16 and 32 mg/kg/d) of Compound 1 when administered daily for 24 weeks to patients with transfusional iron overload; 2. identify a differential response between dose groups in liver iron concentration determined by magnetic resonance imaging (MRI) after 24 weeks of dosing; and 3. assess the safety and efficacy activity of Compound 1 when administered daily for up to 96 weeks.

This experiment is an open-label, randomized study of two dose levels (16 and 32 mg/kg/d) of Compound 1 administered once daily for 24 weeks to eligible patients with transfusional iron overload requiring chelation therapy, with a dosing extension of 72 additional weeks.

Patients were assigned to one of two strate: "high" or "low" transfusion burden based on the average iron intake of the six transfusion sessions. Patients within each transfusion burden groups were randomized to one of two Compound 1 treatment arms: 16 mg/kg/d (16 mpk) or 32 mg/kg/d (32 mpk). The stratification followed by randomization to treatment arms helps to ensure an equal distribution of patients with "high" and "low" transfusion burdens to the high or low dose of Compound 1. Each treatment arm received one dose of Compound 1 daily for 24 weeks.

At the conclusion of the 24 week dosing period, patients who qualify and consent to continue treatment continued for an additional 72 weeks of Compound 1 dosing.

The inclusion of 25 patients in each treatment group provided a statistical power of 0.80 to detect, within 6 months, an LIC difference (normalized for initial LIC) of 3 mg/g dry weight between the two dose groups as determined by MRI. Baseline characteristics between dose groups were compared using Fisher extract test or Wilcoxon rank sum test as appropriate. The change in baseline to week 12, 24, and 72 values for all pharmacodynamics parameters were analyzed by an ANCOVA model with main effect for treatment group with baselines value for the corresponding parameters and transfusion burdon (iron input) during the study and baseline liver iron concentration as covariates comparing the two active treatment groups. T2* values were natural log transformed and summarized as the geometric mean (the antilog of the mean of the log data) plus or minus the co-efficient of variation (CV) defined as square root of eMSE where MSE is defined as the mean square error and subject to ANCOVA setting the p value as the threshold for statistical significance at 0.05 (confidence level of 95%).

The patient population diagnoses results are provided in Table 20.

TABLE 20

| Diagnosis (n, %) | 16 mpk (N = 24) | 32 mpk (N = 27) | Total (N = 51) |
|---|---|---|---|
| β-thalassemia major | 18 (75) | 20 (74) | 38 (75) |
| α-thalassemia major | 1 (4.2) | 1 (3.7) | 2 (4) |
| β-thalassemia intermedia (transfusion >7/year) | 1 (4.2) | 1 (3.7) | 2 (4) |
| HbE-β thalassemia | 2 (8.3) | 4 (14.8) | 6 (12) |
| Sickle cell disease | 2 (8.3) | 1 (3.7) | 3 (6) |

Exemplary results are provided in Tables 21-27, and are summarized in FIG. 9. The LIC in patients receiving 16 mpk demonstrated a statistically significant increase from baseline to Weeks 12 and 24. The LIC in patients receiving 32 mpk remained relatively unchanged from baseline at the first 24 weeks. A clear dose-response in the iron chelating capacity of Compound 1 was observed between 16 and 32 mpk during the first 24-weeks of the study.

Doses of 32 mpk and greater demonstrate a reduction in LIC from Week 24. Subjects initially treated with 16 mpk who entered the extension phase and received a dose increase reduced their LIC to baseline levels over the next 24 weeks (By Week 48).

TABLE 21

Summary of R2 Liver Iron Concentration (per FerriScan MRI); 12 weeks

| Time Point | Compound 1 16 mg/kg/d (N = 24) | Compound 1 32 mg/kg/d (N = 26) | Total (N = 50) |
|---|---|---|---|
| Baseline[2] | | | |
| N | 24 | 26 | 50 |
| Mean (SD) | 13.23 (6.639) | 13.49 (7.736) | 13.36 (7.158) |
| SE | 1.355 | 1.517 | 1.012 |
| Median | 11.85 | 11.30 | 11.55 |
| Min, Max | 4.30, 24.50 | 3.90, 30.20 | 3.90, 30.20 |
| CV(%) | 50.20 | 57.33 | 53.56 |
| Week 12 | | | |
| N | 24 | 25 | 49 |
| Mean (SD) | 15.90 (9.446) | 13.59 (8.684) | 14.72 (9.046) |
| SE | 1.928 | 1.737 | 1.292 |
| Median | 11.70 | 10.70 | 11.10 |
| Min, Max | 4.80, 34.60 | 4.60, 34.20 | 4.60, 34.60 |
| CV(%) | 59.41 | 63.91 | 61.45 |
| p-value[3] | 0.0037 | 0.7058 | 0.0294 |
| Change from Baseline to Week 12 | | | |
| N | 24 | 25 | 49 |
| Mean (SD) | 2.68 (4.050) | −0.22 (2.827) | 1.20 (3.740) |
| SE | 0.827 | 0.565 | 0.534 |
| Median | 0.90 | 0.10 | 0.70 |
| Min, Max | −4.50, 10.80 | −6.90, 4.40 | −6.90, 10.80 |
| CV(%) | 151.41 | −1308.96 | 311.68 |

TABLE 22

Summary of R2 Liver Iron Concentration (per FerriScan MRI); 24 weeks

| Time Point | Compound 1 16 mg/kg/d (N = 24) | Compound 1 32 mg/kg/d (N = 26) | Total (N = 50) |
|---|---|---|---|
| Week 24 | | | |
| N | 24 | 25 | 49 |
| Mean (SD) | 16.31 (10.570) | 13.25 (8.510) | 14.75 (9.599) |
| SE | 2.158 | 1.702 | 1.371 |
| Median | 11.50 | 9.30 | 11.00 |
| Min, Max | 4.60, 37.40 | 3.40, 30.80 | 3.40, 37.40 |
| CV(%) | 64.81 | 64.24 | 65.09 |
| p-value[3] | 0.0122 | 0.7889 | 0.0850 |
| Change from Baseline to Week 24 | | | |
| N | 24 | 25 | 49 |
| Mean (SD) | 3.08 (5.552) | −0.27 (4.950) | 1.37 (5.467) |
| SE | 1.133 | 0.990 | 0.781 |
| Median | 1.10 | 0.20 | 0.50 |
| Min, Max | −4.90, 19.00 | −8.60, 13.80 | −8.60, 19.00 |
| CV(%) | 180.08 | −1846.88 | 398.04 |
| Week 48 | | | |
| N | 19 | 20 | 39 |
| Mean (SD) | 11.68 (6.369) | 11.81 (9.145) | 11.74 (7.813) |
| SE | 1.461 | 2.045 | 1.251 |
| Median | 9.30 | 7.70 | 8.80 |
| Min, Max | 4.40, 27.40 | 2.40, 31.80 | 2.40, 31.80 |
| CV(%) | 54.54 | 77.47 | 66.53 |
| p-value[3] | 0.9237 | 0.0788 | 0.2831 |

TABLE 23

Summary of R2 Liver Iron Concentration (per FerriScan MRI); 72 weeks

| Time Point | Compound 1 16 mg/kg/d (N = 24) | Compound 1 32 mg/kg/d (N = 26) | Total (N = 50) |
|---|---|---|---|
| Change from Baseline to Week 48 | | | |
| N | 19 | 20 | 39 |
| Mean (SD) | 0.09 (4.015) | −1.32 (3.177) | −0.63 (3.632) |
| SE | 0.921 | 0.711 | 0.582 |
| Median | 0.00 | −0.90 | −0.20 |
| Min, Max | −9.00, 8.90 | −8.00, 4.40 | −9.00, 8.90 |
| CV(%) | 4487.31 | −240.72 | −573.52 |
| Week 72 | | | |
| N | 14 | 15 | 29 |
| Mean (SD) | 10.74 (6.373) | 11.84 (9.307) | 11.31 (7.904) |
| SE | 1.703 | 2.403 | 1.468 |
| Median | 9.40 | 8.70 | 8.70 |
| Min, Max | 3.90, 26.00 | 1.40, 31.90 | 1.40, 31.90 |
| CV(%) | 59.36 | 78.61 | 69.91 |
| p-value[3] | 0.6024 | 0.2468 | 0.4594 |
| Change from Baseline to Week 72 | | | |
| N | 14 | 15 | 29 |
| Mean (SD) | 0.52 (3.654) | −1.83 (5.853) | −0.69 (4.975) |
| SE | 0.977 | 1.511 | 0.924 |
| Median | 0.50 | −1.80 | −0.80 |
| Min, Max | −6.10, 5.80 | −15.70, 9.20 | −15.70, 9.20 |
| CV(%) | 700.79 | −320.41 | −717.83 |

TABLE 24

Response Rate (Reduction from Baseline) of R2 Liver Iron Concentration

| Study Day | Statistic | Compound 1 16 mg/kg/d (N = 24) | Compound 1 32 mg/kg/d (N = 26) | Overall (N = 50) | p-value[1] |
|---|---|---|---|---|---|
| Week 12 | n | 24 | 25 | 49 | 0.2436 |
| | Responder | 7 (29.2%) | 12 (48.0%) | 19 (38.8%) | |
| | Non-responder | 17 (70.8%) | 13 (52.0%) | 30 (61.2%) | |
| Week 24 | n | 24 | 25 | 49 | 0.3772 |
| | Responder | 7 (29.2%) | 11 (44.0%) | 18 (36.7%) | |
| | Non-responder | 17 (70.8%) | 14 (56.0%) | 31 (63.3%) | |
| Week 48 | n | 19 | 20 | 39 | 0.5273 |
| | Responder | 9 (47.4%) | 12 (60.0%) | 21 (53.8%) | |
| | Non-responder | 10 (52.6%) | 8 (40.0%) | 18 (46.2%) | |
| Week 72 | n | 14 | 15 | 29 | 0.1431 |
| | Responder | 5 (35.7%) | 10 (66.7%) | 15 (51.7%) | |
| | Non-responder | 9 (64.3%) | 5 (33.3%) | 14 (48.3%) | |

TABLE 25

Response Rate (at Least 10% Reduction from Baseline) of R2 Liver Iron Concentration

| Study Day | Statistic | Compound 1 16 mg/kg/d (N = 24) | Compound 1 32 mg/kg/d (N = 26) | Overall (N = 50) | p-value[1] |
|---|---|---|---|---|---|
| Week 12 | n | 24 | 25 | 49 | 0.0738 |
| | Responder | 2 (8.3%) | 8 (32.0%) | 10 (20.4%) | |
| | Non-responder | 22 (91.7%) | 17 (68.0%) | 39 (79.6%) | |
| Week 24 | n | 24 | 25 | 49 | 0.1137 |
| | Responder | 4 (16.7%) | 10 (40.0%) | 14 (28.6%) | |
| | Non-responder | 20 (83.3%) | 15 (60.0%) | 35 (71.4%) | |
| Week 48 | n | 19 | 20 | 39 | 0.1908 |
| | Responder | 5 (26.3%) | 10 (50.0%) | 15 (38.5%) | |
| | Non-responder | 14 (73.7%) | 10 (50.0%) | 24 (61.5%) | |
| Week 72 | n | 14 | 15 | 29 | 0.2723 |
| | Responder | 5 (35.7%) | 9 (60.0%) | 14 (48.3%) | |
| | Non-responder | 9 (64.3%) | 6 (40.0%) | 15 (51.7%) | |

TABLE 26

Summary of Serum Ferritin

| Time Point | Compound 1 16 mg/kg/d (N = 24) | Compound 1 32 mg/kg/d (N = 26) | Total (N = 50) |
|---|---|---|---|
| Week 72 | | | |
| N | 14 | 17 | 31 |
| Mean (SD) | 2873.93 (1686.925) | 3026.82 (1772.430) | 2957.77 (1707.219) |
| SE | 450.850 | 429.877 | 306.626 |
| Median | 2544.50 | 2396.00 | 2398.00 |
| Min, Max | 631.00, 7037.00 | 666.00, 5798.00 | 631.00, 7037.00 |
| Geometric Mean | 2418.49 | 2441.03 | 2430.83 |
| CV (%) | 71.42 | 84.11 | 76.84 |
| Change from Baseline to Week 72 | | | |
| N | 14 | 17 | 31 |
| Mean (SD) | 233.21 (874.109) | −150.82 (1413.634) | 22.61 (1197.761) |
| SE | 233.616 | 342.857 | 215.124 |

TABLE 26-continued

Summary of Serum Ferritin

| Time Point | Compound 1 16 mg/kg/d (N = 24) | Compound 1 32 mg/kg/d (N = 26) | Total (N = 50) |
|---|---|---|---|
| Median | 231.50 | −436.00 | −56.00 |
| Min, Max | −1522.00, 1614.00 | −2315.00, 2787.00 | −2315.00, 2787.00 |
| Geometric Mean | 1.14 | 0.89 | 0.99 |
| CV (%) | 42.42 | 64.48 | 56.06 |

TABLE 27

Incidence (%) of Subjects with Dose Adjustments

| Dose Adjustment | Compound 1 16 mg/kg/d (N = 24) | Compound 1 32 mg/kg/d (N = 27) |
|---|---|---|
| Up to Week 12 | 0 (0.0%) | 0 (0.0%) |
| Between Weeks 12-24 | 2 (8.3%) | 0 (0.0%) |
| Between Weeks 24-48 | 18 (75.0%) | 14 (51.9%) |
| Between Weeks 48-72 | 14 (58.3%) | 11 (40.7%) |

Example 11

Pharmacodynamics

Urine was collected for 24 hours following administration of Compound 1. There was no detectable iron in the urine across all doses—the lower limit of quantitation (LLOQ) of iron was approximately 195 μg/dL. In other studies, a more sensitive urinary iron assay was employed (LLOQ 10 μg/dL). Iron was detected in the urine of all subjects administered Compound 1 but no dose-dependent trends in excretion were apparent.

Conducted was a multicenter, randomized, open-label study of adult subjects with documented transfusional iron overload in need of chelation therapy. Transfusional iron overload was defined as LIC by R2 (FerriScan®) magnetic resonance imaging (MRI)≥3.5 mg/g liver dw or serum ferritin>500 ng/mL. Subjects received investigational product for 24 weeks with an extension of 72 weeks for the evaluation of long-term safety and efficacy. The 24-week and 48-week pharmacodynamics results are described in this section. A total of 51 subjects enrolled and 49 completed the initial 24-week treatment period.

Figure 3:
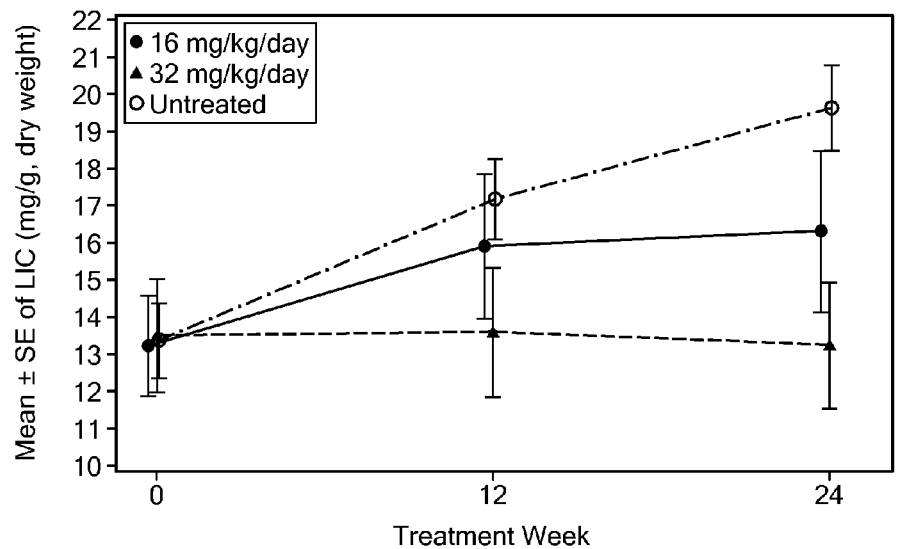
FIG. 3. Exemplary summary graph of liver ion concentration (LIC) by treatment group, 24 weeks.
Figure 14:
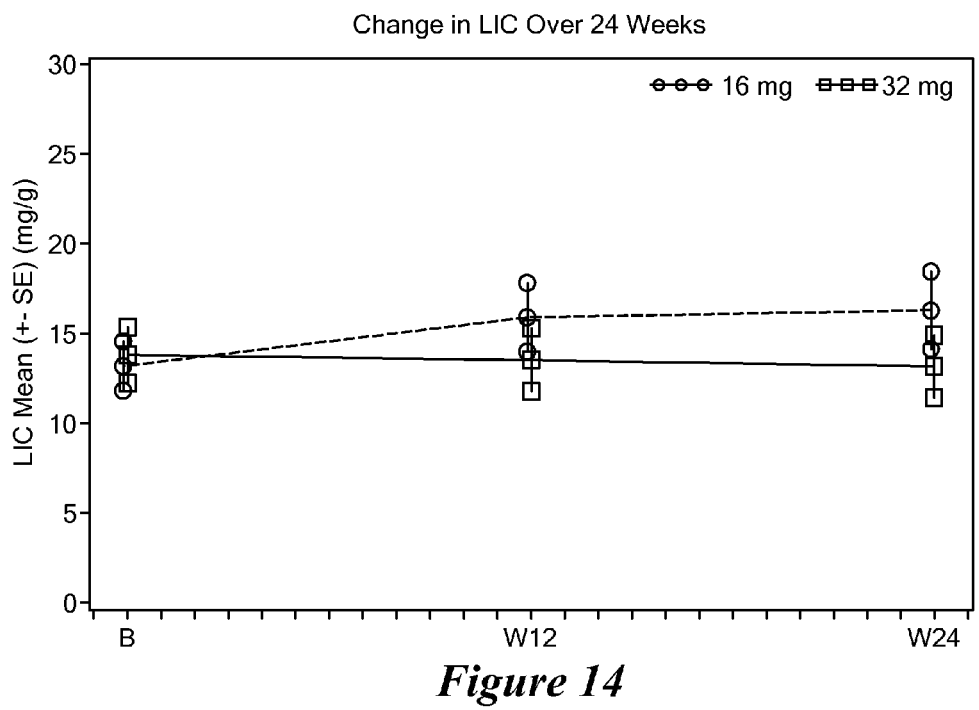
FIG. 14. Exemplary results illustrating change in LIC over 24 week treatment.

Twenty-four subjects in the low dose group (16 mg/kg/day) and 25 of the high dose group (32 mg/kg/day) had Baseline and Week 24 MRI (FerriScan®) assessments. The mean LIC for each treatment group at Baseline, Week 12, and Week 24 is shown in FIG. 14 (see also FIG. 3). In the low dose group, 7 of 24 had a lower LIC at 24 weeks compared with Baseline. The mean change in LIC in the low dose group was a net gain of 3.1 mg/g liver (dw). In the high dose group, 11 of 25 had a lower LIC at 24 weeks compared to Baseline. The mean change in LIC in the high dose group was −0.3 mg/g liver (dw). The difference in the mean change from baseline between treatment groups was 3.4 mg/g at 24 weeks. This difference was statistically significant (p<0.03).

Figure 4:
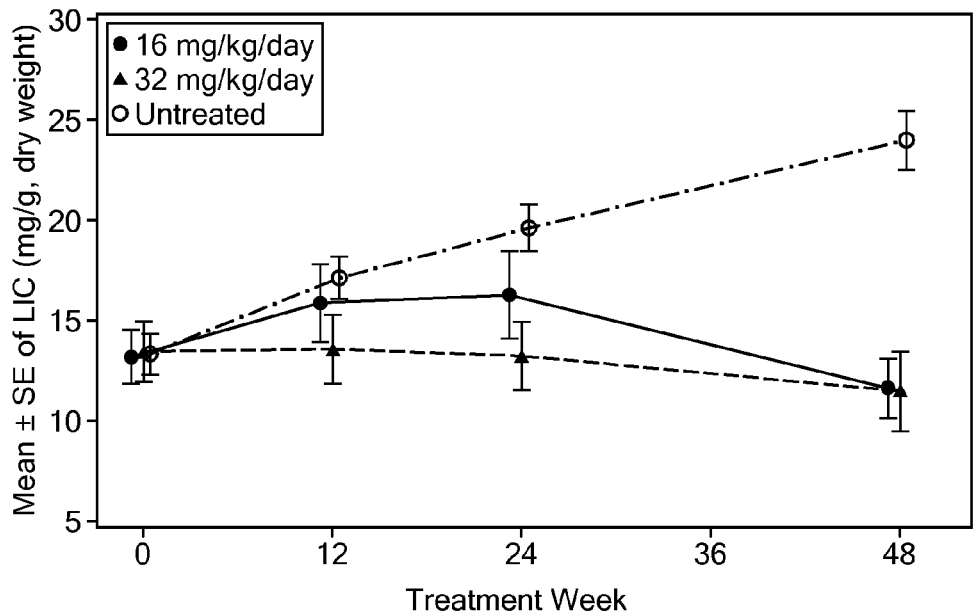
FIG. 4. Exemplary summary graph of liver ion concentration (LIC) by treatment group, 48 weeks.
Figure 15:
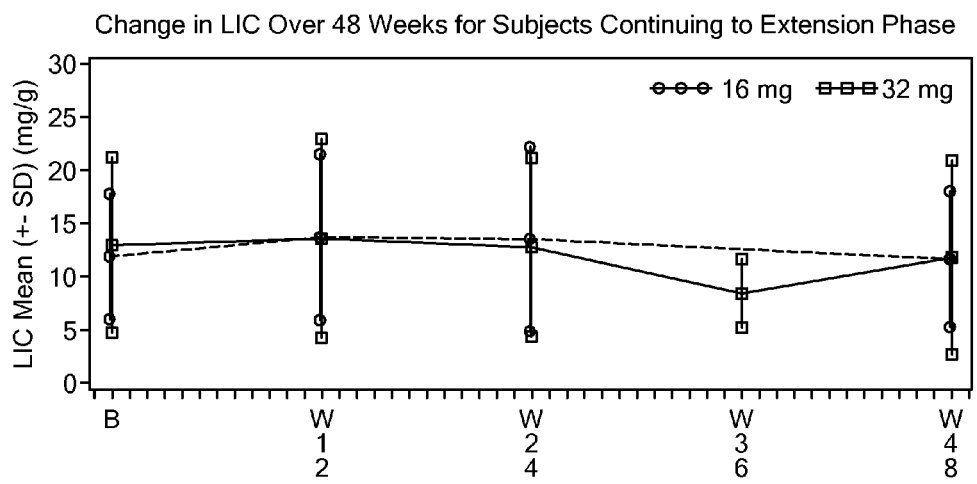
FIG. 15. Exemplary results illustrating change in LIC Over 48 week treatment.

Of the 49 subjects that completed through Week 24, 39 continued in the study for extended dosing through Week 48 (FIG. 15, see also FIG. 4). At Week 48, the 19 subjects randomized to 16 mg/kg/day showed a mean change from baseline LIC of 0.1 mg/g and the 20 subjects originally randomized to 32 mg/kg/day showed a mean change from baseline of −1.3 mg/g.

Example 12

Safety

Single-Dose Study in Healthy Subjects

All 17 enrolled subjects completed the study: Twelve received a single dose of Compound 1 (3, 6, 10, and 16 mg/kg) and 5 received placebo. Overall Compound 1 was well tolerated. There were no deaths, no serious adverse events (SAEs), and no withdrawals due to AEs. Treatment-emergent adverse events (TEAEs) were reported for 5 of the 12 subjects receiving Compound 1 (Table 28 and 29). A total of 9 AEs were reported; 8 treatment-emergent, and 1 pre-dose, all in subjects receiving Compound 1. While there were no AEs reported by subjects who received a placebo dose, there was no evidence to suggest a relationship between dose-escalation and the incidence, intensity or causality of AEs. Additionally, there were no clear differences in safety as evaluated by clinical laboratory assessments, vital sign measurements, and ECG parameters between subjects who had received Compound 1 compared with those who received placebo, and no apparent dose-related trends in these safety assessments in subjects who received Compound 1.

TABLE 28

| | Total (N = 51) N (%) |
|---|---|
| Any TEAE | 49 (96.1%) |
| TEAE Related to Investigational Product | 31 (60.8%) |
| TEAE Requiring Discontinuation of Study Drug | 14 (27.5%) |
| Serious TEAE | 5 (9.8%) |

TABLE 29

Incidence of All Adverse Events by Dose Group

| MedDRA System Organ Class | MedDRA Preferred Term | Treatment (mg/kg) | | | | | Total Number (%) Subjects with AEs |
|---|---|---|---|---|---|---|---|
| | | 3 | 6 | 10 | 16 | Placebo | All Treatments |
| Gastrointestinal disorders | Colitis | 0 | 0 | 0 | 1 (33%) | 0 | 1 (6%) |
| | Flatulence | 0 | 0 | 0 | 1 (33%) | 0 | 1 (6%) |
| | Gastroenteritis | 1 (33%) | 0 | 0 | | 0 | 1 (6%) |
| Infections and infestations | Upper respiratory tract infection | 0 | 1 (33%) | 0 | 0 | 0 | 1 (6%) |

TABLE 29-continued

Incidence of All Adverse Events by Dose Group

| MedDRA System Organ Class | MedDRA Preferred Term | Treatment (mg/kg) | | | | | Total Number (%) Subjects with AEs |
|---|---|---|---|---|---|---|---|
| | | 3 | 6 | 10 | 16 | Placebo | All Treatments |
| Musculoskeletal and connective tissue disorders | Arthralgia | 0 | 1 (33%) | | 0 | 0 | 1 (6%) |
| Nervous system disorders | Headache | 0 | 0 | 0 | 1 (33%) | 0 | 1 (6%) |
| | Somnolence | 1 (33%) | 0 | 0 | 0 | 0 | 1 (6%) |
| Total Number (%) of Subjects Experiencing Adverse Events: | | 1 (33%) | 1 (33%) | 0 | 3 (100%) | 0 (0%) | 5 (29%) |
| Total Number of Subjects Experiencing NO Adverse Events: | | 2 (67%) | 2 (67%) | 3 (100%) | 0 | 5 (100%) | 12 (71%) |
| Total Number of Subjects Receiving Treatment: | | 3 | 3 | 3 | 3 | 5 | 17 |

Figure 11:
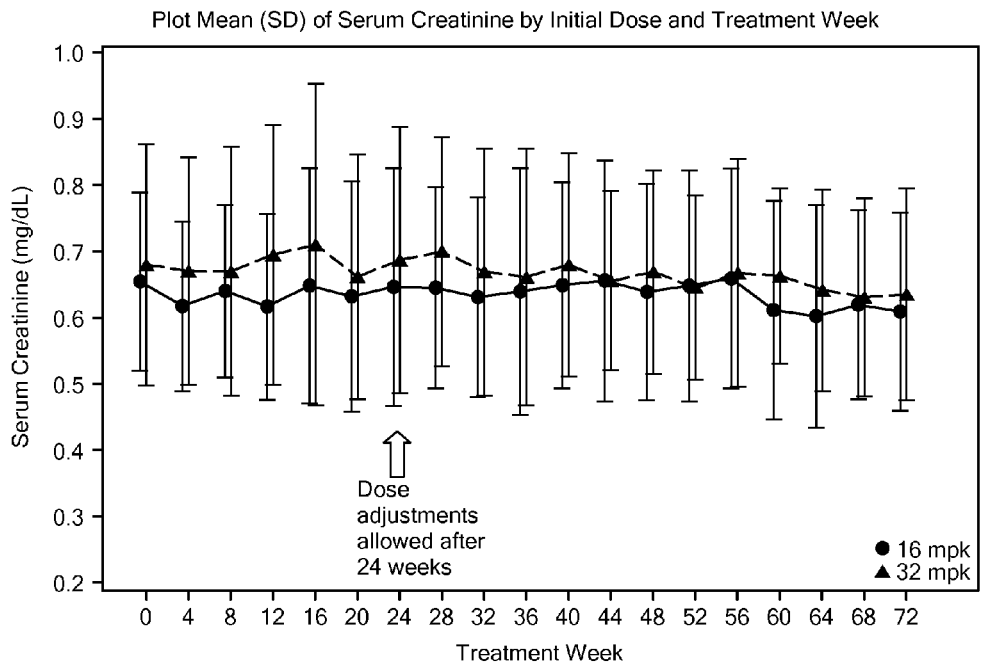
FIG. 11. Exemplary plot mean (SD) of serum creatinine by initial dose and treatment week.
Figure 12:
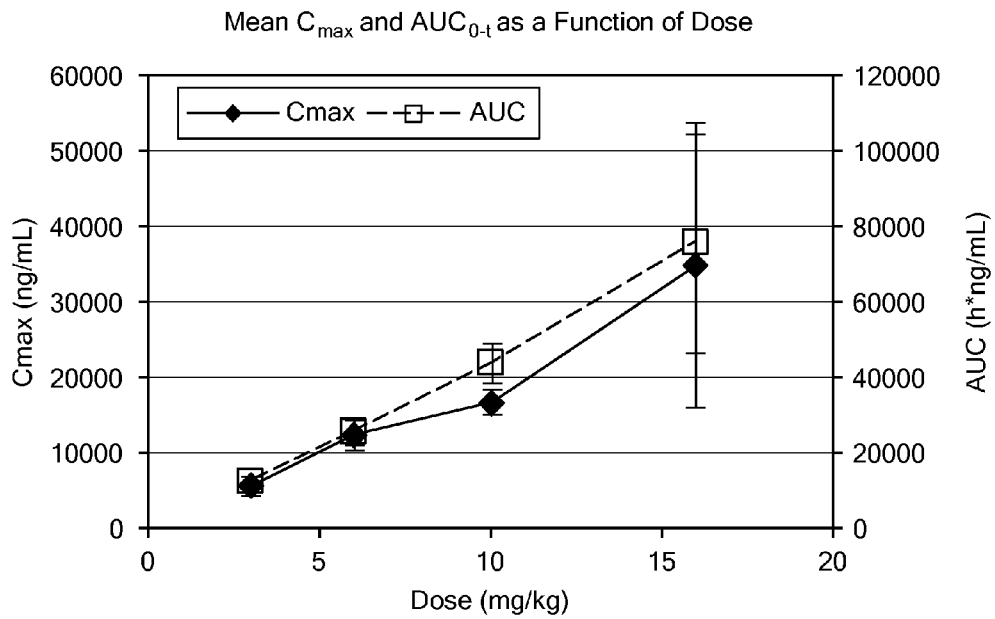
FIG. 12. Exemplary results illustrating mean $C_{max}$ and $AUC_{0-t}$ as a function of dose.
Figure 13:
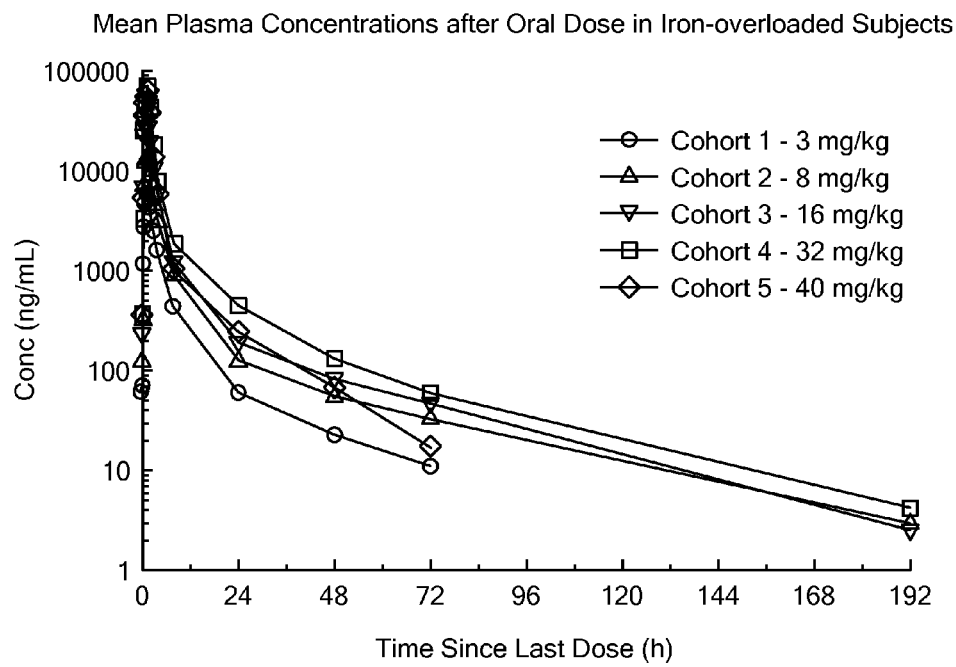
FIG. 13. Exemplary results illustrating mean plasma concentrations after oral dose in iron-overloaded subjects.

An exemplary summary of serum creatinine is provided in table 30 and FIG. 11. Compound 1 was generally well tolerated at doses tested (8-50 mg/kg/day). Mean serum creatinine did not change from baseline during the 72 week treatment period, and remained in the normal range. Elevations in transaminases were not significant.

TABLE 30

| | Total (N = 51) N (%) |
|---|---|
| Creatinine increase >33% and creatinine <=ULN at 2 consecutive post-baseline visits | 2 (3.9) |
| Creatinine increase >33% and creatinine >ULN at 2 consecutive post-baseline visits | 0 |
| Creatinine increase and creatinine >ULN at 2 consecutive post-baseline visits | 1 (2.0) |

Single-Dose Study in Healthy Subjects

Thirty-one subjects were enrolled and completed the study: 26 received a single oral dose of Compound 1 [30 (7 subjects), 40 (4 subjects), 50 (7 subjects), 60 (4 subjects) and 75 mg/kg (4 subjects)], 4 subjects previously administered a single dose at 30 and 40 mg/kg received 20 mg/kg bid and 5 received placebo. Overall Compound 1 was well tolerated. There were no deaths, SAEs), or withdrawals due to AEs. Treatment-emergent adverse events were reported for 13 of the 26 subjects receiving Compound 1 (50%). TEAEs in the active groups included catheter site erythema or hematoma (3 subjects), fatigue (1 subject), headache (2 subjects), dysgueusia (1 subject), presyncope (1 subject), abdominal pain (1 subject), nausea (1 subject), back pain (1 subject), muscle spasm (1 subject), decreased appetite (1 subject), chromaturia (1 subject).

All AEs reported after treatment with Compound 1 were of mild intensity. There were no apparent dose-related trends in AEs, changes in laboratory safety data including creatinine and blood urea nitrogen, physical examination and vital sign measurements, or 12-lead ECGs.

Single-Dose Phase 1 Study in Iron-Overloaded Subjects

Four iron overloaded subjects were enrolled and completed the study. Each subject received a single oral dose of Compound 1. Doses were 6, 10, 16 and 32 mg/kg. Overall, Compound 1 was well tolerated. There were no deaths, no serious adverse events (SAEs), and no withdrawals due to AEs. Three TEAEs were reported for a single subject who received 32 mg/kg of Compound 1. All 3 TEAEs occurred at the site of venipuncture used for blood sampling: bruising at cannula site on the left arm and bruising at 2 venipuncture sites on the left arm and then the right arm. There were no clinically significant changes in clinical laboratory assessments, vital sign measurements, or ECG parameters and no apparent dose-related trends in these safety assessments in subjects who received Compound 1.

Multiple-Dose Study—Iron-Overloaded Subjects

Twenty iron-overloaded subjects were enrolled and completed the study. Four subjects in each cohort were orally administered 3, 8, 16, or 32 or 40 mg/kg/day of Compound 1 for 7 consecutive days.

Compound 1 was generally well tolerated. All subjects completed the full course of treatment and no subject withdrew because of a TEAE. Although 90% of subjects experienced at least 1 TEAE, the majority of TEAEs were mild and unrelated to study drug. Urine color abnormal was the most frequently reported TEAE (8 subjects, 40%), and was determined to be related to study drug in all instances.

Additional TEAEs included: headache (5 subjects, 25%), flatulence (2 subjects, 10%), abdominal pain upper (1 subject, 5%), feeling hot (1 subject, 5%), tachycardia (1 subject, 5%), chromaturia (1 subject, 5%), pruritus (1 subject, 5%), blood urine present (1 subject, 5%), QT prolonged (1 subject, 5%), and dizziness (1 subject, 5%), were not dose dependent and resolved upon follow-up.

Many subjects entered the study with abnormal clinical laboratory measurements and showed changes in values over the course of treatment with Compound 1. However, there were no clear associations with treatment or dose and no changes were considered to be of clinical concern.

There were no clinically significant changes in vital signs, physical examinations or ECG, with the exception of one subject who had QTcB (not observed with QTcF) interval prolongation (20 msec) and concomitant increase of heart rate on Day 7 of treatment.

Only 1 SAE was recorded, in a subject receiving Compound 1 at a dose of 3 mg/kg/day who experienced sickle cell crisis with pain and was admitted to hospital 20 days after the last dose of Compound 1. This SAE was moderate in severity, expected due to the subject's underlying disease, resolved in 8 days, and was not related to treatment with Compound 1.

Study Comparing the Bioavailability and Pharmacokinetics of Oral Capsules Versus Oral Solution in Healthy Subjects This study was a study in healthy adult subjects designed to compare the bioavailability of Compound 1 when administered as an oral capsule or solution. 24 subjects were enrolled and 22 completed the study: Subjects received a single oral dose of 16 mg/kg of Compound 1 as an oral capsule or as a solution. Overall Compound 1 was well tolerated. There were no deaths, no SAEs, and no withdrawals as the result of an AE. Treatment-emergent AEs were reported for 14 of the 24 subjects receiving Compound 1 (58%). All AEs reported were of mild or moderate intensity. TEAEs included headache (3 subjects), fever (2 subjects), nausea (2 subjects), lethargy (2 subjects), and loss of appetite (1 subject).

Safety in Ongoing Clinical Studies

This study is an ongoing multicenter, randomized, open-label study of adult subjects with documented transfusional iron overload in need of chelation therapy. Subjects received investigational product for 24 weeks with an extension of 72 weeks for the evaluation of long-term safety and efficacy. Subjects were stratified according to transfusional iron intake (transfusion burden) then randomized to receive Compound 1 at 16 or 32 mg/kg/day. The investigational product was administered orally once daily for 24 weeks. At the conclusion of the 24-week dosing period, qualified subjects were allowed to continue receiving Compound 1 for an additional 72 weeks. Dose adjustments from 24 weeks onward are permitted if clinically indicated. Fifty-one subjects enrolled and completed the first 24 weeks of the study; 49 subjects entered the 72-week extension.

Four subjects experienced 10 SAEs; none of the events were judged by the investigator to be related to treatment. One subject (0204) discontinued as the result of an SAE of vomiting. One subject (0403) in the 32 mg group discontinued the study at Week 20 as the result of an AE of increased transaminases. The event was moderate in severity and considered by the investigator as possibly related to the investigational product.

At least 1 related TEAE was reported in 61% (31/51) of subjects. All related TEAEs were of mild to moderate in severity. The most common TEAE was increased transaminases, which were reported for 8 subjects (15.7%) Treatment-related gastrointestinal TEAEs were reported for 17 (33.3%) subjects; the most common was flatulence (N=6; 11.8%) followed by diarrhea (N=3; 5.9%). Headache was reported for 5 (9.8%) subjects.

Figure 16:
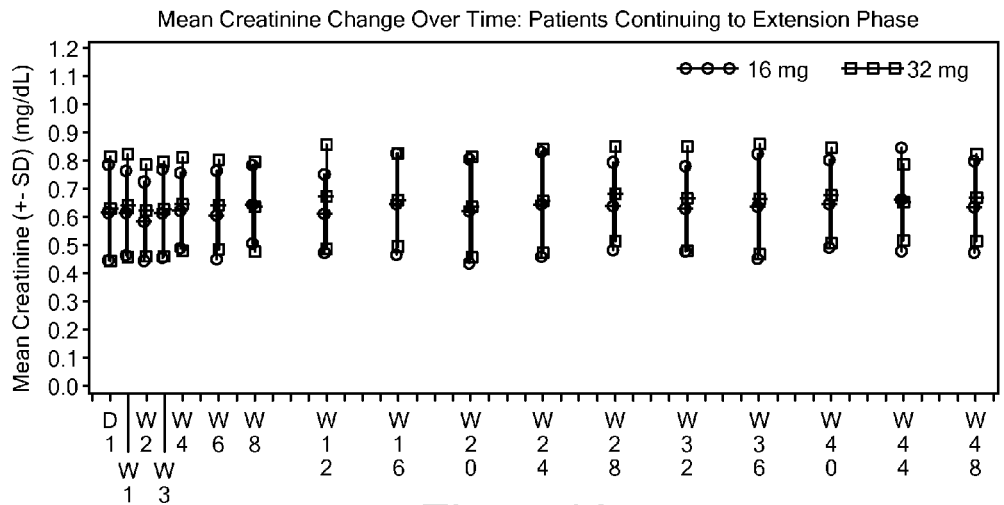
FIG. 16. Exemplary results illustrating mean creatinine change over time.

As of Week 48 there were no trends in serum creatinine levels. See FIG. 16.

Pediatric Study

A pediatric study is an ongoing Phase 2 multicenter, randomized, open-label study of pediatric subjects (aged 6-18 years) with documented transfusional iron overload in need of chelation therapy. 6 subjects (aged 12-<18 years) of a planned 30 subjects had been enrolled and administered investigational product. These subjects received a single dose for pharmacokinetic analysis with the option to continue in the 48-week study. No SAEs have been reported. Dosing was temporarily discontinued for 2 subjects; 1 subject for moderate decrease in neutrophil count, which was considered possibly related, and 1 for a mild upper respiratory tract infection that was considered not related. Treatment-emergent AEs were reported for 5 of the 6 subjects. Treatment emergent AEs considered possibly related to the investigational product include arthralgia (1), decreased neutrophil count (1), neutropenia (1), and headache (1).

Example 13

Polymorph Forms

Magnesium salt of (S)-3'-(OH)-DADFT-PE. The partial crystalline magnesium salt (Form A) was generated by mixing equal molar ratio of API solution in methanol with base slurry in MeOH/H$_2$O (11:1, v/v). The filtered supernatant was slowly evaporated under N$_2$, followed by rotary evaporation. Solid was generated by anti-solvent precipitation in ether. A large scale preparation of the magnesium was performed by mixing equal molar ratio of API solution in methanol with base suspension in methanol/water. The filtered supernatant was fast evaporated at ambient, and then dried under N$_2$. Solid was generated by anti-solvent precipitation in ether.

The solution proton NMR spectrum of the magnesium salt is consistent with the chemical structure of the API. Significant peak shifts were observed for all the protons in the API structure, implying salt formation. A sharp peak at ~3.3 ppm was assigned to water. Solvent DMSO was also observed at ~2.5 ppm.

The magnesium salt appears to be non-hygroscopic. It did not deliquesce when exposed to 75% RH for 8 days, and the XRPD pattern remained unchanged. The salt exhibits relatively high solubility in water (≥48 mg/ml).

Figure 17:
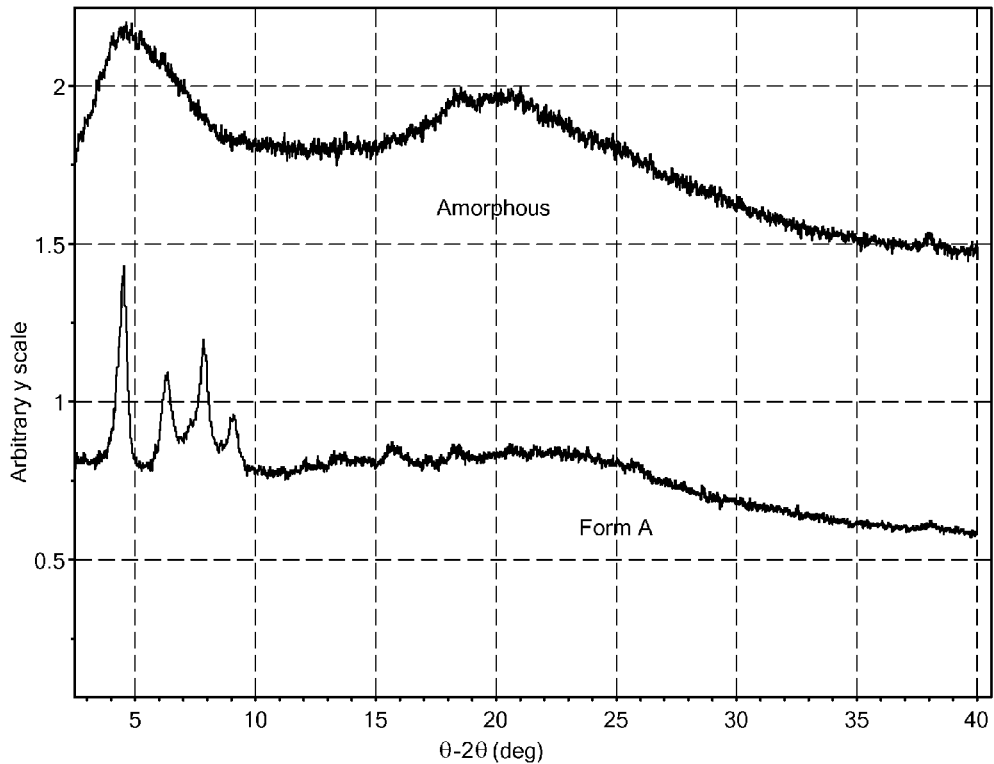
FIG. 17. XRPD Patterns of (S)-3'-(OH)-DADFT-PE magnesium salt: the amorphous form and form A (from top to bottom). Degrees θ-2θ on the abscissa are plotted against an arbitrary Y value on the ordinate.

The DSC thermogram curve of the magnesium salt Form B (FIG. 17) exhibits two broad endotherms. The major endotherm at approximately 79° C. is most likely due to the volatilization of water and is associated with a TG weight loss of ~16%. This weight loss is significantly higher than that observed for Form A. The nature of the minor endotherm at approximately 153° C. is unknown; however, it may be related to a phase transition. A TG weight loss of 2.2% is associated with this event.

Figure 18:
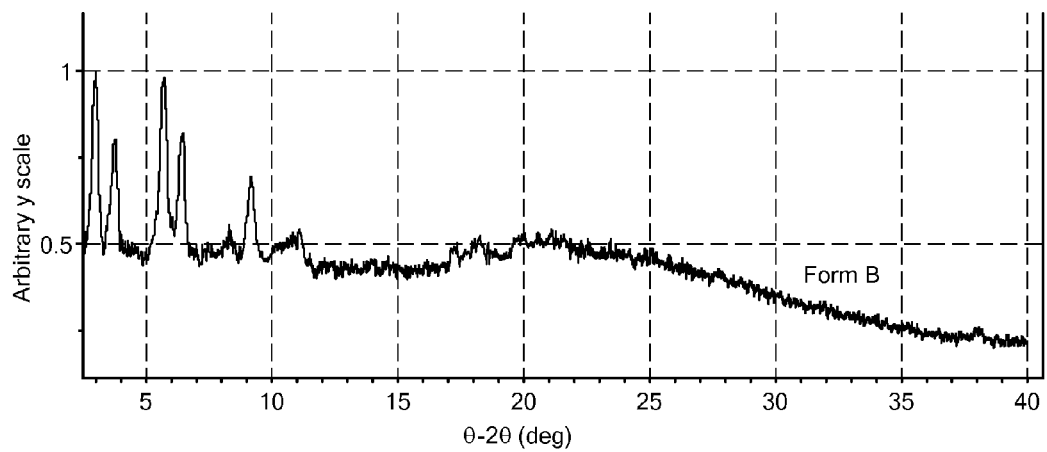
FIG. 18. XRPD Pattern of (S)-3'-(OH)-DADFT-PE magnesium salt form B. Degrees θ-2θ on the abscissa are plotted against an arbitrary Y value on the ordinate.
Figure 19:
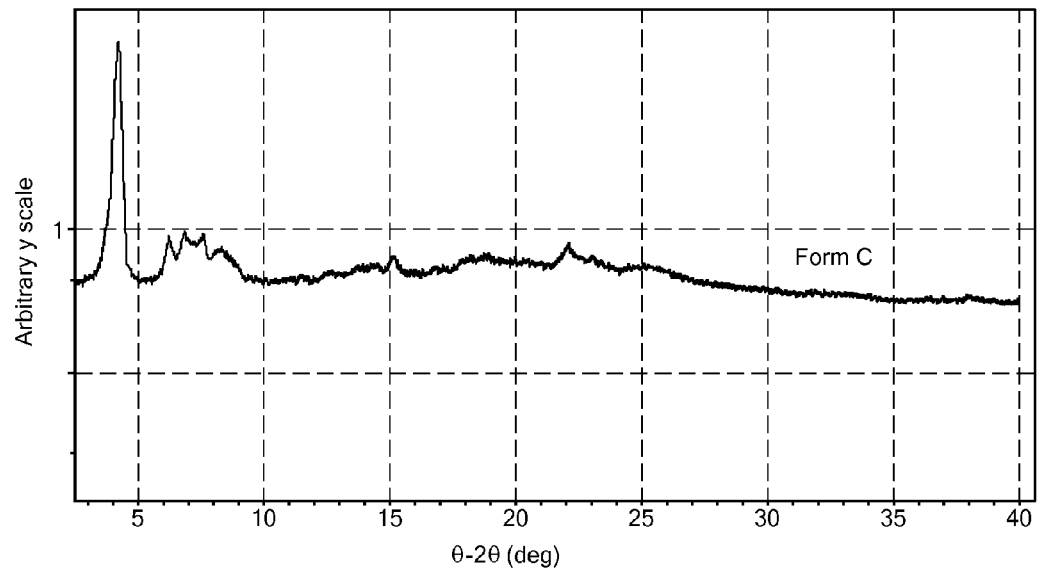
FIG. 19. XRPD Pattern of (S)-3'-(OH)-DADFT-PE magnesium salt form C. Degrees θ-2θ on the abscissa are plotted against an arbitrary Y value on the ordinate.
Figure 20:
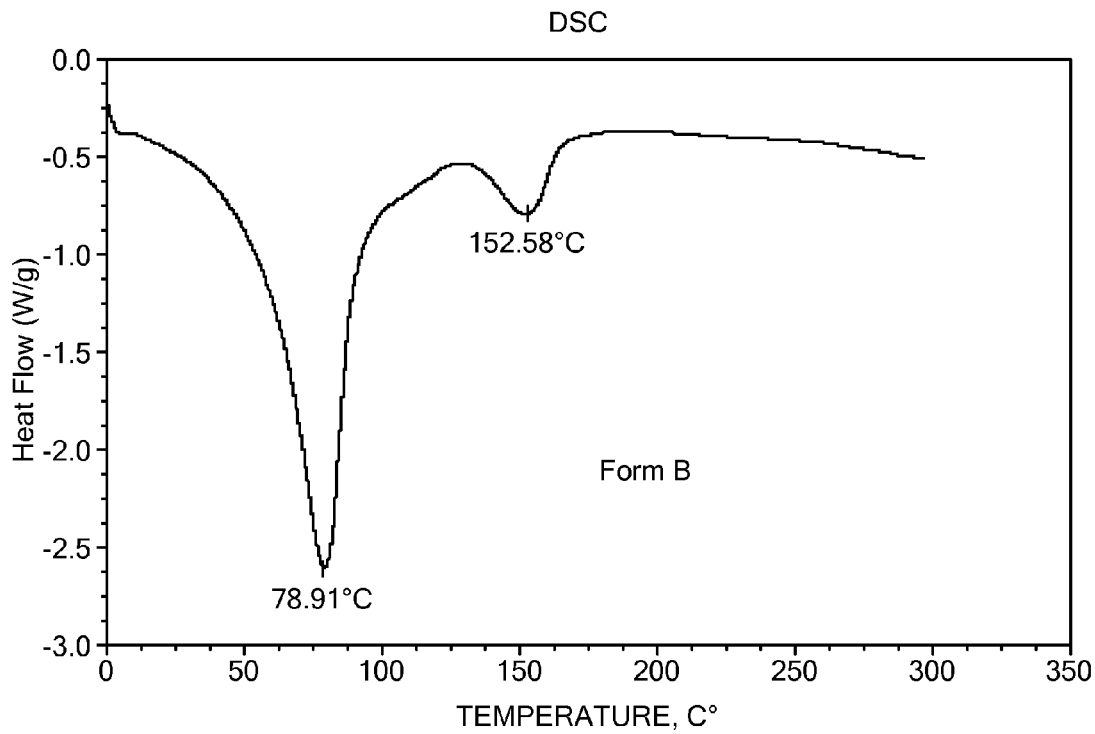
FIG. 20. DSC thermogram of (S)-3'-(OH)-DADFT-PE magnesium salt form B.
Figure 21:
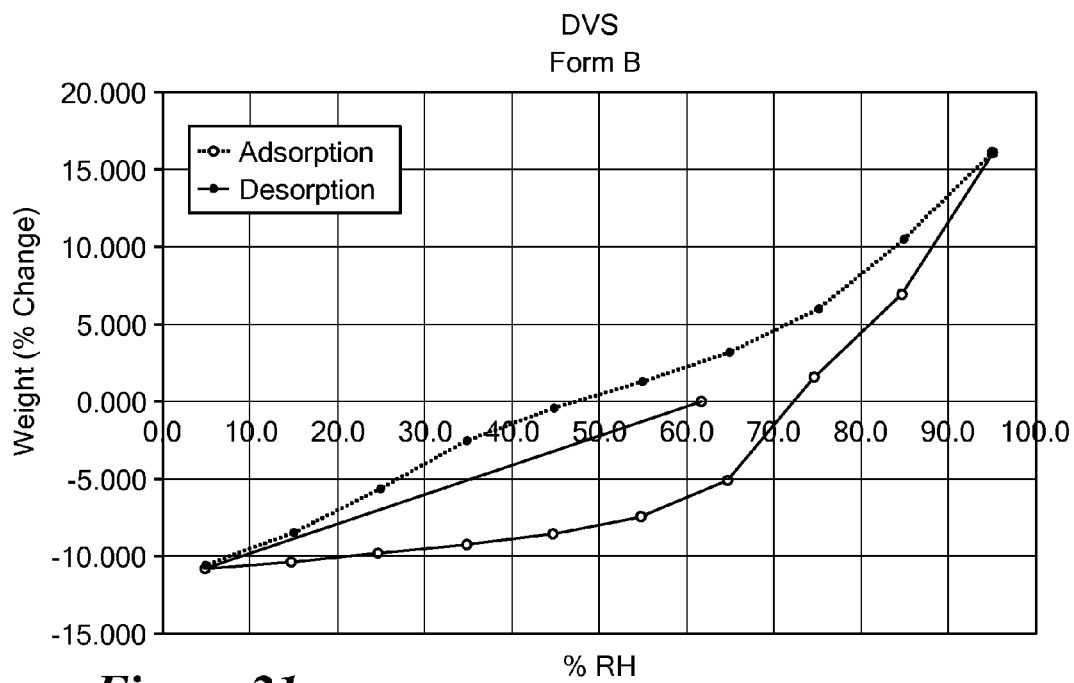
FIG. 21. Dynamic vapor sorption/desorption isotherm of (S)-3'-(OH)-DADFT-PE magnesium salt Form B.

The DVS data (FIG. 18) suggests that Form B is hygroscopic. The material exhibits 10.8% weight loss upon equilibrium at 5% RH. During the sorption step, the material exhibits a weight gain of 5.7% from 5% to 65% RH and an additional 21.2% weight above 65% RH without reaching equilibrium weight. This indicates that higher weight gains may be possible. A weight loss of 26.6% was observed upon desorption. The resulting sample exhibited a unique XRPD pattern (Form D).

The results of an initial polymorph screen crystallization experiments of the amorphous form of the magnesium salt of (S)-3'-(OH)-DADFT-PE are given below in Table 31, wherein FE stands for fast evaporation, SE stands for slow evaporation and LC stands for low crystallinity.

TABLE 31

| Solvent | Conditions | Description | XRPD Result |
| --- | --- | --- | --- |
| Acetone | FE | Yellow solid | A (LC) |
| | SE | Yellow film | Amorphous |
| ACN | FE | Yellow oil | — |
| | SE | Yellow film | Amorphous |
| DCM | FE | Yellow oil | — |
| | SE | Yellow film | Amorphous |
| 1,4-Dioxane | FE | Yellow oil | — |
| | SE | Yellow film | Amorphous |
| EtOH | Slurry (ambient) | Clear yellow solution | — |
| EtOAc | FE | Yellow oil | — |
| | SE | Yellow solid | A (LC) |
| Ethyl Ether | Slurry (ambient) | Yellow solid | — |
| HFIPA | FE | Yellow oil | — |
| | SE | Yellow oil | Amorphous |
| Hexanes | Slurry (ambient) | Yellow solid | — |
| IPA | Slurry (ambient) | White and yellow solid | — |
| MeOH | FE | Yellow oil | — |
| | SE | Yellow oil | Amorphous |
| MEK | FE | Yellow oil | — |
| | SE | Yellow solid | A (LC) |
| THF | FE | Yellow oil | — |
| | SE | Yellow film | Amorphous |
| Toluene | FE | Yellow film | Amorphous |
| | SE | Yellow solid | Amorphous |

TABLE 31-continued

| Solvent | Conditions | Description | XRPD Result |
|---|---|---|---|
| TFE | FE | Yellow oil | — |
|  | SE | Yellow film | Amorphous |
| Water | FE | Yellow oil | — |
|  | SE | Yellow solution | — |

The results of an initial polymorph screen crystallization experiments of (S)-3'-(OH)-DADFT-PE magnesium salt form A are given below in Table 32, wherein FE stands for fast evaporation and SE stands for slow evaporation.

TABLE 32

| Solvent | Conditions | Description | XRPD Result |
|---|---|---|---|
| Heptane/MeOH | SE | Tan solid | B |
| IPA/DCM | SE | Off-white solid | A |
| IPA/MeOH | FE | Tan solid | B |

The results of antisolvent precipitation experiments of (S)-3'-(OH)-DADFT-PE magnesium salt form A are given below in Table 33.

TABLE 33

| Solvent | Antisolvent | Description | XRPD Result |
|---|---|---|---|
| MeOH | Ether | White solid | A |
| MeOH | IPA | Yellow solid | A |
| Water | IPA | Yellow solid | B |

The results of slow cool crystallization experiments of (S)-3'-(OH)-DADFT-PE magnesium salt form A are given below in Table 34, wherein SC stands for slow cool, RT stands for room temperature, LC stands for low crystallinity, and IS stands for insufficient solid.

TABLE 34

| Solvent | Conditions | Description | XRPD Result |
|---|---|---|---|
| ACN | SC (~60° C. to RT) | Yellow solid | A (LC) |
| HFIPA | SC (~60° C. to RT) | No solid | — |
| MeOH | SC (~60° C. to RT) | White solid | IS |
| TFE | SC (~60° C. to RT) | No solid | — |
| THF | SC (~60° C. to RT) | Yellow solid | A (LC) |
| Water | SC (~60° C. to RT) | No solid | — |
| H$_2$O/IPA (1:1) | SC (~60° C. to RT) | No solid | — |
| MeOH/Acetone (1:1) | SC (~60° C. to RT) | No solid | — |
| EtOH/H$_2$O (1:1) | SC (~60° C. to RT) | No solid | — |

The results of ambient solution experiments of amorphous (S)-3'-(OH)-DADFT-PE magnesium salt are given below in Table 35, wherein LC stands for low crystallinity.

TABLE 35

| Solvent | Antisolvent | Description | XRPD Result |
|---|---|---|---|
| Acetone | — | Brown oil | — |
| ACN | Hexanes | White and yellow solid | A |
|  | Ethyl Ether | White solid | A |
|  | Ethyl Ether | Yellow solid | — |
| DCM | Hexanes | Yellow solid | Amorphous |
| 1,4-Dioxane | Hexanes | White cloudy solution | — |
| EtOAc | Hexanes | White solid | A |
|  | Hexanes | Yellow solid | A |
| HFIPA | Hexanes | Yellow film | — |
| MeOH | Ethyl Ether | No solid | — |
| MEK | Hexanes | Yellow solid | A (LC) |
|  | Hexanes | Yellow solid | A (LC) |
| THF | Hexanes | Off-White solid | A (LC) |
|  | Hexanes | Yellow solid | A (LC) |
| Toluene | Hexanes | Yellow cloudy solution | — |
| TFE | Hexanes | No solid | — |

The results of slurry experiments of (S)-3'-(OH)-DADFT-PE magnesium salt form A are given below in Table 36, wherein d stands for day, and IS stands for insufficient solid.

TABLE 36

| Solvent | Temp/Time | Description | XRPD Result |
|---|---|---|---|
| Acetone | 60° C./4 d | Off-white solid | A |
| 1,4-Dioxane | 60° C./4 d | White solid | C |
| EtOAc | 60° C./4 d | White solid | A |
| IPA | 60° C./4 d | Light yellow solid | Amorphous |
| Toluene | Ambient | White solid | A |
| Water | Ambient | Yellow solid | B |
| Water | 60° C./1 d | Yellow solid | Amorphous |
| ACN/THF (1:1) | 60° C./4 d | Yellow solid | A + peaks |
| EtOH/H$_2$O (1:9) | Ambient | White solid | IS |
| EtOH/H$_2$O (1:1) | Ambient | White solid | IS |
| EtOH/H$_2$O (9:1) | Ambient | Yellow solid | A |
| Heptane/DCM (2:8) | Ambient | Yellow solid | A (LC) |
| Heptane/EtOH (2:8) | Ambient | White solid | Amorphous |
| IPA/Acetone (1:1) | Ambient | White solid | IS |
| IPA/Acetone (2:8) | Ambient | White solid | A |
| IPA/EtOAc (2:8) | Ambient | White solid | A |
| IPA/Ether (2:8) | Ambient | White solid | A |

The results of vapor stress experiments of amorphous (S)-3'-(OH)-DADFT-PE magnesium salt are given below in Table 37, wherein LC stands for low crystallinity and IS stands for insufficient solid.

TABLE 37

| Solvent | Description | XRPD Result |
|---|---|---|
| Acetone | Yellow slurry | A (LC) |
| ACN | Yellow oil | — |
| DCM | Yellow solid | IS |
| 1,4-Dioxane | Yellow solid | IS |
| EtOH | Yellow oil | — |
| EtOAc | Yellow solid | IS |
| HFIPA | Yellow oil | — |
| IPA | Yellow oil | — |
| MeOH | Yellow oil | — |
| MEK | Yellow solid | IS |
| THF | Yellow oil | — |

TABLE 37-continued

| Solvent | Description | XRPD Result |
| --- | --- | --- |
| Toluene | Yellow oil | — |
| TFE | Yellow oil | — |
| Water | Yellow oil | — |

The results of vapor diffusion experiments of amorphous (S)-3'-(OH)-DADFT-PE magnesium salt are given below in Table 38, wherein LC stands for low crystallinity.

TABLE 38

| Solvent | Antisolvent | Description | XRPD Result |
| --- | --- | --- | --- |
| Acetone | Hexanes | Yellow solid | A (LC) |
| ACN | Ethyl Ether | Yellow solution | — |
| DCM | Hexanes | Yellow solid | A (LC) |
|  | Hexanes | Yellow solid | A (LC) |
| 1,4-Dioxane | Hexanes | White solid | — |
| EtOAc | Hexanes | White solid | A (LC) |
|  | Hexanes | Yellow solid | A (LC) |
| HFIPA | Ethyl Ether | Yellow solution | — |
| MeOH | Ethyl Ether | Fine cloudy layer of solid | — |
| MEK | Hexanes | Yellow solid | Amorphous |
| THF | Hexanes | Yellow and brown solid | A (LC) |
|  | Hexanes | Yellow solid | A (LC) |
| Toluene | Hexanes | Yellow solid | A (LC) |
| TFE | Ethyl Ether | Fine cloudy layer of solid | — |

The results of solvent grinding experiments of (S)-3'-(OH)-DADFT-PE magnesium salt form A are given below in Table 39, wherein LC stands for low crystallinity.

TABLE 39

| Solvent | Description | XRPD Result |
| --- | --- | --- |
| Acetone | Off-white solid | A |
| ACN | Off-white solid | A |
| 1,4-Dioxane | Light purple solid | C |
| 1,4-Dioxane | Light brown solid | C |
| Ethanol | Off-white solid | A |
| EtOAc | Light purple solid | A |
| IPA | Light purple solid | A |
| THF | Light brown solid | A |
| Water | Off-white solid | B |
| Water | Light brown solid | B |
| — | Off-white solid | A (LC) |

Figure 22A:
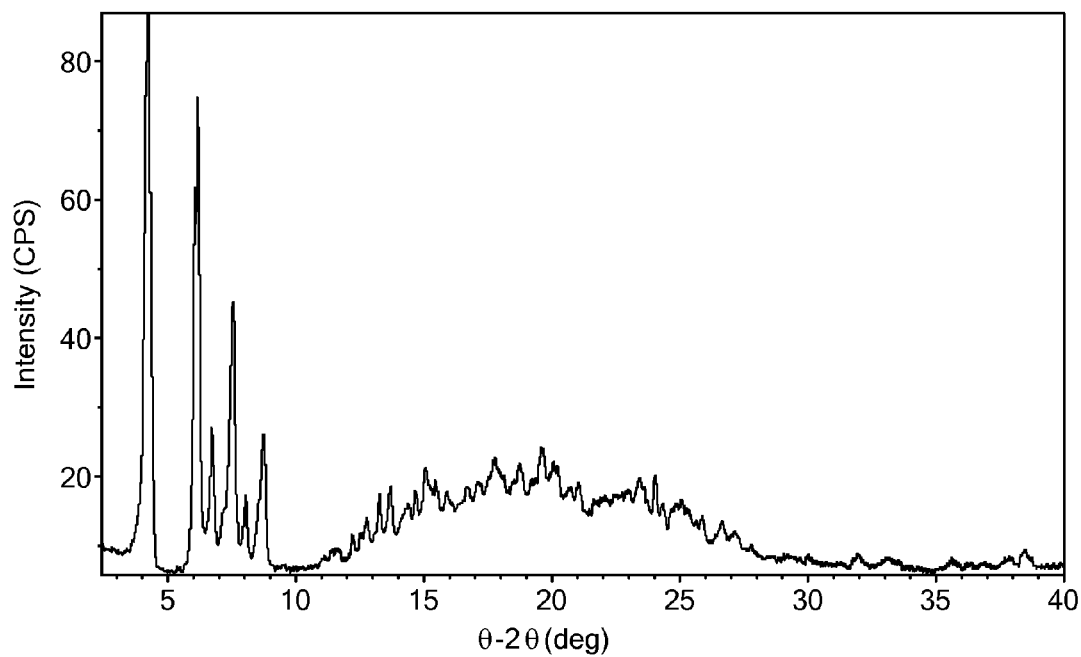
FIG. 22a. XRPD Patterns of (S)-3'-(OH)-DADFT-PE magnesium salt: form E from vacuum filtration.
Figure 22B:
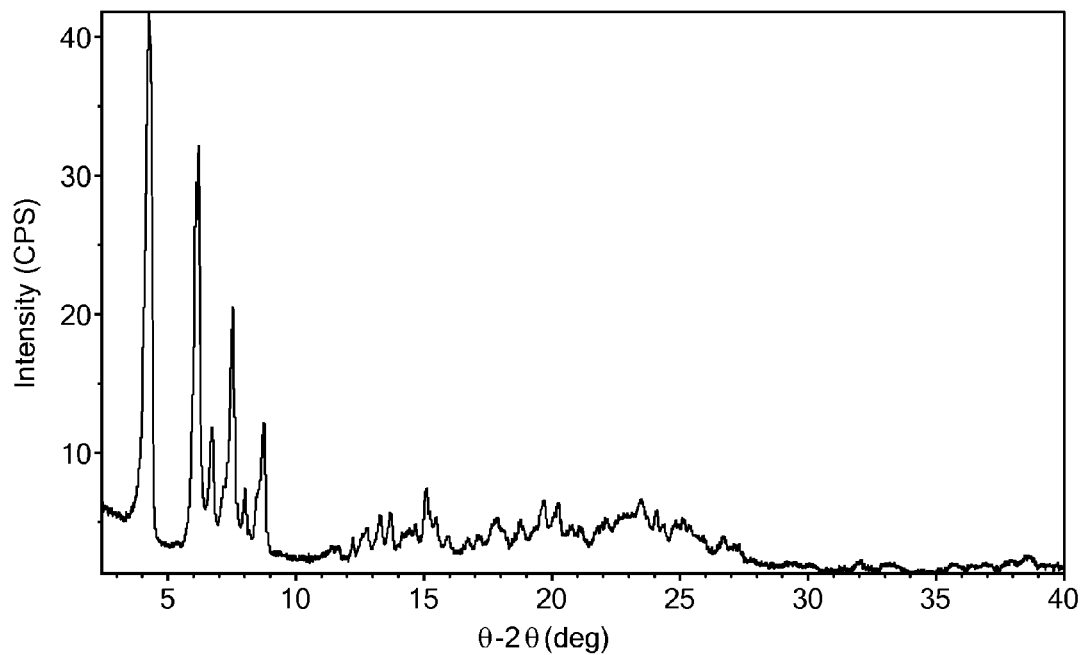
FIG. 22b. XRPD Patterns of (S)-3'-(OH)-DADFT-PE magnesium salt: form E from centrifugation.
Figure 23:
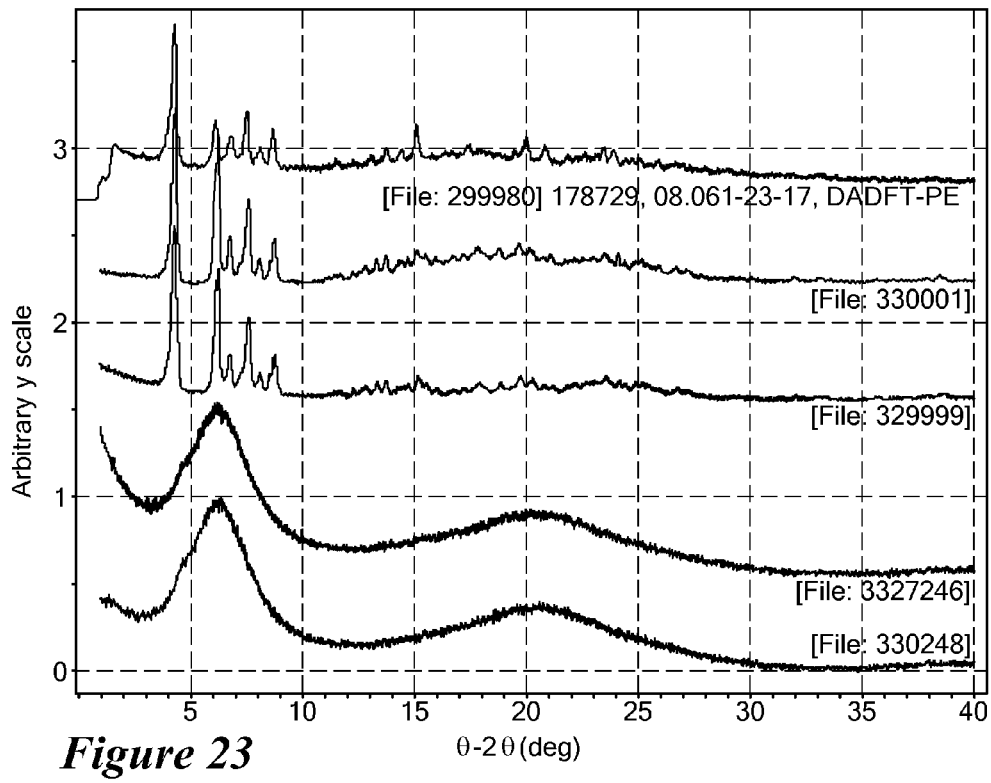
FIG. 23. XRPD patterns of (S)-3'-(OH)-DADFT-PE Mg under process conditions. From top to bottom: reference Form E pattern, post-filtration (wet), post-centrifugation (wet), post-filtration (dried), and post-centrifugation (dried).

To obtain Form E, amorphous material was slurried in EtOH/H₂O/MTBE in a 5.8:1:20 ratio, vacuum filtered or centrifuged to obtain the solid form, and analyzed by XRPD and Karl-Fischer both wet and after overnight vacuum drying at approximately 53° C. The XRPD and Karl-Fischer analyses identified both samples as Form E. The water content of filtered and centrifuged samples were 7.99 and 7.00% (w/w), respectively (see Table 40). Form E was obtained directly from the process solvents isolated as a moist cake. The centrifugation of the moist cake, to remove excess solvent, does not affect the crystalline form. See FIGS. 22a, 22b, and 23.

TABLE 40

| Conditions | Water content (wt %) | XRPD Result |
| --- | --- | --- |
| Vacuum filtered slurry, wet | 7.99 | E |
| Vacuum filtered slurry, vacuum/53° C., overnight | 1.00 | Amorphous |
| Centrifuged slurry, wet | 7.00 | E |
| Centrifuged slurry, vacuum/53° C., overnight | 0.86 | Amorphous |

Figure 24:
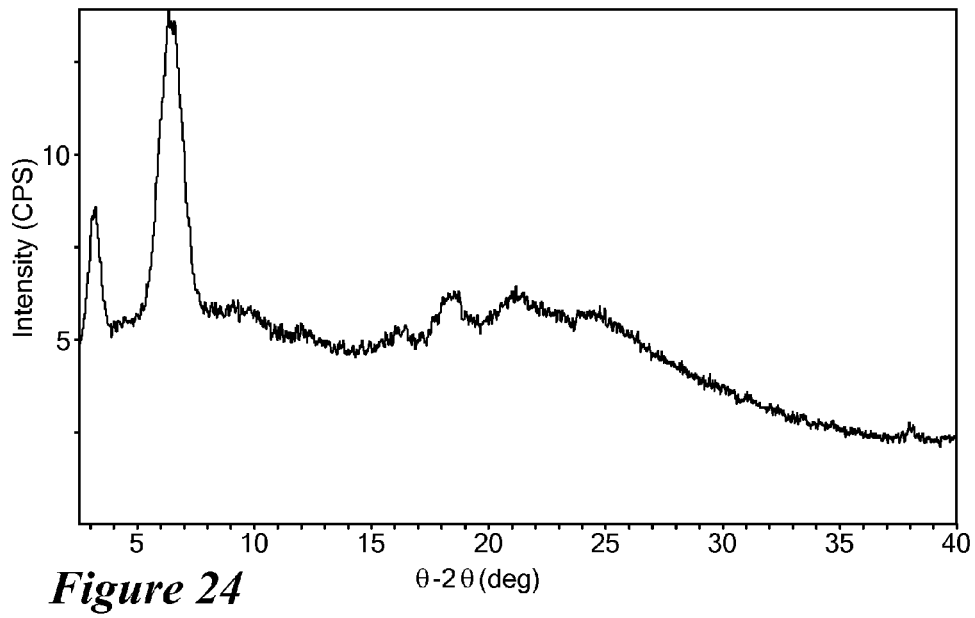
FIG. 24. XRPD Pattern of (S)-3'-(OH)-DADFT-PE magnesium salt: form D.

As described above, Form D was obtained via DVS experimentation with Form B, and Form B was generated with crystallization experiments using solvent mixtures containing methanol or water (e.g., MeOH/acetone, IPA/MeOH, heptane/MeOH, water (solvent grinding), water (antisolvent precipitation), or water (slurry at ambient)). DVS experimentation with Form B is as follows: Dynamic vapor sorption/desorption (DVS) data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the sample. Sodium chloride and polyvinylpyrrolidine were used as calibration standards. See FIG. 24.

From the foregoing description, one skilled in the art can easily ascertain the essential characteristics of this invention, and without departing from the spirit and scope thereof, can make various changes and modifications of the invention to adapt it to various usages and conditions.

All references, patents or applications, U.S. or foreign, cited in the application are hereby incorporated by reference as if written herein in their entireties. Where any inconsistencies arise, material literally disclosed herein controls.

What is claimed is:

1. A method for treating transfusional iron overload in a human subject in need of treatment, comprising a step of orally administering to the subject a solid dosage form of (S)-2-(2-hydroxy-3-(2-(2-(2-methoxyethoxy)ethoxy)ethoxy)phenyl)-4-methyl-4,5-dihydrothiazole-4-carboxylic acid or a salt thereof at a daily dose ranging from about 10-250 mg/kg of body weight.

2. The method of claim 1, wherein said salt is the magnesium hydroxide salt.

3. The method of claim 1, wherein said salt is a 3'-desaza-desferrithiocin polyether di-sodium salt.

4. The method of claim 1, wherein the daily dose is at least 40 mg/kg of body weight.

5. The method of claim 1, wherein the daily dose of at least 40 mg/kg of body weight is the initial dose for the treatment.

6. The method of claim 1, wherein the subject in need of treatment is suffering from β-thalassemia-intermediate, β-thalassemia-major, non-transfusion dependent Thalassaemia (NTDT), Blackfan-Diamond anemia, Sideroblastic anemia, sickle cell disease, aplastic anemia, red cell aplasia, Myelodysplasia (MDS), chronic myelofibrosis, paroxysmal nocturnal hemoglobinuria, off-therapy leukemia, hereditary hemochromatosis, or porphyria cutanea tarda.

7. The method of claim 6, wherein the human subject is suffering from β-thalassemia-intermediate.

8. The method of claim 1, wherein the human subject is an adult.

9. The method of claim 1, wherein the human subject is a pediatric patient.

10. The method of claim 2, wherein the magnesium hydroxide salt is the Form A polymorph.

* * * * *